United States Patent [19]
Attwood et al.

[11] Patent Number: 6,018,020
[45] Date of Patent: Jan. 25, 2000

[54] AMINO ACID DERIVATIVES

[75] Inventors: Michael Richard Attwood, Hitchin; David Nigel Hurst, Welwyn; Philip Stephen Jones, Welwyn Garden City; Paul Brittain Kay, Baldock; Tony Michael Raynham, Basildon; Francis Xavier Wilson, Welwyn Garden City, all of United Kingdom

[73] Assignee: Hoffman-La Roche Inc., Nutley, N.J.

[21] Appl. No.: 09/096,570

[22] Filed: Jun. 12, 1998

Related U.S. Application Data

[62] Division of application No. 08/971,036, Nov. 14, 1997, Pat. No. 5,866,684.

[30] Foreign Application Priority Data

Nov. 18, 1996 [GB] United Kingdom .................... 9623908

[51] Int. Cl.⁷ .................................................. A61K 38/08
[52] U.S. Cl. ............................ 530/329; 530/330; 514/17
[58] Field of Search ..................... 530/329, 330; 514/17

[56] References Cited

U.S. PATENT DOCUMENTS 5,384,410  1/1995  Kettner .................................... 548/405

FOREIGN PATENT DOCUMENTS

| WO 92/22570 | 12/1992 | WIPO . |
| WO 95/15766 | 6/1995 | WIPO . |
| WO 97/08304 | 3/1997 | WIPO . |

OTHER PUBLICATIONS

Steinkuchler, et al. Activity Of Purified Hepatitis C Virus Protease NS3 on Peptide Substrates, Journal of Virology, vol. 70, No. 10, pp. 6694–6700, (1996).

*Primary Examiner*—Cecilia J. Tsang
*Assistant Examiner*—David Lukton
*Attorney, Agent, or Firm*—George W. Johnston; William H. Epstein; Lewis J. Kreisler

[57] ABSTRACT

The invention provides amino acid derivatives of the formula

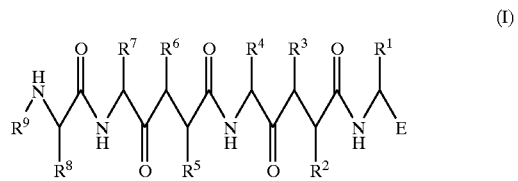

wherein
E represents CHO or $B(OH)_2$;
$R^1$ represents lower alkyl (optionally substituted by halo, cyano, lower alkylthio, aryl-lower alkylthio, aryl or heteroaryl), lower alkenyl or lower alkynyl;
$R^2$ represents lower alkyl optionally substituted by hydroxy, carboxy, aryl, aminocarbonyl or lower cycloalkyl; and
$R^3$ represents hydrogen or lower alkyl; or
$R^2$ and $R^3$ together represent di- or trimethylene optionally substituted by hydroxy;
$R^4$ represents lower alkyl (optionally substituted by hydroxy, lower cycloalkyl, carboxy, aryl, lower alkylthio, cyano-lower alkylthio or aryl-lower alkylthio), lower alkenyl, aryl or lower cycloalkyl;
$R^5$ represents lower alkyl (optionally substituted by hydroxy, lower alkylthio, aryl, aryl-lower alkylthio or cyano-lower alkylthio) or lower cycloalkyl;
$R^6$ represents hydrogen or lower alkyl;
$R^7$ represent lower alkyl (optionally substituted by hydroxy, carboxy, aryl or lower cycloalkyl) or lower cycloalkyl;
$R^8$ represents lower alkyl optionally substituted by hydroxy, carboxy or aryl; and
$R^9$ represents lower alkylcarbonyl, carboxy-lower alkylcarbonyl, arylcarbonyl, lower alkylsulphonyl, arylsulphonyl, lower alkoxycarbonyl or aryl-lower alkoxycarbonyl,
and salts of acidic compounds of formula I with bases, which are viral proteinase inhibitors useful as antiviral agents, especially for the treatment or prophylaxis of infections caused by Hepatitis C, Hepatitis G and human GB viruses.

3 Claims, 11 Drawing Sheets

```
  1  CCGACACCAT CGAATGGTGC AAAACCTTTC GCGGTATGGC
ATGATAGCGC

51  CCGGAAGAGA GTCAATTCAG GGTGGTGAAT GTGAAACCAG
TAACGTTATA

101  CGATGTCGCA GAGTATGCCG GTGTCTCTTA TCAGACCGTT
TCCCGCGTGG

151  TGAACCAGGC CAGCCACGTT TCTGCGAAAA CGCGGGAAAA
AGTGGAAGCG

201  GCGATGGCGG AGCTGAATTA CATTCCCAAC CGCGTGGCAC
AACAACTGGC

251  GGGCAAACAG TCGTTGCTGA TTGGCGTTGC CACCTCCAGT
CTGGCCCTGC

301  ACGCGCCGTC GCAAATTGTC GCGGCGATTA AATCTCGCGC
CGATCAACTG

351  GGTGCCAGCG TGGTGGTGTC GATGGTAGAA CGAAGCGGCG
TCGAAGCCTG

401  TAAAGCGGCG GTGCACAATC TTCTCGCGCA ACGCGTCAGT
GGGCTGATCA

451  TTAACTATCC GCTGGATGAC CAGGATGCCA TTGCTGTGGA
AGCTGCCTGC

501  ACTAATGTTC CGGCGTTATT TCTTGATGTC TCTGACCAGA
CACCCATCAA

551  CAGTATTATT TTCTCCCATG AAGACGGTAC GCGACTGGGC
GTGGAGCATC

601  TGGTCGCATT GGGTCACCAG CAAATCGCGC TGTTAGCGGG
CCCATTAAGT

651  TCTGTCTCGG CGCGTCTGCG TCTGGCTGGC TGGCATAAAT
ATCTCACTCG

701  CAATCAAATT CAGCCGATAG CGGAACGGGA AGGCGACTGG
AGTGCCATGT

751  CCGGTTTTCA ACAAACCATG CAAATGCTGA ATGAGGGCAT
CGTTCCCACT

801  GCGATGCTGG TTGCCAACGA TCAGATGGCG CTGGGCGCAA
TGCGCGCCAT
```

FIG. 1-1

851 TACCGAGTCC GGGCTGCGCG TTGGTGCGGA TATCTCGGTA GTGGGATACG

901 ACGATACCGA AGACAGCTCA TGTTATATCC CGCCGTTAAC CACCATCAAA

951 CAGGATTTTC GCCTGCTGGG GCAAACCAGC GTGGACCGCT TGCTGCAACT

1001 CTCTCAGGGC CAGGCGGTGA AGGGCAATCA GCTGTTGCCC GTCTCACTGG

1051 TGAAAAGAAA AACCACCCTG GCGCCCAATA CGCAAACCGC CTCTCCCCGC

1101 GCGTTGGCCG ATTCATTAAT GCAGCTGGCA CGACAGGTTT CCCGACTGGA

1151 AAGCGGGCAG TGAGCGCAAC GCAATTAATG TGAGTTAGCT CACTCATTAG

1201 GCACAATTCT CATGTTTGAC AGCTTATCAT CGACTGCACG GTGCACCAAT

1251 GCTTCTGGCG TCAGGCAGCC ATCGGAAGCT GTGGTATGGC TGTGCAGGTC

1301 GTAAATCACT GCATAATTCG TGTCGCTCAA GGCGCACTCC CGTTCTGGAT

1351 AATGTTTTTT GCGCCGACAT CATAACGGTT CTGGCAAATA TTCTGAAATG

1401 AGCTGTTGAC AATTAATCAT CGGCTCGTAT AATGTGTGGA ATTGTGAGCG

1451 GATAACAATT TCACACAGGA AACAGCCAGT CCGTTTAGGT GTTTTCACGA

1501 GCACTTCACC AACAAGGACC ATAGATT<u>ATG</u> AAAACTGAAG AAGGTAAACT
                                                                                                             Start MBP

1551 GGTAATCTGG ATTAACGGCG ATAAAGGCTA TAACGGTCTC GCTGAAGTCG

1601 GTAAGAAATT CGAGAAAGAT ACCGGAATTA AAGTCACCGT TGAGCATCCG

FIG. 1-2

```
1651  GATAAACTGG AAGAGAAATT CCCACAGGTT GCGGCAACTG
GCGATGGCCC

1701  TGACATTATC TTCTGGGCAC ACGACCGCTT TGGTGGCTAC
GCTCAATCTG

1751  GCCTGTTGGC TGAAATCACC CCGGACAAAG CGTTCCAGGA
CAAGCTGTAT

1801  CCGTTTACCT GGGATGCCGT ACGTTACAAC GGCAAGCTGA
TTGCTTACCC

1851  GATCGCTGTT GAAGCGTTAT CGCTGATTTA TAACAAAGAT
CTGCTGCCGA

1901  ACCCGCCAAA AACCTGGGAA GAGATCCCGG CGCTGGATAA
AGAACTGAAA

1951  GCGAAAGGTA AGAGCGCGCT GATGTTCAAC CTGCAAGAAC
CGTACTTCAC

2001  CTGGCCGCTG ATTGCTGCTG ACGGGGGTTA TGCGTTCAAG
TATGAAAACG

2051  GCAAGTACGA CATTAAAGAC GTGGGCGTGG ATAACGCTGG
CGCGAAAGCG

2101  GGTCTGACCT TCCTGGTTGA CCTGATTAAA AACAAACACA
TGAATGCAGA

2151  CACCGATTAC TCCATCGCAG AAGCTGCCTT TAATAAAGGC
GAAACAGCGA

2201  TGACCATCAA CGGCCCGTGG GCATGGTCCA ACATCGACAC
CAGCAAAGTG

2251  AATTATGGTG TAACGGTACT GCCGACCTTC AAGGGTCAAC
CATCCAAACC

2301  GTTCGTTGGC GTGCTGAGCG CAGGTATTAA CGCCGCCAGT
CCGAACAAAG

2351  AGCTGGCAAA AGAGTTCCTC GAAAACTATC TGCTGACTGA
TGAAGGTCTG

2401  GAAGCGGTTA ATAAAGACAA ACCGCTGGGT GCCGTAGCGC
TGAAGTCTTA

2451  CGAGGAAGAG TTGGCGAAAG ATCCACGTAT TGCCGCCACC
ATGGAAAACG
```

*FIG. 1-3*

2501 CCCAGAAAGG TGAAATCATG CCGAACATCC CGCAGATGTC
CGCTTTCTGG

2551 TATGCCGTGC GTACTGCGGT GATCAACGCC GCCAGCGGTC
GTCAGACTGT

2601 CGATGAAGCC CTGAAAGACG CGCAGACTAA TTCGAGCTCG
AACAACAACA

2651 ACAATAACAA TAACAACAAC CTCGGGATCG AGGGAAGGAT
TTCA<u>GAATTC</u>
EcoRI

2701 ATGGGGAGGG AGATACATCT GGGACCGGCA GACAGCCTTG
AAGGGCAGGG
           NS2/3 (

2751 GTGGCGACTC CTCGCGCATA TTACGGCCTA CTCTCAACAG
ACGCGGGGCC

2801 TACTTGGCTG CATCATCACT AGCCTCACAG GCCGGGACAG
GAACCAGGTC

2851 GAGGGGGAGG TCCAAATGGT CTCCACCGCA ACACAATCTT
TCCTGGCGAC

2901 CTGCGTCAAT GGCGTGTGTT GGACTGTCTA TCATGGTGCC
GGCTCAAAGA

2951 CCCTTGCCGG CCCAAAGGGC CAATCACCC AAATGTACAC
CAATGTGGAC

3001 CAGGACCTCG TCGGCTGGCA AGCGCCCCCC GGGGCGCGCT
CCTTGACACC

3051 ATGCACCTGC GGCAGCTCAG ACCTTTACTT GGTCACGAGG
CATGCCGATG

3101 TCATTCCGGT GCGCCGGCGG GGCGACAGCA GGGGAAGCCT
ACTCTCCCCC

3151 AGGCCCGTCT CCTACTTGAA GGGCTCTTCG GCCGGTCCAC
TGCTCTGCCC

3201 CTCGGGGCAC GCTGTGGGCA TCTTCCGGGC TGCCGTGTGC
ACCCGAGGGG

3251 TTGCGAAGGC GGTGGACTTT GTACCCGTCG AGTCTATGGA
AACCACTATG

*FIG. 1-4*

3301 CGGTCCCCGG TCTTCACGGA CAACTCGTCC CCTC<u>CGGCCG</u>
TATGCATGGG
                                                                                      Eag I    linker ( 3351 AGGAGGAGGA GGAGGAGGAG GAGGAGGAGG A<u>GGATCC</u>ATG
AGCACCTGGG
                                                                                      BamHI     NS4A (

3401 TGCTAGTAGG CGGAGTCCTA GCAGCTCTGG CCGCGTATTG
CCTGACAACA

3451 GGCAGCGTGG TCATTGTGGG CAGGATCGTC TTGTCCGGAA
AGCCGGCCAT

3501 CATTCCCGAC AGGGAAGTCC TCTACCGGGA GTTCGATGAG
ATGGAAGAGT

3551 GC<u>TAGAAGCT T</u>GGCACTGGC CGTCGTTTTA CAACGTCGTG
ACTGGGAAAA
        End HindIII

3601 CCCTGGCGTT ACCCAACTTA ATCGCCTTGC AGCACATCCC
CCTTTCGCCA

3651 GCTGGCGTAA TAGCGAAGAG GCCCGCACCG ATCGCCCTTC
CCAACAGTTG

3701 CGCAGCCTGA ATGGCGAATG GCAGCTTGGC TGTTTTGGCG
GATGAGATAA

3751 GATTTTCAGC CTGATACAGA TTAAATCAGA ACGCAGAAGC
GGTCTGATAA

3801 AACAGAATTT GCCTGGCGGC AGTAGCGCGG TGGTCCCACC
TGACCCCATG

3851 CCGAACTCAG AAGTGAAACG CCGTAGCGCC GATGGTAGTG
TGGGGTCTCC

3901 CCATGCGAGA GTAGGGAACT GCCAGGCATC AAATAAAACG
AAAGGCTCAG

3951 TCGAAAGACT GGGCCTTTCG TTTTATCTGT TGTTTGTCGG
TGAACGCTCT

4001 CCTGAGTAGG ACAAATCCGC CGGGAGCGGA TTTGAACGTT
GCGAAGCAAC

4051 GGCCCGGAGG GTGGCGGGCA GGACGCCCGC CATAAACTGC
CAGGCATCAA

4101 ATTAAGCAGA AGGCCATCCT GACGGATGGC CTTTTTGCGT
TTCTACAAAC

4151 TCTTTTTGTT TATTTTTCTA AATACATTCA AATATGTATC
CGCTCATGAG

*FIG. 1-5*

4201  ACAATAACCC TGATAAATGC TTCAATAATA TTGAAAAAGG
AAGAGTATGA

4251  GTATTCAACA TTTCCGTGTC GCCCTTATTC CCTTTTTTGC
GGCATTTTGC

4301  CTTCCTGTTT TTGCTCACCC AGAAACGCTG GTGAAAGTAA
AAGATGCTGA

4351  AGATCAGTTG GGTGCACGAG TGGGTTACAT CGAACTGGAT
CTCAACAGCG

4401  GTAAGATCCT TGAGAGTTTT CGCCCCGAAG AACGTTCTCC
AATGATGAGC

4451  ACTTTTAAAG TTCTGCTATG TGGCGCGGTA TTATCCCGTG
TTGACGCCGG

4501  GCAAGAGCAA CTCGGTCGCC GCATACACTA TTCTCAGAAT
GACTTGGTTG

4551  AGTACTCACC AGTCACAGAA AAGCATCTTA CGGATGGCAT
GACAGTAAGA

4601  GAATTATGCA GTGCTGCCAT AACCATGAGT GATAACACTG
CGGCCAACTT

FIG. 1-6

```
4651  ACTTCTGACA ACGATCGGAG GACCGAAGGA GCTAACCGCT
TTTTTGCACA

4701  ACATGGGGGA TCATGTAACT CGCCTTGATC GTTGGGAACC
GGAGCTGAAT

4751  GAAGCCATAC CAAACGACGA GCGTGACACC ACGATGCCTG
TAGCAATGGC

4801  AACAACGTTG CGCAAACTAT TAACTGGCGA ACTACTTACT
CTAGCTTCCC

4851  GGCAACAATT AATAGACTGG ATGGAGGCGG ATAAAGTTGC
AGGACCACTT

4901  CTGCGCTCGG CCCTTCCGGC TGGCTGGTTT ATTGCTGATA
AATCTGGAGC

4951  CGGTGAGCGT GGGTCTCGCG GTATCATTGC AGCACTGGGG
CCAGATGGTA

5001  AGCCCTCCCG TATCGTAGTT ATCTACACGA CGGGGAGTCA
GGCAACTATG

5051  GATGAACGAA ATAGACAGAT CGCTGAGATA GGTGCCTCAC
TGATTAAGCA

5101  TTGGTAACTG TCAGACCAAG TTTACTCATA TATACTTTAG
ATTGATTTAC

5151  CCCGGTTGAT AATCAGAAAA GCCCCAAAAA CAGGAAGATT
GTATAAGCAA

5201  ATATTTAAAT TGTAAACGTT AATATTTTGT TAAAATTCGC
GTTAAATTTT

5251  TGTTAAATCA GCTCATTTTT TAACCAATAG GCCGAAATCG
GCAAAATCCC

5301  TTATAAATCA AAGAATAGC CCGAGATAGG GTTGAGTGTT
GTTCCAGTTT

5351  GGAACAAGAG TCCACTATTA AAGAACGTGG ACTCCAACGT
CAAAGGGCGA

5401  AAAACCGTCT ATCAGGGCGA TGGCCCACTA CGTGAACCAT
CACCCAAATC

5451  AAGTTTTTTG GGGTCGAGGT GCCGTAAAGC ACTAAATCGG
AACCCTAAAG
```

*FIG. 1-7*

5501 GGAGCCCCCG ATTTAGAGCT TGACGGGGAA AGCCGGCGAA
CGTGGCGAGA

5551 AAGGAAGGGA AGAAAGCGAA AGGAGCGGGC GCTAGGGCGC
TGGCAAGTGT

5601 AGCGGTCACG CTGCGCGTAA CCACCACACC CGCCGCGCTT
AATGCGCCGC

5651 TACAGGGCGC GTAAAGGAT CTAGGTGAAG ATCCTTTTTG
ATAATCTCAT

5701 GACCAAAATC CCTTAACGTG AGTTTTCGTT CCACTGAGCG
TCAGACCCCG

5751 TAGAAAAGAT CAAAGGATCT TCTTGAGATC CTTTTTTTCT
GCGCGTAATC

5801 TGCTGCTTGC AAACAAAAAA ACCACCGCTA CCAGCGGTGG
TTTGTTTGCC

5851 GGATCAAGAG CTACCAACTC TTTTTCCGAA GGTAACTGGC
TTCAGCAGAG

5901 CGCAGATACC AAATACTGTC CTTCTAGTGT AGCCGTAGTT
AGGCCACCAC

5951 TTCAAGAACT CTGTAGCACC GCCTACATAC CTCGCTCTGC
TAATCCTGTT

6001 ACCAGTGGCT GCTGCCAGTG GCGATAAGTC GTGTCTTACC
GGGTTGGACT

6051 CAAGACGATA GTTACCGGAT AAGGCGCAGC GGTCGGGCTG
AACGGGGGGT

6101 TCGTGCACAC AGCCCAGCTT GGAGCGAACG ACCTACACCG
AACTGAGATA

6151 CCTACAGCGT GAGCTATGAG AAAGCGCCAC GCTTCCCGAA
GGGAGAAAGG

6201 CGGACAGGTA TCCGGTAAGC GGCAGGGTCG GAACAGGAGA
GCGCACGAGG

6251 GAGCTTCCAG GGGGAAACGC CTGGTATCTT TATAGTCCTG
TCGGGTTTCG

6301 CCACCTCTGA CTTGAGCGTC GATTTTTGTG ATGCTCGTCA
GGGGGGCGGA

*FIG. 1-8*

```
    6351  GCCTATGGAA AAACGCCAGC AACGCGGCCT TTTTACGGTT
CCTGGCCTTT

6401  TGCTGGCCTT TTGCTCACAT GTTCTTTCCT GCGTTATCCC
CTGATTCTGT

6451  GGATAACCGT ATTACCGCCT TTGAGTGAGC TGATACCGCT
CGCCGCAGCC

6501  GAACGACCGA GCGCAGCGAG TCAGTGAGCG AGGAAGCGGA
AGAGCGCCTG

6551  ATGCGGTATT TTCTCCTTAC GCATCTGTGC GGTATTTCAC
ACCGCATATG

6601  GTGCACTCTC AGTACAATCT GCTCTGATGC CGCATAGTTA
AGCCAGTATA

6651  CACTCCGCTA TCGCTACGTG ACTGGGTCAT GGCTGCGCCC
CGACACCCGC

6701  CAACACCCGC TGACGCGCCC TGACGGGCTT GTCTGCTCCC
GGCATCCGCT

6751  TACAGACAAG CTGTGACCGT CTCCGGGAGC TGCATGTGTC
AGAGGTTTTC

6801  ACCGTCATCA CCGAAACGCG CGAGGCAGCT GCGGTAAAGC
TCATCAGCGT

6851  GGTCGTGCAG CGATTCACAG ATGTCTGCCT GTTCATCCGC
GTCCAGCTCG

6901  TTGAGTTTCT CCAGAAGCGT TAATGTCTGG CTTCTGATAA
AGCGGGCCAT

6951  GTTAAGGGCG GTTTTTTCCT GTTTGGTCAC TTGATGCCTC
CGTGTAAGGG

7001  GGAATTTCTG TTCATGGGGG TAATGATACC GATGAAACGA
GAGAGGATGC

7051  TCACGATACG GGTTACTGAT GATGAACATG CCCGGTTACT
GGAACGTTGT

7101  GAGGGTAAAC AACTGGCGGT ATGGATGCGG CGGGACCAGA
GAAAAATCAC

7151  TCAGGGTCAA TGCCAGCGCT TCGTTAATAC AGATGTAGGT
GTTCCACAGG
```

FIG. 1-9

```
7201  GTAGCCAGCA GCATCCTGCG ATGCAGATCC GGAACATAAT
GGTGCAGGGC

7251  GCTGACTTCC GCGTTTCCAG ACTTTACGAA ACACGGAAAC
CGAAGACCAT

7301  TCATGTTGTT GCTCAGGTCG CAGACGTTTT GCAGCAGCAG
TCGCTTCACG

7351  TTCGCTCGCG TATCGGTGAT TCATTCTGCT AACCAGTAAG
GCAACCCCGC

7401  CAGCCTAGCC GGGTCCTCAA CGACAGGAGC ACGATCATGC
GCACCCGTGG

7451  CCAGGACCCA ACGCTGCCCG AAATT
```

*FIG. 1-10*

MBP (

```
  1  MKTEEGKLVI  WINGDKGYNG  LAEVGKKFEK  DTGIKVTVEH  PDKLEEKFPQ
 51  VAATGDPDI   IFWAHDRFGG  YAQSGLLAEI  TPDKAFQDKL  YPFTWDAVRY
101  NGKLIAYPIA  VEALSLIYNK  DLLPNPPKTW  EEIPALDKEL  KAKGKSALMF
151  NLQEPYFTWP  LIAADGGYAF  KYENGKYDIK  DVGVDNAGAK  AGLTFLVDLI
201  KNKHMNADTD  YSIAEAAFNK  GETAMTINGP  WAWSNIDTSK  VNYGVTVLPT
251  FKGQPSKPFV  GVLSAGINAA  SPNKELAKEF  LENYLLTDEG  LEAVNKDKPL
301  GAVALKSYEE  ELAKDPRIAA  TMENAQKGEI  MPNIPQMSAF  WYAVRTAVIN
351  AASGRQTVDE  ALKDAQTNSS  SNNNNNNNNN  NLGIEGRISE  FMGREIHLGP
```

NS2/3 (

```
401  ADSLEGQGWR  LLAHITAYSQ  QTRGLLGCII  TSLTGRDRNQ  VEGEVQMVST
451  ATQSFLATCV  NGVCWTVYHG  AGSKTLAGPK  GPITQMYTNV  DQDLVGWQAP
501  PGARSLTPCT  CGSSDLYLVT  RHADVIPVRR  RGDSRGSLLS  PRPVSYLKGS
551  SGGPLLCPSG  HAVGIFRAAV  CTRGVAKAVD  FVPVESMETT  MRSPVFTDNS
601  SPPAVCMGGG  GGGGGGGGGS  MSTWVLVGGV  LAALAAYCLT  TGSVVIVGRI
```

Linker ( NS4A (

```
651  VLSGKPAIIP  DREVLYREFD  EMEEC
```

FIG. 2

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 7475 base pairs
        (B) TYPE: nucleic acid
        (C) STRANDEDNESS: double
        (D) TOPOLOGY: circular (ii) MOLECULE TYPE: DNA (genomic)

(iii) HYPOTHETICAL: NO (xi) SEQUENCE DESCRIPTION: SEQ ID NO:1:

```
CCGACACCAT CGAATGGTGC AAAACCTTTC GCGGTATGGC ATGATAGCGC CCGGAAGAGA      60

GTCAATTCAG GGTGGTGAAT GTGAAACCAG TAACGTTATA CGATGTCGCA GAGTATGCCG     120

GTGTCTCTTA TCAGACCGTT TCCCGCGTGG TGAACCAGGC CAGCCACGTT TCTGCGAAAA     180

CGCGGGAAAA AGTGGAAGCG GCGATGGCGG AGCTGAATTA CATTCCCAAC CGCGTGGCAC     240

AACAACTGGC GGGCAAACAG TCGTTGCTGA TTGGCGTTGC CACCTCCAGT CTGGCCCTGC     300

ACGCGCCGTC GCAAATTGTC GCGGCGATTA AATCTCGCGC CGATCAACTG GGTGCCAGCG     360

TGGTGGTGTC GATGGTAGAA CGAAGCGGCG TCGAAGCCTG TAAAGCGGCG GTGCACAATC     420

TTCTCGCGCA ACGCGTCAGT GGGCTGATCA TTAACTATCC GCTGGATGAC CAGGATGCCA     480

TTGCTGTGGA AGCTGCCTGC ACTAATGTTC CGGCGTTATT TCTTGATGTC TCTGACCAGA     540

CACCCATCAA CAGTATTATT TTCTCCCATG AAGACGGTAC GCGACTGGGC GTGGAGCATC     600
```

```
TGGTCGCATT GGGTCACCAG CAAATCGCGC TGTTAGCGGG CCCATTAAGT TCTGTCTCGG      660

CGCGTCTGCG TCTGGCTGGC TGGCATAAAT ATCTCACTCG CAATCAAATT CAGCCGATAG      720

CGGAACGGGA AGGCGACTGG AGTGCCATGT CCGGTTTTCA ACAAACCATG CAAATGCTGA      780

ATGAGGGCAT CGTTCCCACT GCGATGCTGG TTGCCAACGA TCAGATGGCG CTGGGCGCAA      840

TGCGCGCCAT TACCGAGTCC GGGCTGCGCG TTGGTGCGGA TATCTCGGTA GTGGGATACG      900

ACGATACCGA AGACAGCTCA TGTTATATCC CGCCGTTAAC CACCATCAAA CAGGATTTTC      960

GCCTGCTGGG GCAAACCAGC GTGGACCGCT TGCTGCAACT CTCTCAGGGC CAGGCGGTGA     1020

AGGGCAATCA GCTGTTGCCC GTCTCACTGG TGAAAAGAAA AACCACCCTG GCGCCCAATA     1080

CGCAAACCGC CTCTCCCCGC GCGTTGGCCG ATTCATTAAT GCAGCTGGCA CGACAGGTTT     1140

CCCGACTGGA AAGCGGGCAG TGAGCGCAAC GCAATTAATG TGAGTTAGCT CACTCATTAG     1200

GCACAATTCT CATGTTTGAC AGCTTATCAT CGACTGCACG GTGCACCAAT GCTTCTGGCG     1260

TCAGGCAGCC ATCGGAAGCT GTGGTATGGC TGTGCAGGTC GTAAATCACT GCATAATTCG     1320

TGTCGCTCAA GGCGCACTCC CGTTCTGGAT AATGTTTTTT GCGCCGACAT CATAACGGTT     1380

CTGGCAAATA TTCTGAAATG AGCTGTTGAC AATTAATCAT CGGCTCGTAT AATGTGTGGA     1440

ATTGTGAGCG GATAACAATT TCACACAGGA AACAGCCAGT CCGTTTAGGT GTTTTCACGA     1500

GCACTTCACC AACAAGGACC ATAGATTATG AAAACTGAAG AAGGTAAACT GGTAATCTGG     1560

ATTAACGGCG ATAAAGGCTA TAACGGTCTC GCTGAAGTCG GTAAGAAATT CGAGAAAGAT     1620

ACCGGAATTA AAGTCACCGT TGAGCATCCG GATAAACTGG AAGAGAAATT CCCACAGGTT     1680

GCGGCAACTG GCGATGGCCC TGACATTATC TTCTGGGCAC ACGACCGCTT TGGTGGCTAC     1740

GCTCAATCTG GCCTGTTGGC TGAAATCACC CCGGACAAAG CGTTCCAGGA CAAGCTGTAT     1800

CCGTTTACCT GGGATGCCGT ACGTTACAAC GGCAAGCTGA TTGCTTACCC GATCGCTGTT     1860

GAAGCGTTAT CGCTGATTTA TAACAAAGAT CTGCTGCCGA ACCCGCCAAA AACCTGGGAA     1920

GAGATCCCGG CGCTGGATAA AGAACTGAAA GCGAAAGGTA AGAGCGCGCT GATGTTCAAC     1980

CTGCAAGAAC CGTACTTCAC CTGGCCGCTG ATTGCTGCTG ACGGGGGTTA TGCGTTCAAG     2040

TATGAAAACG GCAAGTACGA CATTAAAGAC GTGGGCGTGG ATAACGCTGG CGCGAAAGCG     2100

GGTCTGACCT TCCTGGTTGA CCTGATTAAA AACAAACACA TGAATGCAGA CACCGATTAC     2160

TCCATCGCAG AAGCTGCCTT TAATAAAGGC GAAACAGCGA TGACCATCAA CGGCCCGTGG     2220

GCATGGTCCA ACATCGACAC CAGCAAAGTG AATTATGGTG TAACGGTACT GCCGACCTTC     2280

AAGGGTCAAC CATCCAAACC GTTCGTTGGC GTGCTGAGCG CAGGTATTAA CGCCGCCAGT     2340

CCGAACAAAG AGCTGGCAAA AGAGTTCCTC GAAAACTATC TGCTGACTGA TGAAGGTCTG     2400

GAAGCGGTTA ATAAAGACAA ACCGCTGGGT GCCGTAGCGC TGAAGTCTTA CGAGGAAGAG     2460

TTGGCGAAAG ATCCACGTAT TGCCGCCACC ATGGAAAACG CCCAGAAAGG TGAAATCATG     2520

CCGAACATCC CGCAGATGTC CGCTTTCTGG TATGCCGTGC GTACTGCGGT GATCAACGCC     2580

GCCAGCGGTC GTCAGACTGT CGATGAAGCC CTGAAAGACG CGCAGACTAA TTCGAGCTCG     2640

AACAACAACA ACAATAACAA TAACAACAAC CTCGGGATCG AGGGAAGGAT TTCAGAATTC     2700

ATGGGGAGGG AGATACATCT GGGACCGGCA GACAGCCTTG AAGGGCAGGG GTGGCGACTC     2760

CTCGCGCATA TTACGGCCTA CTCTCAACAG ACGCGGGGCC TACTTGGCTG CATCATCACT     2820

AGCCTCACAG GCCGGGACAG GAACCAGGTC GAGGGGGAGG TCCAAATGGT CTCCACCGCA     2880

ACACAATCTT TCCTGGCGAC CTGCGTCAAT GGCGTGTGTT GGACTGTCTA TCATGGTGCC     2940

GGCTCAAAGA CCCTTGCCGG CCCAAAGGGC CCAATCACCC AAATGTACAC CAATGTGGAC     3000
```

```
CAGGACCTCG TCGGCTGGCA AGCGCCCCCC GGGGCGCGCT CCTTGACACC ATGCACCTGC    3060

GGCAGCTCAG ACCTTTACTT GGTCACGAGG CATGCCGATG TCATTCCGGT GCGCCGGCGG    3120

GGCGACAGCA GGGGAAGCCT ACTCTCCCCC AGGCCCGTCT CCTACTTGAA GGGCTCTTCG    3180

GGCGGTCCAC TGCTCTGCCC CTCGGGCAC GCTGTGGGCA TCTTCCGGGC TGCCGTGTGC    3240

ACCCGAGGGG TTGCGAAGGC GGTGGACTTT GTACCCGTCG AGTCTATGGA AACCACTATG    3300

CGGTCCCCGG TCTTCACGGA CAACTCGTCC CCTCCGGCCG TATGCATGGG AGGAGGAGGA    3360

GGAGGAGGAG GAGGAGGAGG AGGATCCATG AGCACCTGGG TGCTAGTAGG CGGAGTCCTA    3420

GCAGCTCTGG CCGCGTATTG CCTGACAACA GGCAGCGTGG TCATTGTGGG CAGGATCGTC    3480

TTGTCCGGAA AGCCGGCCAT CATTCCCGAC AGGGAAGTCC TCTACCGGGA GTTCGATGAG    3540

ATGGAAGAGT GCTAGAAGCT TGGCACTGGC CGTCGTTTTA CAACGTCGTG ACTGGGAAAA    3600

CCCTGGCGTT ACCCAACTTA ATCGCCTTGC AGCACATCCC CCTTTCGCCA GCTGGCGTAA    3660

TAGCGAAGAG GCCCGCACCG ATCGCCCTTC CCAACAGTTG CGCAGCCTGA ATGGCGAATG    3720

GCAGCTTGGC TGTTTTGGCG GATGAGATAA GATTTTCAGC CTGATACAGA TTAAATCAGA    3780

ACGCAGAAGC GGTCTGATAA AACAGAATTT GCCTGGCGGC AGTAGCGCGG TGGTCCCACC    3840

TGACCCCATG CCGAACTCAG AAGTGAAACG CCGTAGCGCC GATGGTAGTG TGGGGTCTCC    3900

CCATGCGAGA GTAGGGAACT GCCAGGCATC AAATAAAACG AAAGGCTCAG TCGAAAGACT    3960

GGGCCTTTCG TTTTATCTGT TGTTTGTCGG TGAACGCTCT CCTGAGTAGG ACAAATCCGC    4020

CGGGAGCGGA TTTGAACGTT GCGAAGCAAC GGCCCGGAGG GTGGCGGGCA GGACGCCCGC    4080

CATAAACTGC CAGGCATCAA ATTAAGCAGA AGGCCATCCT GACGGATGGC CTTTTTGCGT    4140

TTCTACAAAC TCTTTTTGTT TATTTTTCTA AATACATTCA AATATGTATC CGCTCATGAG    4200

ACAATAACCC TGATAAATGC TTCAATAATA TTGAAAAAGG AAGAGTATGA GTATTCAACA    4260

TTTCCGTGTC GCCCTTATTC CCTTTTTTGC GGCATTTTGC CTTCCTGTTT TTGCTCACCC    4320

AGAAACGCTG GTGAAAGTAA AAGATGCTGA AGATCAGTTG GGTGCACGAG TGGGTTACAT    4380

CGAACTGGAT CTCAACAGCG GTAAGATCCT TGAGAGTTTT CGCCCCGAAG AACGTTCTCC    4440

AATGATGAGC ACTTTTAAAG TTCTGCTATG TGGCGCGGTA TTATCCCGTG TTGACGCCGG    4500

GCAAGAGCAA CTCGGTCGCC GCATACACTA TTCTCAGAAT GACTTGGTTG AGTACTCACC    4560

AGTCACAGAA AAGCATCTTA CGGATGGCAT GACAGTAAGA GAATTATGCA GTGCTGCCAT    4620

AACCATGAGT GATAACACTG CGGCCAACTT ACTTCTGACA ACGATCGGAG GACCGAAGGA    4680

GCTAACCGCT TTTTTGCACA ACATGGGGGA TCATGTAACT CGCCTTGATC GTTGGGAACC    4740

GGAGCTGAAT GAAGCCATAC CAAACGACGA GCGTGACACC ACGATGCCTG TAGCAATGGC    4800

AACAACGTTG CGCAAACTAT TAACTGGCGA ACTACTTACT CTAGCTTCCC GGCAACAATT    4860

AATAGACTGG ATGGAGGCGG ATAAAGTTGC AGGACCACTT CTGCGCTCGG CCCTTCCGGC    4920

TGGCTGGTTT ATTGCTGATA AATCTGGAGC CGGTGAGCGT GGGTCTCGCG GTATCATTGC    4980

AGCACTGGGG CCAGATGGTA AGCCCTCCCG TATCGTAGTT ATCTACACGA CGGGGAGTCA    5040

GGCAACTATG GATGAACGAA ATAGACAGAT CGCTGAGATA GGTGCCTCAC TGATTAAGCA    5100

TTGGTAACTG TCAGACCAAG TTTACTCATA TATACTTTAG ATTGATTTAC CCCGGTTGAT    5160

AATCAGAAAA GCCCCAAAAA CAGGAAGATT GTATAAGCAA ATATTTAAAT TGTAAACGTT    5220

AATATTTTGT TAAAATTCGC GTTAAATTTT TGTTAAATCA GCTCATTTTT TAACCAATAG    5280

GCCGAAATCG GCAAAATCCC TTATAAATCA AAAGAATAGC CCGAGATAGG GTTGAGTGTT    5340

GTTCCAGTTT GGAACAAGAG TCCACTATTA AGAACGTGG ACTCCAACGT CAAAGGGCGA    5400
```

```
AAAACCGTCT ATCAGGGCGA TGGCCCACTA CGTGAACCAT CACCCAAATC AAGTTTTTTG    5460

GGGTCGAGGT GCCGTAAAGC ACTAAATCGG AACCCTAAAG GGAGCCCCCG ATTTAGAGCT    5520

TGACGGGGAA AGCCGGCGAA CGTGGCGAGA AGGAAGGGA AGAAAGCGAA AGGAGCGGGC    5580

GCTAGGGCGC TGGCAAGTGT AGCGGTCACG CTGCGCGTAA CCACCACACC CGCCGCGCTT    5640

AATGCGCCGC TACAGGGCGC GTAAAAGGAT CTAGGTGAAG ATCCTTTTTG ATAATCTCAT    5700

GACCAAAATC CCTTAACGTG AGTTTCGTT CCACTGAGCG TCAGACCCCG TAGAAAAGAT     5760

CAAAGGATCT TCTTGAGATC CTTTTTTTCT GCGCGTAATC TGCTGCTTGC AAACAAAAAA    5820

ACCACCGCTA CCAGCGGTGG TTTGTTTGCC GGATCAAGAG CTACCAACTC TTTTTCCGAA    5880

GGTAACTGGC TTCAGCAGAG CGCAGATACC AAATACTGTC CTTCTAGTGT AGCCGTAGTT    5940

AGGCCACCAC TTCAAGAACT CTGTAGCACC GCCTACATAC CTCGCTCTGC TAATCCTGTT    6000

ACCAGTGGCT GCTGCCAGTG GCGATAAGTC GTGTCTTACC GGGTTGGACT CAAGACGATA    6060

GTTACCGGAT AAGGCGCAGC GGTCGGGCTG AACGGGGGGT TCGTGCACAC AGCCCAGCTT    6120

GGAGCGAACG ACCTACACCG AACTGAGATA CCTACAGCGT GAGCTATGAG AAAGCGCCAC    6180

GCTTCCCGAA GGGAGAAAGG CGGACAGGTA TCCGGTAAGC GGCAGGGTCG AACAGGAGA     6240

GCGCACGAGG GAGCTTCCAG GGGGAAACGC CTGGTATCTT TATAGTCCTG TCGGGTTTCG    6300

CCACCTCTGA CTTGAGCGTC GATTTTTGTG ATGCTCGTCA GGGGGGCGGA GCCTATGGAA    6360

AAACGCCAGC AACGCGGCCT TTTTACGGTT CCTGGCCTTT TGCTGGCCTT TTGCTCACAT    6420

GTTCTTTCCT GCGTTATCCC CTGATTCTGT GGATAACCGT ATTACCGCCT TTGAGTGAGC    6480

TGATACCGCT CGCCGCAGCC GAACGACCGA GCGCAGCGAG TCAGTGAGCG AGGAAGCGGA    6540

AGAGCGCCTG ATGCGGTATT TTCTCCTTAC GCATCTGTGC GGTATTTCAC ACCGCATATG    6600

GTGCACTCTC AGTACAATCT GCTCTGATGC CGCATAGTTA AGCCAGTATA CACTCCGCTA    6660

TCGCTACGTG ACTGGGTCAT GGCTGCGCCC CGACACCCGC CAACACCCGC TGACGCGCCC    6720

TGACGGGCTT GTCTGCTCCC GGCATCCGCT TACAGACAAG CTGTGACCGT CTCCGGGAGC    6780

TGCATGTGTC AGAGGTTTTC ACCGTCATCA CCGAAACGCG CGAGGCAGCT GCGGTAAAGC    6840

TCATCAGCGT GGTCGTGCAG CGATTCACAG ATGTCTGCCT GTTCATCCGC GTCCAGCTCG    6900

TTGAGTTTCT CCAGAAGCGT TAATGTCTGG CTTCTGATAA AGCGGGCCAT GTTAAGGGCG    6960

GTTTTTTCCT GTTTGGTCAC TTGATGCCTC CGTGTAAGGG GGAATTTCTG TTCATGGGGG    7020

TAATGATACC GATGAAACGA GAGAGGATGC TCACGATACG GGTTACTGAT GATGAACATG    7080

CCCGGTTACT GGAACGTTGT GAGGGTAAAC AACTGGCGGT ATGGATGCGG CGGGACCAGA    7140

GAAAAATCAC TCAGGGTCAA TGCCAGCGCT TCGTTAATAC AGATGTAGGT GTTCCACAGG    7200

GTAGCCAGCA GCATCCTGCG ATGCAGATCC GGAACATAAT GGTGCAGGGC GCTGACTTCC    7260

GCGTTTCCAG ACTTTACGAA ACACGGAAAC CGAAGACCAT TCATGTTGTT GCTCAGGTCG    7320

CAGACGTTTT GCAGCAGCAG TCGCTTCACG TTCGCTCGCG TATCGGTGAT TCATTCTGCT    7380

AACCAGTAAG GCAACCCCGC CAGCCTAGCC GGGTCCTCAA CGACAGGAGC ACGATCATGC    7440

GCACCCGTGG CCAGGACCCA ACGCTGCCCG AAATT                              7475
```

(2) INFORMATION FOR SEQ ID NO:2:

(i) SEQUENCE CHARACTERISTICS:
        (A) LENGTH: 675 amino acids
        (B) TYPE: amino acid
        (D) TOPOLOGY: linear (ii) MOLECULE TYPE: protein (iii) HYPOTHETICAL: NO (xi) SEQUENCE DESCRIPTION: SEQ ID NO:2:

```
Met Lys Thr Glu Glu Gly Lys Leu Val Ile Trp Ile Asn Gly Asp Lys
  1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
 50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Asn Leu Gly Ile
    370                 375                 380

Glu Gly Arg Ile Ser Glu Phe Met Gly Arg Glu Ile His Leu Gly Pro
385                 390                 395                 400

Ala Asp Ser Leu Glu Gly Gln Gly Trp Arg Leu Leu Ala His Ile Thr
```

```
                     405                 410                 415
Ala Tyr Ser Gln Gln Thr Arg Gly Leu Leu Gly Cys Ile Ile Thr Ser
            420                 425                 430

Leu Thr Gly Arg Asp Arg Asn Gln Val Glu Gly Glu Val Gln Met Val
            435                 440                 445

Ser Thr Ala Thr Gln Ser Phe Leu Ala Thr Cys Val Asn Gly Val Cys
            450                 455                 460

Trp Thr Val Tyr His Gly Ala Gly Ser Lys Thr Leu Ala Gly Pro Lys
465                 470                 475                 480

Gly Pro Ile Thr Gln Met Tyr Thr Asn Val Asp Gln Asp Leu Val Gly
            485                 490                 495

Trp Gln Ala Pro Pro Gly Ala Arg Ser Leu Thr Pro Cys Thr Cys Gly
            500                 505                 510

Ser Ser Asp Leu Tyr Leu Val Thr Arg His Ala Asp Val Ile Pro Val
            515                 520                 525

Arg Arg Arg Gly Asp Ser Arg Gly Ser Leu Leu Ser Pro Arg Pro Val
            530                 535                 540

Ser Tyr Leu Lys Gly Ser Ser Gly Gly Pro Leu Leu Cys Pro Ser Gly
545                 550                 555                 560

His Ala Val Gly Ile Phe Arg Ala Ala Val Cys Thr Arg Gly Val Ala
                565                 570                 575

Lys Ala Val Asp Phe Val Pro Val Glu Ser Met Glu Thr Thr Met Arg
                580                 585                 590

Ser Pro Val Phe Thr Asp Asn Ser Ser Pro Pro Ala Val Cys Met Gly
                595                 600                 605

Gly Gly Gly Gly Gly Gly Gly Gly Gly Ser Met Ser Thr Trp
610                 615                 620

Val Leu Val Gly Gly Val Leu Ala Ala Leu Ala Ala Tyr Cys Leu Thr
625                 630                 635                 640

Thr Gly Ser Val Val Ile Val Gly Arg Ile Val Leu Ser Gly Lys Pro
                645                 650                 655

Ala Ile Ile Pro Asp Arg Glu Val Leu Tyr Arg Glu Phe Asp Glu Met
                660                 665                 670

Glu Glu Cys
        675
```

AMINO ACID DERIVATIVES

This is a divisional of application Ser. No. 08/971,036 filed on Nov. 14, 1997, now U.S. Pat. No. 5,866,684.

FIELD OF THE INVENTION

The present invention is concerned with amino acid derivatives and a process for their manufacture.

SUMMARY OF THE INVENTION

The amino acid derivatives provided by the present invention are compounds of the formula

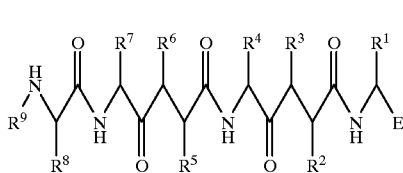

(I)

wherein
E represents CHO or B(OH)$_2$;
R$^1$ represents lower alkyl, halo-lower alkyl, cyano-lower alkyl, lower alkylthio-lower alkyl, aryl-lower alkylthio-lower alkyl, aryl-lower alkyl, heteroaryl-lower alkyl, lower alkenyl or lower alkynyl;
R$^2$ represents lower alkyl, hydroxy-lower alkyl, carboxy-lower alkyl, aryl-lower alkyl, aminocarbonyl-lower alkyl or lower cycloalkyl-lower alkyl; and
R$^3$ represents hydrogen or lower alkyl; or
R$^2$ and R$^3$ together represent di- or trimethylene optionally substituted by hydroxy;
R$^4$ represents lower alkyl, hydroxy-lower alkyl, lower cycloalkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl or lower cycloalkyl;
R$^5$ represents lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;
R$^6$ represents hydrogen or lower alkyl;
R$^7$ represent lower alkyl, hydroxy-lower alkyl, carboxy-lower alkyl, aryl-lower alkyl, lower cycloalkyl-lower alkyl or lower cycloalkyl;
R$^8$ represents lower alkyl, hydroxy-lower alkyl, carboxy-lower alkyl or aryl-lower alkyl; and
R$^9$ represents lower alkylcarbonyl, carboxy-lower alkylcarbonyl, arylcarbonyl, lower alkylsulphonyl, arylsulphonyl, lower alkoxycarbonyl or aryl-lower alkoxycarbonyl;
and salts of acidic compounds of formula I with bases.

The compounds of formula I and their aforementioned salts inhibit proteinases of viral origin and are useful in the treatment of viral infections, particularly viral infections caused by Hepatitis C, Hepatitis G and the human GB viruses.

This invention also provides processes of producing compounds of formula I comprising: (a) when E is CHO, treating a corresponding acetal with a strong acid; or (b) when E is B(OH)$_2$, treating a corresponding dioxaborolane with a strong base or an alkali metal periodate.

DESCRIPTION OF THE FIGURES

FIG. 1—Nucleotide sequence of pMAL-NS3" Gly 12 NS4A plasmid (SEQ ID NO: 1).

FIG. 2—Amino acid sequence of MBP-NS3"-gly 12-4A enzyme (SEQ ID NO: 2).

Amino acids 1–391—Maltose binding protein and other sequences derived from New England Biolabs vector pMAL™-c2.

Amino acids 393–605 and 622–675—HCV-derived sequences (amino acids 1007–1219 and 1658–1711 of HCV polyprotein respectively).

Amino acids 606–621—linker region.

DETAILED DESCRIPTION OF THE INVENTION

This invention provides compounds of the formula

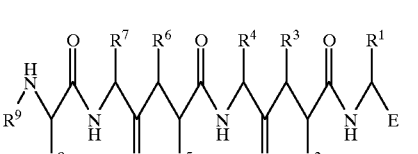

(I)

wherein
E is CHO or B(OH)$_2$;
R$^1$ is lower alkyl, halo-lower alkyl, cyano-lower alkyl, lower alkylthio-lower alkyl, aryl-lower alkylthio-lower alkyl, aryl-lower alkyl, heteroaryl-lower alkyl, lower alkenyl or lower alkynyl;
R$^2$ is lower alkyl, hydroxy-lower alkyl, carboxy-lower alkyl, aryl-lower alkyl, aminocarbonyl-lower alkyl or lower cycloalkyl-lower alkyl; and
R$^3$ is hydrogen or lower alkyl; or
R$^2$ and R$^3$ together are di- or trimethylene optionally substituted by hydroxy;
R$^4$ is lower alkyl, hydroxy-lower alkyl, lower cycloalkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl or lower cycloalkyl;
R$^5$ is lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;
R$^6$ is hydrogen or lower alkyl;
R$^7$ is lower alkyl, hydroxy-lower alkyl, carboxy-lower alkyl, aryl-lower alkyl, lower cycloalkyl-lower alkyl or lower cycloalkyl;
R$^8$ is lower alkyl, hydroxy-lower alkyl, carboxy-lower alkyl or aryl-lower alkyl; and
R$^9$ is lower alkylcarbonyl, carboxy-lower alkylcarbonyl, arylcarbonyl, lower alkylsulphonyl, arylsulphonyl, lower alkoxycarbonyl or aryl-lower alkoxycarbonyl,
and salts of acidic compounds of formula I with bases.

As used in this specification, the term "lower alkyl", alone or in combination, denotes a straight-chain or branched chain alkyl group containing 1–7, preferably 1–4, carbon atoms, e.g. methyl, ethyl, n-propyl, isopropyl, n-butyl, isobutyl, sec.butyl, tert.butyl, n-pentyl, neopentyl and the like. "The terms "lower alkenyl" and "lower alkynyl" denote alkenyl groups preferably containing 2–7 carbon atoms, e.g. vinyl, allyl, n-propenyl, n-butenyl, and the like, and, respectively, alkynyl groups containing 2–7 carbon atoms, e.g. propargyl and the like. The term "lower cycloalkyl" denotes a cycloalkyl group containing 3–7 carbon atoms, e.g. cyclopropyl, cyclobutyl, cyclopentyl and the like. The lower alkoxy part of a "lower alkoxycarbonyl" group is a lower alkyl ether group in which the lower alkyl moiety has the aforementioned significance. The term "aryl" denotes a monocyclic or polycyclic aromatic hydrocarbon group, e.g. phenyl, naphthyl or the like which is unsubstituted or substituted by one or more substituents selected from e.g. lower alkyl, lower alkoxy, nitro, halo, halo-lower alkyl, hydroxy, acetamido and the like. The term "heteroaryl" denotes a 5- or 6-membered aromatic heterocyclic group which contains N, O and/or S as the hetero atom(s) and which is optionally benz-fused and/or substituted in the same manner as the aryl group defined above. Examples of heteroaryl groups are furyl, thienyl, pyridyl, pyrimidinyl, benzofuranyl, benzothienyl, quinolyl, isoquinolyl and the like.

The compounds of formula I contain at least six asymmetric carbon atoms and can therefore exist in the form of optically pure diastereoisomers, mixtures of diastereoisomers, diastereoisomeric racemates or mixtures of diastereoisomeric racemates. The present invention includes within its scope all of these possible forms.

One class of preferred compounds of formula I comprises those in which $R^1$ represents lower alkyl, halo-lower alkyl, lower alkylthio-lower alkyl, aryl-lower alkylthio-lower alkyl, heteroaryl-lower alkyl, lower alkenyl or lower alkynyl. Fluoro-lower alkyl is the preferred halo-lower alkyl group. Preferred heteroaryl-lower alkyl groups are thienyl-lower alkyl and furyl-lower alkyl. In a preferred embodiment of each of the embodiments of compounds of formula I described above, $R^2$ represents lower alkyl, lower cycloalkyl-lower alkyl or aryl-lower alkyl. In a preferred embodiment of each of the embodiments of compounds of formula I described above, $R^3$ represents hydrogen. In another preferred embodiment of each of the embodiments of compounds of formula I described above, $R^2$ and $R^3$ together represent trimethylene optionally substituted by hydroxy. In a preferred embodiment of each of the embodiments of compounds of formula I described above, $R^4$ represents lower alkyl, lower cycloalkyl-lower alkyl, aryl-lower alkyl, aryl or lower cycloalkyl. In a preferred embodiment of each of the embodiments of compounds of formula I described above, $R^5$ represents aryl-lower alkyl or lower cycloalkyl. In a preferred embodiment of each of the embodiments of compounds of formula I described above, $R^6$ represents hydrogen. In a preferred embodiment of each of the embodiments of compounds of formula I described above, $R^7$ represents lower alkyl, carboxy-lower alkyl aryl-lower alkyl or hydroxy-lower alkyl. In a preferred embodiment of each of the embodiments of compounds of formula I described above, $R^8$ represents hydroxy-lower alkyl, carboxy-lower alkyl or aryl-lower alkyl. In a preferred embodiment of each of the embodiments of compounds of formula I described above, $R^9$ represents lower alkylcarbonyl or carboxy-lower alkylcarbonyl.

Examples of these preferred compounds in which E represents CHO are:

2(S)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]butyraldehyde;

2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4,4-difluorovaleraldehyde;

2(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4,4,4-trifluorobutyraidehyde;

2(R)-[[N-[N-[N-[N-[N-(3-carboxypropionyl)-L-α-aspartyl]-L-αglutamyl]-2-methyl-L-phenylalanyl]-3-methyl-L-valyl]-L-leucyl]amino]-3-(methylthio)propionaldehyde;

2(R)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-3-(butylthio)propionaldehyde;

2(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-pentenaldehyde;

2(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-pentynal;

2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-hexynal;

3-(benzylthio)-2(R)-[[N-[N-[N-[N-(3-carboxypropionyl)-L-α-aspartyl]-L-α-glutamyl]-2-methyl-L-phenylalanyl]-3-methyl-L-valyl]-L-leucyl]amino]propionaldehyde;

2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-3-(2-thienyl)propionaldehyde;

2(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-3-(3-thienyl)propionaldehyde;

2(RS)-[[N-[N-[N-[N-[N-(3-carboxypropionyl)-L-α-aspartyl]-3-(2-naphthyl)-D-alanyl]-2-methyl-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-seryl-D-valyl]-2-methyl-L-phenylalanyl]-3-methyl-L-valyl]-L-leucyl]amino]-4,4,4-trifluorobutyraldehyde;

2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]hexanal;

(Z)-2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-hexenal;

2(RS)-[[N-[N-[N-[N-[N-(benzyloxycarbonyl)-L-α-aspartyl]-L-α-glutamyl]-2-methyl-L-phenylalany]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-L-α-glutamyl]-4-chloro-L-phenylalanyl]-3-methyl-L-valyl]-L-leucyl]amino]-4,4,4-trifluorobutyraldehyde;

2(RS)-[[N-[N-[N-[N-[N-(3-carboxypropionyl)-L-α-aspartyl]-D-valyl]-2-methyl-L-phenylalanyl]-3-methyl-L-valyl]-L-leucyl]amino]-4,4,4-trifluorobutyraldehyde;

2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5-methylhexanal;

2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5-hexenal;

2(RS)-[[[N-[N-[N-[N-(3-carboxypropionyl)-L-α-aspartyl]-D-norleucyl]-2-methyl-L-phenylalanyl-3-methyl-L-valyl]-L-leucyl]amino]-4,4,4-trifluorobutyraldehyde;

2(RS)-[[N-[N-[N-[N-(3-carboxypropionyl)-L-α-aspartyl]-D-2-cyclohexylglycyl]-2-methyl-L-phenylalanyl]-3-methyl-L-valyl]-L-leucyl]amino]-4,4,4-trifluorobutyraldehyde; and 2(RS)-[[N-[N-[N-[N-[N-(4-acetamidobenzoyl)-L-α-aspartyl]-L-α-glutamyl]-2-methyl-L-phenylalanyl]-3-methyl-L-valyl]-L-leucyl]amino]-4,4,4-trifluorobutyraldehyde;

and examples of these preferred compounds in which E represents B(OH)$_2$ are:

1(RS)-[[N-[N-[N-[N-[N-(3-Carboxypropionyl)-L-α-aspartyl]-L-α-glutamyl]-2-methyl-L-phenylalanyl]-3-methyl-L-valyl]-L-leucyl]amino]propylboronic acid;

1(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]butylboronic acid;

1(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-3-butenylboronic acid;

1(RS)-[[N-[N-[N-[N-(3-carboxypropionyl)-L-α-aspartyl]-L-α-glutamyl]-4-chloro-2-methyl-L-phenylalanyl]-3-methyl-L-valyl]-L-leucyl]amino]-3-butenylboronic acid;

1(RS)-[[N-[N-[N-[N-[N-(3-carboxypropionyl)-L-α-aspartyl]-L-α-glutamyl]-2-methyl-L-phenylalanyl]-3-methyl-L-valyl]-3-cyclopentyl-L-alanyl]amino]-3-butenylboronic acid;

1(R)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]pentylboronic acid;

1(RS)-[[N-[N-[N-[N-[N-(3-carboxypropionyl)-L-α-aspartyl]-L-α-glutamyl]-2-methyl-L-phenylalanyl]-L-2-cyclohexylglycyl]-L-leucyl]aminolpropylboronic acid;

1(RS)-[[N-[N-[N-[N-[N-(3-carboxypropionyl)-L-α-aspartyl]-L-α-glutamyl]-L-2-cyclohexylglycyl]-3-methyl-L-valyl]-L-leucyl]amino]propylboronic acid; and 1(RS)-[[N-[N-[N-[N-[N-(benzyloxycarbonyl)-L-α-aspartyl]-D-valyl]-2-methyl-L-phenylalanyl]-3-methyl-L-valyl-L-leucyl]amino]propylboronic acid.

This invention provides a process for producing a compound of the formula:

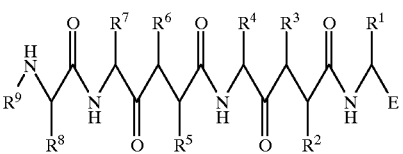

wherein

E is CHO;

$R^1$ is lower alkyl, halo-lower alkyl, cyano-lower alkyl, lower alkylthio-lower alkyl, aryl-lower alkylthio-lower alkyl, aryl-lower alkyl, heteroaryl-lower alkyl, lower alkenyl or lower alkynyl;

$R^2$ is lower alkyl, hydroxy-lower alkyl, carboxy-lower alkyl, aryl-lower alkyl, aminocarbonyl-lower alkyl or lower cycloalkyl-lower alkyl; and $R^3$ is hydrogen or lower alkyl; or $R^2$ and $R^3$ together are di- or trimethylene optionally substituted by hydroxy;

$R^4$ is lower alkyl, hydroxy-lower alkyl, lower cycloalkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl or lower cycloalkyl;

$R^5$ is lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;

$R^6$ is hydrogen or lower alkyl;

$R^7$ is lower alkyl, hydroxy-lower alkyl, carboxy-lower alkyl, aryl-lower alkyl, lower cycloalkyl-lower alkyl or lower cycloalkyl;

$R^8$ is lower alkyl, hydroxy-lower alkyl, carboxy-lower alkyl or aryl-lower alkyl; and $R^9$ is lower alkylcarbonyl, carboxy-lower alkylcarbonyl, arylcarbonyl, lower alkylsulphonyl, arylsulphonyl, lower alkoxycarbonyl or aryl-lower alkoxycarbonyl;

which process comprises treating an acetal of the formula

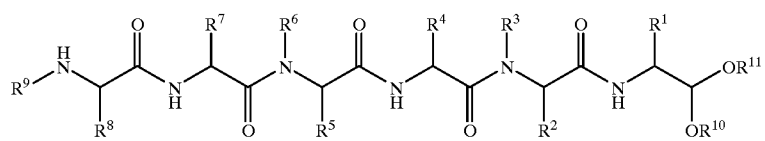

wherein any carboxy, hydroxy or aminocarbonyl group present in the acetal is protected, and $R^{10}$ and $R^{11}$ are each independently a lower alkyl; with a strong acid, thereby producing the compound. A further embodiment of this process comprises treating the compound of formula I as produced by the above process, wherein the compound is acidic, with a base, thereby producing a salt of the compound. In an embodiment of the process described above, the acetal of formula II is bonded to a solid phase peptide synthesis resin.

This invention provides process for producing a compound of the formula

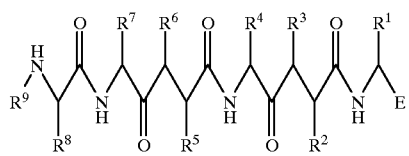

(I)

wherein
E is B(OH)$_2$
R$^1$ is lower alkyl, halo-lower alkyl, cyano-lower alkyl, lower alkylthio-lower alkyl, aryl-lower alkylthio-lower alkyl, aryl-lower alkyl, heteroaryl-lower alkyl, lower alkenyl or lower alkynyl;
R$^2$ is lower alkyl, hydroxy-lower alkyl, carboxy-lower alkyl, aryl-lower alkyl, aminocarbonyl-lower alkyl or lower cycloalkyl-lower alkyl; and
R$^3$ is hydrogen or lower alkyl; or
R$^2$ and R$^3$ together are di- or trimethylene optionally substituted by hydroxy;
R$^4$ is lower alkyl, hydroxy-lower alkyl, lower cycloalkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl or lower cycloalkyl;
R$^5$ is lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;
R$^6$ is hydrogen or lower alkyl;
R$^7$ is lower alkyl, hydroxy-lower alkyl, carboxy-lower alkyl, aryl-lower alkyl, lower cycloalkyl-lower alkyl or lower cycloalkyl;
R$^8$ represents lower alkyl, hydroxy-lower alkyl, carboxy-lower alkyl or aryl-lower alkyl; and
R$^9$ is lower alkylcarbonyl, carboxy-lower alkylcarbonyl, arylcarbonyl, lower alkylsulphonyl, arylsulphonyl, lower alkoxycarbonyl or aryl-lower alkoxycarbonyl;
which process comprises treating a substituted dioxaborolane of the formula wherein any carboxy, hydroxy or aminocarbonyl group present in the dioxaborolane is or is not protected, and Q is (a)

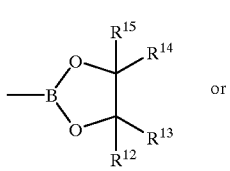

or (b)

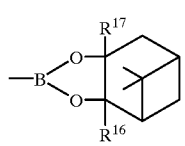

wherein R$^{12}$, R$^{13}$, R$^{14}$ and R$^{15}$ each are hydrogen or lower alkyl and R$^{16}$ and R$^{17}$ each are hydrogen or lower alkyl, with a strong acid when Q is (a) and with an alkali metal periodate when Q is (b) thereby producing the compound. A further embodiment of this process comprises treating the compound of formula I as produced by the above process, wherein the compound is acidic, with a base, thereby producing a salt of the compound. In an embodiment of the process described above, the acetal of formula II is bonded to a solid phase peptide synthesis resin.

More specifically, the compounds of formula I hereinbefore and salts of acidic compounds of formula I with bases are manufactured by a) for the manufacture of a compound of formula I in which E represents CHO, deacetalizing and, where required, deprotecting an acetal of the general formula (III)

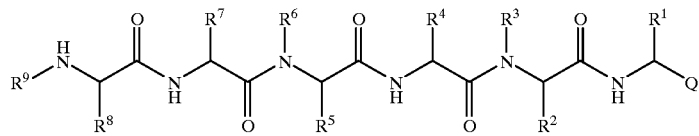

(II)

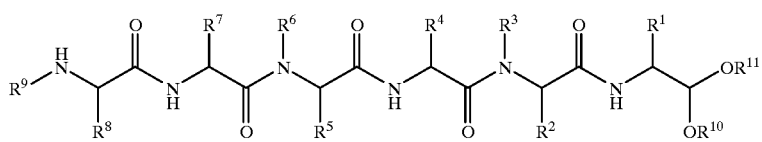

wherein $R^1$, $R^2$, $R^3$, $R^4$, $R^5$, $R^6$, $R^7$, $R^8$ and $R^9$ have the significance given earlier, provided that any carboxy, hydroxy and/or aminocarbonyl group(s) present is/are in protected form, and $R^{10}$ and $R^{11}$ each represent lower alkyl, or b) for the manufacture of a compound of formula I in which E represents $B(OH)_2$, ring opening and, where required, deprotecting a substituted dioxaborolane of the general formula

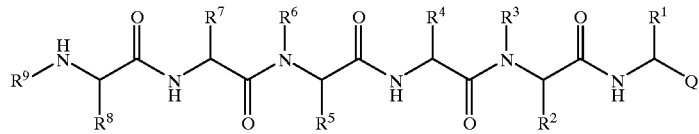

(III)

wherein $R^1$, $R^2$, $R^3$, $R^4$, $R^5$, $R^6$, $R^7$, $R^8$ and $R^9$ have the significance given earlier, provided that any carboxy, hydroxy and/or aminocarbonyl group(s) present may be in protected form, and Q represents a group of the formula

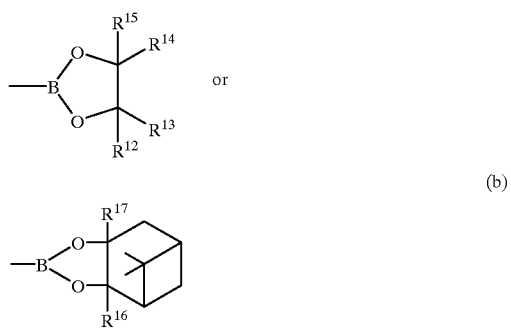

wherein $R^{12}$, $R^{13}$, $R^{14}$ and $R^{15}$ each represent hydrogen or lower alkyl and $R^{16}$ and $R^{17}$ each represent hydrogen or lower alkyl,
and c) if desired, converting an acidic compound of formula I obtained into a salt with a base.

Protected carboxy, hydroxy and aminocarbonyl groups which are present in the acetal starting materials of formula II and which may be present in the substituted dioxaborolane starting materials of formula III are carboxy, hydroxy and, respectively, aminocarbonyl groups protected with any conventional protecting group known from peptide chemistry. In particular, $R^2$, $R^4$, $R^7$, $R^8$ and/or $R^9$ can preferably represent tert-butoxycarbonyl-lower alkyl as protected carboxy, $R^2$, $R^4$, $R^5$, $R^7$ $R^8$ and/or $R^9$ can preferably represent lower alkyl O-tert.butyl ether as protected hydroxy and $R^2$ can preferably represent tritylaminocarbonyl-lower alkyl as protected aminocarbonyl-lower alkyl.

The deacetalization of an acetal of formula II, preferably one in which $R^{10}$ and $R^{11}$ each represent methyl, according to embodiment a) of the process according to the invention can be carried out using any conventional strong acid such as those described in T. W. Greene, P. G. M. Wuts, Protecting Groups in Organic Syntheses, 2nd edition, John Wiley & Sons 1991, in the presence of an inert organic solvent such as a halogenated aliphatic hydrocarbon, e.g. dichloromethane, and in the presence of water. Preferably the strong acid is trifluoroacetic acid or an equivalent strong acid Suitably, the deacetalization is carried out at about room temperature. When protected carboxy, hydroxy and/or aminocarbonyl groups are present in the acetal starting material, these are converted into free carboxy, hydroxy and/or aminocarbonyl groups under the conditions of the deacetalization.

According to a variant of embodiment a) of the process according to the invention, an acetal starting material of formula II is bonded to a solid phase peptide synthesis resin. In one embodiment the starting material is bonded to a solid phase peptide synthesis resin as described in Example 4. In this case, cleavage from the resin takes place under the conditions used for the deacetalization.

The ring opening of a substituted dioxaborolane of formula III in which Q represents a group of formula (a), preferably one in which $R^{12}$, $R^{13}$, $R^{14}$ and $R^{15}$ each represent methyl, according to embodiment b) of the process according to the invention can also be carried out using any conventional strong acid such as those described in T. W. Greene, P. G. M. Wuts, Protecting Groups in Organic Syntheses, 2nd edition, John Wiley & Sons 1991, in an inert organic solvent, e.g. a halogenated aliphatic hydrocarbon such as dichloromethane, and optionally in the presence of water. Preferably the strong acid is trifluoroacetic acid or an equivalent strong acid. Suitably, the ring opening is carried out at about room temperature. When protected carboxy, hydroxy and/or aminocarbonyl groups are present in the substituted dioxaborolane starting material, these are converted into free carboxy, hydroxy and/or aminocarbonyl groups under the conditions of the ring opening.

The ring opening of a substituted dioxaborolane of formula III in which Q represents a group of formula (b), especially one in which one of $R^{16}$ and $R^{17}$ represents hydrogen and the other represents methyl, according to embodiment b) of the process in accordance with the invention can be carried out in a conventional manner. Conveniently, the ring opening is carried out using any conventional periodate, especially an alkali metal periodate, especially sodium periodate in a buffered aqueous-organic medium, suitably at about room temperature. Advantageously, the medium consists of a mixture of an inert water-miscible organic solvent, e.g. acetone, and aqueous ammonium acetate. Any protected carboxy, hydroxy and/or aminocarbonyl group(s) present in the substituted dioxaborolane starting material are deprotected in a conventional manner known in tbe art e.g. by treatment with trifluoroacetic acid, prior to the ring opening.

According to a variant of embodiment b) of the process according to the invention, a substituted dioxaborolane of formula III in which Q represents a group of formula (a) is bonded to a solid phase synthesis resin. The bonding is typically through an alkyl group $R^{12}$, $R^{13}$, $R^{14}$ or $R^{15}$ linked to the resin via an amide bridge. Cleavage from the resin takes place under the conditions used in embodiment b) of the process.

In accordance with embodiment c) of the process acidic compounds of formula I can be converted into salts with bases, e.g. alkali metal salts such as sodium or potassium salts, alkaline earth metal salts such as calcium or magnesium salts, salts with organic bases, e.g. salts with amines such as N-ethylpiperidine, procaine or dibenzylamine, or salts with basic amino acids such as salts with arginine or lysine. The formation and isolation of such salts can be carried out according to conventional methods known in the art.

This invention provides acetal compounds of the formula

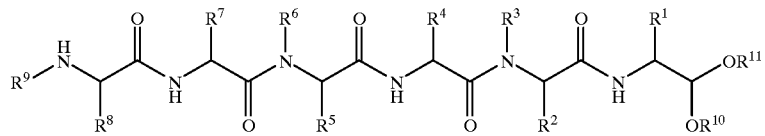

wherein $R^1$ is lower alkyl, halo-lower alkyl, cyano-lower alkyl, lower alkylthio-lower alkyl, aryl-lower alkylthio-lower alkyl, aryl-lower alkyl, heteroaryl-lower alkyl, lower alkenyl or lower alkynyl;

$R^2$ is lower alkyl, hydroxy-lower alkyl, carboxy-lower alkyl, aryl-lower alkyl, aminocarbonyl-lower alkyl or lower cycloalkyl-lower alkyl; and $R^3$ is hydrogen or lower alkyl; or $R^2$ and $R^3$ together are di- or trimethylene optionally substituted by hydroxy;

$R^4$ is lower alkyl, hydroxy-lower alkyl, lower cycloalkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl or lower cycloalkyl;

$R^5$ is lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;

$R^6$ is hydrogen or lower alkyl;

$R^7$ is lower alkyl, hydroxy-lower alkyl, carboxy-lower alkyl, aryl-lower alkyl, lower cycloalkyl-lower alkyl or lower cycloalkyl;

$R^8$ is lower alkyl, hydroxy-lower alkyl, carboxy-lower alkyl or aryl-lower alkyl;

$R^9$ is lower alkylcarbonyl, carboxy-lower alkylcarbonyl, arylcarbonyl, lower alkylsulphonyl, arylsulphonyl, lower alkoxycarbonyl or aryl-lower alkoxycarbonyl; and $R^{10}$ and $R^{11}$ are each independently a lower alkyl. Preferred values of $R^1$ through $R^9$ for compounds of formula II are as described above in connection with the compounds of formula I.

These acetal compounds can be prepared, for example, by firstly reducing a hydroxamate of the general formula

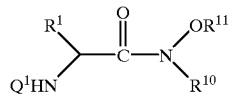

wherein $R^1$, $R^{10}$ and $R^{11}$ have the significance given earlier and $Q^1$ represents an amino protecting group, e.g. tert.butoxycarbonyl, with an alkali metal aluminium hydride, e.g. lithium aluminium hydride, treating the product with methanolic hydrochloric acid to give the hydrochloride salt of a compound of the formula

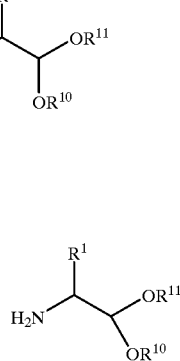

wherein $R^1$, $R^{10}$ and $R^{11}$ have the significance given earlier, and subsequently either subjecting this to sequential coupling with respective amino acids or subjecting a fragment obtained during such a sequential coupling to further coupling with a peptide derivative of appropriate length. Alternatively, a compound of formula V can be coupled with a suitable pentapeptide.

The aforementioned coupling reactions can be carried out in a manner known per se in peptide chemistry, conveniently using the respective amino acid or di, tri-, tetra- or pentapeptide appropriately protected as described above and also at any amino group present by Fmoc [(9-fluorenyl) methoxycarbonyl] in the presence of hydroxybenzotriazole, 1-(3-dimethylaminopropyl)-3-ethylcarbodiimide hydrochloride and N-methylmorpholine and in an inert organic solvent, e.g. a halogenated hydrocarbon such as dichloromethane.

The hydroxamates of formula IV required for the preparation of the acetal starting materials of formula II are known compounds or analogues of known compounds which can be prepared in an analogous manner to the known compounds.

The acetal starting materials of formula II can also be synthesised from a compound of formula V on a solid phase peptide synthesis resin. This procedure is known and is described in detail in Handbook from Fourth International Symposium on Solid Phase Synthesis and Combinatorial Chemical Libraries, Edinburgh, 1995.

This invention provides dioxaborolanes of formula

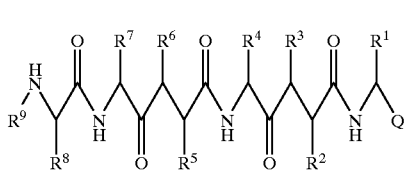
(III)

wherein
$R^1$ is lower alkyl, halo-lower alkyl, cyano-lower alkyl, lower alkylthio-lower alkyl, aryl-lower alkylthio-lower alkyl, aryl-lower alkyl, heteroaryl-lower alkyl, lower alkenyl or lower alkynyl;
$R^2$ is lower alkyl, hydroxy-lower alkyl, carboxy-lower alkyl, aryl-lower alkyl, aminocarbonyl-lower alkyl or lower cycloalkyl-lower alkyl; and
$R^3$ is hydrogen or lower alkyl; or
$R^2$ and $R^3$ together are di- or trimethylene optionally substituted by hydroxy;
$R^4$ is lower alkyl, hydroxy-lower alkyl, lower cycloalkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl or lower cycloalkyl;
$R^5$ is lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;
$R^6$ is hydrogen or lower alkyl;
$R^7$ is lower alkyl, hydroxy-lower alkyl, carboxy-lower alkyl, aryl-lower alkyl, lower cycloalkyl-lower alkyl or lower cycloalkyl;
$R^8$ is lower alkyl, hydroxy-lower alkyl, carboxy-lower alkyl or aryl-lower alkyl; and
$R^9$ is lower alkylcarbonyl, carboxy-lower alkylcarbonyl, arylcarbonyl, lower alkylsulphonyl, arylsulphonyl, lower alkoxycarbonyl or aryl-lower alkoxycarbonyl; and
Q is

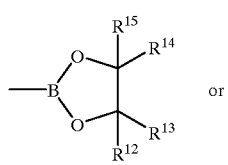
(a)

or

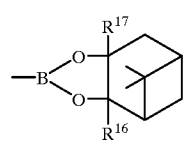
(b)

wherein $R^{12}$, $R^{13}$, $R^{14}$ and $R^{15}$ each are hydrogen or lower alkyl and $R^{16}$ and $R^{17}$ each are hydrogen or lower alkyl, and wherein any carboxy, hydroxy or aminocarbonyl group present in the dioxoborolane is or is not protected. Preferred values of $R^1$ through $R^9$ for the compounds of formula III are as described above for compounds of formula I. These dioxaborolanes, which include the substituted dioxaborolanes of formula III used as starting materials in embodiment b) of the process according to the invention can be prepared, for example, as illustrated in Scheme A hereinafter in which $R^1$ and Q have the significance given earlier:

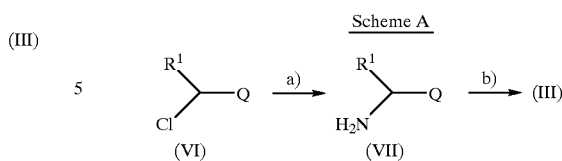

Scheme A

Having regard to Scheme A, in step a) a compound of formula VI is reacted with an alkali metal bis[tri(lower alkyl)silyl]amide, e.g. lithium bis(trimethylsilyl)amide, in an inert organic solvent such as an ether, e.g. diethyl ether or tetrahydrofuran, and then treated with a strong acid, e.g. trifluoroacetic acid, to give a compound of formula VII.

In step b) a compound of formula VII is converted into a compound of formula III either by coupling with a pentapeptide, by sequential coupling with respective amino acids or by coupling a fragment obtained during the sequential coupling with a peptide derivative of the desired length, with the amino acid or peptide used being appropriately protected as described above and also at any amino group present by Fmoc. These coupling reactions can be carried out in a manner known per se in peptide chemistry, for example using the amino acid or peptide in the form of a mixed anhydride formed e.g. with a lower alkyl haloformate such as isobutyl chloroformate and carrying out the coupling in the presence of a suitable base, e.g. a tertiary organic base such as N-methylmorpholine.

Substituted dioxoborolanes of formula III obtained by the foregoing coupling and which carry a protecting group on the substituent at $R^2$, $R^4$, $R^5$, $R^7$, $R^8$ and/or $R^9$ can be selectively deprotected in a conventional manner, e.g. using trifluoroacetic acid, to the corresponding compounds which carry a free carboxy, hydroxy and/or aminocarbonyl group on the respective substituent, while retaining the protected boronic acid moiety denoted by Q. These selectively deprotected compounds are also active as inhibitors of proteinases of viral origin and can be used in the treatment of viral infections in the same manner as the compounds of formula I Compounds of formula VI can be prepared, for example, from a compound of the general formula

wherein Q has the significance given earlier, which is a known compound or an analogue of a known compound, by reaction with a compound of the formula $R^{1a}$-MgHal, wherein $R^{1a}$ has the same significance as $R^1$ hereinbefore, but contains one carbon atom less and Hal represents halogen, preferably bromine. The reaction is carried out under the conventional conditions of a Grignard reaction, for example in an inert organic solvent such as an ether, e.g. diethyl ether or tetrahydrofuran. When Q represents a group of formula (b), the reaction is carried out in the presence of zinc chloride.

A compound of formula VI in which $R^1$ represents bromo-lower alkyl or fluoro-lower alkyl and Q represents a group of formula (a) can be prepared, for example, by hydroborating a bromo- or fluoro-lower alkene, e.g. 3-bromopropene or 3-fluoropropene, reacting the hydroboration product with a diol of the formula $R^{12}R^{13}C(OH)$—

C(OH)R$^{14}$R$^{15}$, wherein R$^{12}$, R$^{13}$, R$^{14}$ and R$^{15}$ have the significance given earlier, e.g. 2,3-dimethyl-2,3-butanediol, and reacting the resulting 2-(bromo- or fluoro-lower alkyl)-1,3,2-dioxaborolane with dichloromethane in the presence of lithium diisopropylamine. The hydroboration can be carried out in a conventional manner, for example using phenylboronic acid at an elevated temperature, e.g. about 100° C., in the absence of a solvent or using borane-dimethyl sulphide complex in the presence of cyclohexene in an inert organic solvent, e.g. dimethoxyethane, at about 0° C. followed by treatment with trimethylamine N-oxide.

A substituted dioxoborolane of formula III in which Q represents a group of formula (a) can also be synthesised on a solid phase peptide synthesis resin. For example, a 4-methylbenzhydryl resin can be reacted with a dioxoborolanyl-valeric acid of the general formula

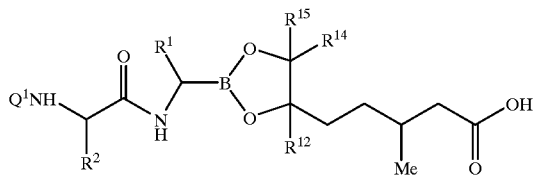
(IX)

wherein R$^{1}$, R$^{2}$, R$^{12}$, R$^{14}$, R$^{15}$ and Q$^{1}$ have the significance given earlier, and the product can be converted into the required resin-bonded starting material by successive deprotection and coupling with a protected amino acid.

Compounds of formula IX can be conveniently prepared by reacting a tert-butyl 6,7-dihydroxy-3,6,7-tri(lower alkyl)-6-octenoate with dichloromethyl diisopropoxyborane, condensing the resulting compound of the general formula

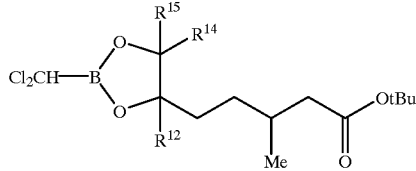
(X)

wherein R$^{12}$, R$^{14}$ and R$^{15}$ have the significance given earlier, with a compound of formula R$^{1}$MgHal, wherein R$^{1}$ has the significance given earlier and Hal represents halogen, preferably bromine, under the conditions of a Grignard reaction, reacting the resulting compound of the general formula

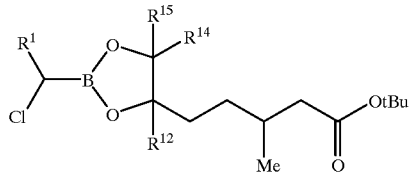
(XI)

wherein R$^{1}$, R$^{12}$, R$^{14}$ and R$^{15}$ have the significance given earlier, with an alkali metal bis[tri(lower alkyl)silyl]amide, condensing the resulting compound of the general formula

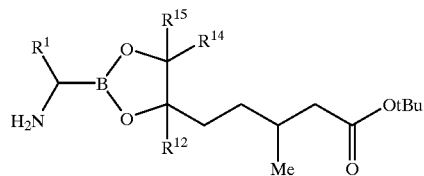
(XII)

wherein R$^{1}$, R$^{12}$, R$^{14}$ and R$^{15}$ have the significance given earlier, with a protected amino acid of the general formula

Q$^{2}$HN—CH(R$^{2}$)—COOH (XIII)

wherein R$^{2}$ has the significance given earlier and Q$^{2}$ represents Fmoc, and de-esterifying the resulting compound of the general formula

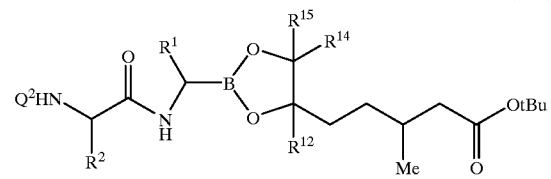
(XIII)

wherein R$^{1}$, R$^{2}$, R$^{12}$, R$^{14}$, R$^{15}$ and Q$^{2}$ have the significance given earlier.

As mentioned earlier, the compounds of formula I and salts of acidic compounds of formula I with bases are inhibitors of proteases of viral origin. The activity against one such protease, namely HCV protease, can be demonstrated using the following assay:

Construction of plasmid for the expression of MBP-NS3"Gly$_{12}$-NS4A enzyme in *E. coli*

The nucleotide sequence of this expression plasmid is given in FIG. 1 appended hereto and the amino acid sequence of its expression product is given in FIG. 2 appended hereto. It is based on the pMAL®-c2 vector supplied by New England Biolabs, Inc. (32 Tozer Rd., Beverly, Mass., USA). The principle of the construction was to create an in-frame fusion of the maltose binding protein (MBP) gene supplied by the pMAL-c2 vector, and sequences of the HCV genome necessary for NS3 proteinase activity. These HCV sequences were inserted between the EcoRI and HindIII sites of the pMAL-c2 polylinker (positions 2695 and 3556 respectively of the sequence given in FIG. 1).

HCV sequences were derived from plasmids pDS 3348–4045 and pBFK 3348–6062, described by Bartenschlager et al, 1993 (Journal of Virology, 67, 3835–3844). Regions encompassing the NS3 proteinase domain (amino acids 1007–1219) and the NS4A domain (amino acids 1658–1711) were isolated and inserted into the pMAL-c2 vector using standard recombinant DNA techniques, including the PCR amplification of required sequences. Between the NS3 and NS4A domains, a linker region was constructed using synthetic oligonucleotides (positions 3343–3390; amino acids 606–621). The resulting plasmid was used to transform *E. coli* (strain MC1061) cells and expression of the MBP-NS3"Gly$_{12}$-NS4A enzyme was induced as described below.

Protein expression and purification

E. coli (strain MC1061) cells transformed with the foregoing plasmid were grown in Luria broth containing ampicillin (100 μg/ml) at 37° C. The cells were grown until an optical density of 0.5 at 600 nm had been reached and enzyme expression was then induced by adding 1 mM isopropylthiogalactoside and incubating at 37° C. for a further 3 hours. The cells were harvested by centrifugation and stored at −80° C.

A pellet from 4 l of bacterial culture was resuspended in E. coli lysis buffer (20 mM Tris HCl, pH 7.5, containing 150 mM NaCl, 1 mM EDTA and 10 mM dithiothreitol) and cell lysis was achieved by two passages through a French Pressure cell. The clear supernatant obtained by centrifugation (18000 g, 30 minutes) was then applied to an amylose resin column (4×1 cm) (New England Biolabs) which had been equilibrated with ice-cold 50 mM Tris HCl, pH 8.5, containing 200 mM NaCl, 1 mM dithiothreitol and 5% glycerol. The column was washed thoroughly with the equilibration buffer and bound protein was eluted using the equilibration buffer containing 10 mM maltose. Fractions of 1 ml were collected, with fractions containing the enzyme being pooled and stored at −80° C. Enzyme concentration was assayed by the method of M. B. Bradford, Analytical Biochemistry, 1976, vol. 72, p. 248.

Assay

Compounds of formula I (routinely prepared as stock solutions in DMSO) were assayed for their ability to inhibit the cleavage of a quenched fluorescence substrate [NS4A/B.F peptide (N-[4-[4-(dimethylamino)phenylazo]benzoyl]-L-α-aspartyl-L-α-glutamyl-L-methionyl-L-α-glutamyl-L-α-glutamyl-L-cysteinyl-L-alanyl-L-seryl-L-histidyl-N5-[2-(5-sulpho-1-naphthylamino)ethyl]-L-glutaminamide); Wilkinson et al, Society for General Microbiology Meeting, University of Warwick, England, 28 March 1996] based on the NS4A/4B cleavage site by enzyme MBP-NS3"Gly$_{12}$-NS4A in microtitre plates as follows:

The enzyme (1 μg) was added to 200 μl final volume of a mixture containing 50 mM Tris HCl, pH 8.5, with 1 mM dithiothreitol, 0.1% Triton X-100 and the test compound of formula 1. The resulting mixture was incubated at room temperature for 15 minutes prior to starting the reaction by the addition of NS4A/B.F peptide to a final concentration of 10 μM. The progress of the reaction was evaluated with a Perseptive Biosystems Cytofluor II using an excitation wavelength of 360 nm and an emission wavelength of 530 nm. After incubation for a further 10 minutes, the reduction in fluorescence in the presence of inhibitor was measured. This was plotted against inhibitor concentration and the inhibitor concentration which caused 50% reduction (IC$_{50}$) was calculated by manual graphical analysis or by the use of the Perseptive Biosystems Cytocalc curve fitting program.

The results obtained in the foregoing assay with representative compounds of formula I are compiled in the following Table:

TABLE

| Compound of formula I | HCV proteinase IC$_{50}$ (μmol/l) |
|---|---|
| A | 0.09 |
| B | 0.07 |
| C | 0.064 |
| D | 0.034 |
| E | 0.038 |
| F | 0.16 |

Compounds:
A=2(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-pentenaldehyde.
B=2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4,4-difluorovaleraldehyde.
C=2(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4,4,4-trifluorobutyraldehyde.
D=1(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-3-butenylboronic acid.
E=1(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]propylboronic acid.
F=1(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]butylboronic acid.

The compounds of formula I and salts of acidic compounds of formula I with bases can be used as medicaments, e.g. in the form of pharmaceutical preparations. The pharmaceutical preparations can be administered enterally such as orally in the form of tablets, coated tablets, dragées, hard and soft gelatine capsules, solutions, emulsions or suspensions, nasally, e.g. in the form of nasal sprays, or rectally, e.g. in the form of suppositories. They may, however, also be administered parenterally, e.g. in the form of injection solutions. In one embodiment, this invention provides a pharmaceutical composition comprising from ten to five hundred milligrams of a compound of each of the embodiments of compounds of formula I described above, and a compatible pharmaceutical carrier.

The compounds of formula I and their aforementioned salts can be processed with pharmaceutically inert, organic or inorganic carriers for the production of pharmaceutical preparations. Lactose, corn starch or derivatives thereof, talc, stearic acid or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like; depending on the nature of the active ingredient no carriers are, however, usually required in the case of soft gelatine capsules. Suitable carriers for the production of solutions and syrups are, for example, water, polyols, sucrose, invert sugar, glucose and the like. Suitable carriers for suppositories are, for example, natural or hardened oils, waxes, fats, semi-liquid or liquid polyols and the like.

The pharmaceutical preparations can also contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a salt of an acidic compound of formula I with a base in association with a compatible pharmaceutical carrier are also an object of the present invention, as is a process for the production of such medicaments which comprises bringing one or more of these compounds or salts and, if desired, one or more other therapeutically valuable substances into a galenical administration form together with a compatible pharmaceutical carrier.

As mentioned earlier, the compounds of formula I and salts of acidic compounds of formula I with bases can be used in accordance with the invention as therapeutically active substances, especially as antiviral agents. The dosage can vary within wide limits and will, of course, be fitted to the individual requirements in each particular case. In general, in the case of administration to adults a convenient daily dosage should be about 3 mg to about 3 g, preferably about 10 mg to 1 g. The daily dosage may be administered as a single dose or in divided doses and, in addition, the upper dosage limit referred to earlier may be exceeded when this is found to be indicated.

Finally, the use of compounds of formula I and salts of acidic compounds of formula I with bases for the production of medicaments, especially of antiviral medicaments, is also an object of the invention.

The invention is illustrated by the following Examples. In the Examples SSA denotes the solvent system 0.1% TFA in water and SSB denotes the solvent system 0.1% TFA in 70% acetonitrile 30% water.

EXAMPLE 1

0.1 g (0.1 mmol) of N2-[N-[N-[N-[3-(tert-butoxycarbonyl)-propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)propyl]-L-leucinamide was dissolved in 3 ml of dichloromethane, 3 ml of trifluoroacetic acid and 90 mg of water and the mixture was stirred at room temperature for 30 minutes. The solution was diluted with 20 ml of toluene and the solvent was removed by evaporation. The resulting white solid was triturated with diethyl ether and filtered off. The solid was purified by RP-HPLC on a C18 Dynamax column (pore size 300 Å; column size 21.4 mm×50 mm). The elution gradient comprised 90% SSA 10% SSB to 95% SSB 5% SSA over 8.5 minutes. After lyophilization overnight there were obtained 25 mg of 2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino] butyraldehyde as a white foam. MS: m/e 819.5 [M+H]+.

The starting material was prepared as follows:
i) A solution of 25 g (63.6 mmol) of L-leucine benzyl ester p-toluenesulphonic acid salt, 14.69 g (63.6 mmol) of N-(tert-butoxycarbonyl)-3-methyl-L-valine, 9.73 g (63.6 mmol) of 1-hydroxybenzotriazole, 7.32 g (63.3 mmol) of N-ethylmorpholine and 12.21 g (63.6 mmol) of 1-(3-dimethylaminopropyl)-3-ethylcarbodiimide hydrochloride in 500 ml of dichloromethane was stirred at room temperature overnight. The solution was washed with water, sodium hydrogen carbonate solution, 2M hydrochloric acid and saturated sodium chloride solution and dried over anhydrous magnesium sulphate. Evaporation gave 21.65 g of N-[(N-tert-butoxycarbonyl)-3-methyl-L-valyl]-L-leucine benzyl ester as an oil which was used in the next step without further purification. MS: m/e 435 [M+H]+.

ii) A solution of 9.74 g (22.4 mmol) of N-[(N-tert-butoxycarbonyl)-3-methyl-L-valyl]-L-leucine benzyl ester in 25 ml of trifluoroacetic acid and 50 ml of dichloromethane was stirred at room temperature for 30 minutes. The solvent was removed by evaporation and 50 ml of toluene were added. Evaporation gave N-( 3-methyl-L-valyl)-L-leucine benzyl ester as an oil which was used in the next step without further purification.

iii) A solution of the foregoing oil, 9g (22.4 mmol) of N-(9-fluorenylmethoxycarbonyl)-2-methyl-L-phenylalanine, 3.43 g (22.4 mmol) of 1-hydroxybenzotriazole, 3.87 g (33.66 mmol) of N-ethylmorpholine and 4.31 g (22.4 mmol) of 1-(3-dimethylaminopropyl)-3-ethylcarbodiimide hydrochloride in 100 ml of dichloromethane was stirred at room temperature overnight. The solution was washed with water, sodium hydrogen carbonate solution, 2M hydrochloric acid and saturated sodium chloride solution and dried over anhydrous magnesium sulphate. Evaporation and chromatography on silica gel using 30% ethyl acetate in petroleum ether (b.p. 40–60° C.) for the elution gave 12.32 g of N-[N-[N-[(9-fluorenyl) methoxycarbonyl]-2-methyl-L-phenylalanyl]-3-methyl-L-valyl]-L-leucine benzyl ester as an oil. MS: m/e 718 [M+H]+.

iv) A solution of 10 g (13.95 mmol) of N-[N-[N-[(9-fluorenyl)-methoxycarbonyl]-2-methyl-L-phenylalanyl]-3-methyl-L-valyl]-L-leucine benzyl ester in 30 ml of piperidine and 120 ml of dichloromethane was stirred for 30 minutes at room temperature. The solvent was removed by evaporation and the residue was chromatographed on silica gel using firstly 20% ethyl acetate in hexane and then 10% methanol in dichloromethane for the elution. Evaporation gave 6.9 g of N-[N-[2-methyl-L-phenylalanyl]-3-methyl-L-valyl]-L-leucine benzyl ester in the form of an oil which was used in the next step without further purification.

v) A solution of 6.9 g of the foregoing oil, 2.13 g (13.95 mmol) of 1-hydroxybenzotriazole, 2.68 g (13.95 mmol) of 1-(3-dimethylaminopropyl)-3-ethylcarbodiimide hydrochloride and 5.93 g (13.95 mmol) of N-[(9-fluorenyl) methoxycarbonyl]-O-tert.-butyl-L-α-glutamic acid in 150 ml of dichloromethane was stirred at room temperature overnight. The solution was washed with water, sodium hydrogen carbonate solution, 2M hydrochloric acid and saturated sodium chloride solution and dried over anhydrous magnesium sulphate. Evaporation and chromatography of the residue on silica gel using 30% ethyl acetate in petroleum ether (b.p. 40–60° C.) for the elution gave 10.89 g of N-[N-[N-[(9-fluorenyl)-methoxycarbonyl]-O-tert-butyl-L-α-glutamyl]-2-methyl-L-phenylalanyl]-3-methyl-L-valyl]-L-leucine benzyl ester as a thick oil. MS: m/e 903 [M+H]+.

vi) A solution of 10.89 g (12.07 mmol) of N-[N-[N-[(9-fluorenyl)methoxycarbonyl]-O-tert-butyl-L-α-glutamyl]-2-methyl-L-phenylalanyl]-3-methyl-L-valyl]-L-leucine benzyl ester in 30 ml of piperidine and 120 ml of dichloromethane was stirred for 30 minutes at room temperature. The solvent was removed by evaporation and the residue was chromatographed on silica gel using firstly 20% ethyl acetate in hexane and then 10% methanol in dichloromethane for the elution. Evaporation gave N-[N-[N-[O-tert-butyl-L-α-glutamyl]-2-methyl-L-phenylalanyl]-3-methyl-L-valyl]-L-leucine benzyl ester in the form of an oil which was used in the next step without further purification.

vii) A solution of the foregoing oil, 4.96 g (12.07 mmol) of N-[(9-fluorenyl)methoxycarbonyl]-O-tert-butyl-L-α-aspartic acid, 1.85 g (12.07 mmol) of 1-hydroxybenzotriazole and 2.32 g (12.07 mmol) of 1-(3-dimethylaminopropyl)-3-ethylcarbodiimide hydrochloride in 100 ml of dichloromethane was stirred at room temperature overnight. The solution was washed with water, sodium hydrogen carbonate solution, 2M hydrochloric acid and saturated sodium chloride solution and dried over anhydrous magnesium sulphate. Evaporation and chromatography of the residue on silica gel using ethyl acetate for the elution gave 10.088 g of N-[N-[N-[N-[N-[(9-fluorenyl)methoxycarbonyl]-O-tert-butyl-L-α-aspartyl]-O-tert-butyl-L-α-glutamyl]-2-methyl-L-phenylalanyl]-3-methyl-L-valyl]-L-leucine benzyl ester as a white solid. MS: m/e 1074 [M+H]$^+$.

viii) A solution of 10.088 g (9.4 mmol) of N-[N-[N-[N-[(9-fluorenyl)methoxycarbonyl] O-tert-butyl-L-α-aspartyl]-O-tert-butyl-L-α-glutamyl]-2-methyl-L-phenylalanyl]-3-methyl-L-valyl]-L-leucine benzyl ester in 30 ml of piperidine and 120 ml of dichloromethane was stirred for 30 minutes at room temperature. The solvent was removed by evaporation and the residue was chromatographed on silica gel using firstly 20% ethyl acetate in hexane and then 10% methanol in dichloromethane for the elution. Evaporation gave N-[N-[N-[N-[O-tert-butyl-L-α-aspartyl]-O-tert-butyl-L-α-glutamyl-2-methyl-L-phenylalanyl]-3-methyl-L-valyl]-L-leucine benzyl ester in the form of an oil which was used in the next step without further purification.

ix) A solution of 8 g of the foregoing oil, 1.64 g (9.4 mmol) of tert-butyl hydrogen succinate, 1.44 g (9.4 mmol) of 1-hydroxybenzotriazole and 1.805 g (9.4 mmol) of 1-(3-dimethylaminopropyl)-3-ethylcarbodiimide hydrochloride in dichloromethane was stirred at room temperature overnight. The solution was washed with water, sodium hydrogen carbonate solution, 2M hydrochloric acid and saturated sodium chloride solution and dried over anhydrous magnesium sulphate. Evaporation and trituration of the residue with acetone gave 6.87 g of N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine benzyl ester as a white solid. MS: m/e 1008.6 [M+H]$^+$, m/e 1030.3 [M+Na]$^+$.

x) A solution of 6.8 g (6.75 mmol) of N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine benzyl ester in 200 ml of dimethylformamide was hydrogenated over 600 mg of 10% palladium/carbon for 1 hour. The catalyst was removed by filtration and the filtrate was evaporated to give 15 g of crude product which was chromatographed on silica gel using 10–15% methanol in dichloromethane for the elution to give 6 g of N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine as a white solid of melting point 235–236° C.; MS: m/e 918.4 [M+H]$^+$, m/e 940.3 [M+Na]$^+$.

xi) 370 mg (2.5 mmol) of N,O-dimethyl 2(S)-(tert-butoxyformamido)butyrohydroxamate were dissolved in 20 ml of anhydrous tetrahydrofuran under nitrogen and the solution was cooled to 0° C. in an ice-bath. 1.5 ml (1.5 mmol) of 1M lithium aluminium hydride in tetrahydrofuran were added and the mixture was stirred at 0° C. for 10 minutes. 20 ml of saturated aqueous potassium hydrogen sulphate were added and the mixture was stirred vigorously under nitrogen for 30 minutes at room temperature. The mixture was then diluted with 50 ml of diethyl ether and the organic layer was separated, dried over anhydrous magnesium sulphate and the solvent was evaporated. The residue was dissolved in 10 ml of a saturated methanolic hydrogen chloride solution, stirred for 1 hour, then diluted with 50 ml of toluene and evaporated to dryness. The resulting oil was dissolved in 10 ml of dichloromethane and 184 mg (0.2 mmol) of N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine, 58 mg (0.3 mmol) of 2-(3-dimethylaminopropyl-3-ethylcarbodiimide hydrochloride, 41 mg (0.3 mmol) of 1-hydroxy-7-azabenzotriazole and 350 mg (3.0 mmol) of N-ethylmorpholine were added. The mixture was stirred for 30 minutes then washed in sequence with saturated sodium bicarbonate solution and 2M hydrochloric acid and dried over anhydrous magnesium sulphate. The solution was evaporated to dryness and the residue was chromatographed on silica gel using 4% methanol in dichloromethane for the elution. After trituration with diethyl ether there were obtained 110 mg of N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)propyl]-leucinamide as a white solid of melting point 242–244° C. MS: m/e 1001.5 [M+H–MeOH]$^+$, m/e 1055 [M+Na]$^+$.

Analysis for $C_{53}H_{88}O_{14}N_6$ [1033.315]. Calculated: C, 61.61; H, 8.58; N, 8.13% Found: C, 61.52, H, 8.45; N, 8.19%

EXAMPLE 2

70 mg (0.067 mmol) of N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N 1-[1(S)-(dimethoxymethyl)-3-butynyl]-L-leucinamide were stirred in a mixture of 4 ml of trifluoroacetic acid, 4 ml of dichloromethane and 30 mg of water at room temperature for 30 minutes. The solution was evaporated to dryness in a vacuum and the residue was chromatographed on silica gel using dichloromethane/methanol/acetic acid/water (60:13:2:2) for the elution. There were obtained 36 mg of 2(RS)-[[N-[N-[N-[N-[(3-carboxypropionyl)-L-α-aspartyl]-L-α-glutamyl]-2-methyl-L-phenylalanyl]-3-methyl-L-valyl]-L-leucyl]amino]-4-pentynal (9:1 mixture of diastereoisomers) as a white solid. MS: m/e 829.6 [M+H]$^+$.

The starting material was prepared as follows:

i) A solution of 12.17 g (57.14 mmol) of N-(tert-butoxycarbonyl)-1(S)-amino-4-pentynoic acid, 8.74 g (64.74 mmol) of hydroxybenzotriazole, 6.96 g (71.43 mmol) of N,O-dimethylhydroxylamine, 8.21 g (71.43 mmol) of N-ethylmorpholine and 13.7 g (71.43 mmol) of 1-(3-dimethylaminopropyl)-3-ethylcarbodiimide hydrochloride in 250 ml of dichloromethane was stirred for 18 hours, then washed with 2M hydrochloric acid and saturated sodium bicarbonate solution, dried and evaporated to give 14.2 g of N,O-dimethyl 2(S)-(tert-butoxyformamido)-4-pentynohydroxamate as a viscous gum which slowly crystallized.

Analysis for $C_{12}H_{20}N_2O_4$ [256.3021. Calculated: C, 56.24; H, 7.87; N, 10.93% Found: C, 56.01, H, 7.81; N, 10.92% ii) 10 ml (10 mmol) of 1M lithium aluminium hydride in tetrahydrofuran were added to a solution of 3.15 g (12.3 mmol) of N,O-dimethyl 2(S)-(tert-butoxyformamido)-4-pentynohydroxamate in 50 ml of dry tetrahydrofuran at 0° C.

under a nitrogen atmosphere. The solution was stirred for 20 minutes and then 40 ml of saturated potassium hydrogen sulphate solution were added dropwise. The mixture was stirred for 15 minutes and then diluted with diethyl ether. The organic layer was dried over magnesium sulphate and evaporated to give an oil which was dissolved in 50 ml of methanolic hydrogen chloride solution. The solution was left at room temperature for 1 hour and then evaporated to dryness to give a dark brown gum. 1.05 g of the gum were added to a solution of 2.06 g (5.84 mmol) of N-[(9-fluorenyl)methoxycarbonyl]-L-leucine, 867 mg (6.42 mmol) of hydroxybenzotriazole, 1.233 g (6.42 mmol) of 1-(3-dimethylaminopropyl)-3-ethylcarbodiimide hydrochloride and 2.216 g (19.27 mmol) of N-ethylmorpholine in 40 ml of dichloromethane. The solution was stirred at room temperature for 18 hours, washed with 2M hydrochloric acid and saturated sodium bicarbonate solution, dried over magnesium sulphate and evaporated to give a gum which was chromatographed on silica gel using ethyl acetate/petrol (2:3) for the elution. There were obtained 1.1 g of N2-[(9-fluorenyl)methoxycarbonyl]-N1-[1(S)-(dimethoxymethyl)-3-butynyl]-L-leucinamide as an off-white solid. $^1$H NMR (400 MHz, DMSO-d$_6$) δ: 0.86 (6H,dd), 1.35–1.65 (3H,m), 2.22–2.39 (2H,m), 2.75(1H,t), 3.22 (3H,s), 3.27 (3H,s), 3.91 (1H,m), 4.08 (1H,m), 4.15–4.3 (4H,m), 7.29 (2H,m), 7.4 (2H,t), 7.42 (1H,d), 7.71 (2H,d), 7.84 (1H,d), 7.88 (2H,d).

iii) 525 mg (1.1 mmol) of N2-[(9-fluorenyl)methoxycarbonyl]-N1-[1(S)-(dimethoxymethyl)-3-butynyl]-L-leucinamide were dissolved in 20 ml of dichloromethane and 5 ml of piperidine and the mixture was stirred at room temperature for 30 minutes. The mixture was evaporated to dryness and the residue was chromatographed on silica gel using firstly ethyl acetate/petrol (1:1) and then methanol/dichloromethane (1:9) for the elution. Evaporation of the dichloromethane solution gave a gum which was added to a solution of 363 mg (1.03 mmol) of N-[(9-fluorenyl)methoxycarbonyl]-3-methyl-L-leucine, 149 mg (1.1 mmol) of hydroxybenzotriazole and 288 mg (1.5 mmol) of 1-(3-dimethylaminopropyl)-3-ethylcarbodiimide hydrochloride in 15 ml of dichloromethane. The mixture was stirred for 18 hours, then washed with 2M hydrochloric acid and saturated sodium bicarbonate solution, dried over magnesium sulphate and evaporated to dryness. The residue was chromatographed on silica gel using ethyl acetate/petrol (1:2) for the elution to give 501 mg of N2-[N-[(9-fluorenyl) methoxycarbonyl]-3-methyl-L-valyl]-N1-[1(S)-(dimethoxymethyl)-3-butynyl]-L-leucinamide as a white foam. MS: m/e 592.3 [M+H]$^+$, 560.3 [M+H−MeOH]$^+$.

iv) 490 mg (0.83 mmol) of N2-[N-[(9-fluorenyl) methoxycarbonyl]-3-methyl-L-valyl]-N1-[1(S)-(dimethoxymethyl)-3-butynyl]-L-leucinamide were dissolved in 16 ml of dichloromethane and 4 ml of piperidine and the mixture was stirred at room temperature for 30 minutes. The mixture was evaporated to dryness and the residue was chromatographed on silica gel using firstly ethyl acetate/petrol (1:1) and then methanol/dichloromethane (1:9) for the elution. Evaporation of the dichloromethane solution gave a gum which was added to a solution of 321 mg (0.8 mmol) of N-[(9-fluorenyl)methoxycarbonyl]-2-methyl-L-phenylalanine, 122 mg (0.9 mmol) of hydroxybenzotriazole and 192 mg (1 mmol) of 1-(3-dimethylaminopropyl)-3-ethylcarbodiimide hydrochloride in 15 ml of dichloromethane. The mixture was stirred for 18 hours, then washed with 2M hydrochloric acid and saturated sodium bicarbonate solution, dried over magnesium sulphate and evaporated to dryness. The residue was chromatographed on silica gel using ethyl acetate/petrol (2:3) for the elution to give a white foam which was dissolved in 16 ml of dichloromethane and 4 ml of piperidine and left at room temperature for 30 minutes. The mixture was evaporated to dryness and the residue was chromatographed on silica gel using firstly ethyl acetate/petrol (1:1) and then methanol/dichloromethane (1:9) for the elution. Evaporation of the dichloromethane solution gave a gum which was added to a solution of 213 mg (0.5 mmol) of N-[(9-fluorenyl)methoxycarbonyl]-O-tert-butyl-L-α-glutamic acid, 74 mg (0.55 mmol) of hydroxybenzotriazole and 115 mg (0.6 mmol) of 1-(3-dimethylaminopropyl)-3-ethylcarbodiimide hydrochloride in 10 ml of dichloromethane. The mixture was stirred for 18 hours, then washed with 2M hydrochloric acid and saturated sodium bicarbonate, dried over magnesium sulphate and evaporated to dryness. Trituration of the residue with diethyl ether gave 345 mg of N2-[N-[N-[O-tert-butyl-N-[(9-fluorenyl)methoxycarbonyl]-L-α-glutamyl]-2-methyl-L-phenylalanyl]-3-methyl-L-valyl]-N1-[1(S)-(dimethoxymethyl)-3-butynyl]-leucinamide as a white solid. MS: m/e 938 [M+H]$^+$, 906 [M+H−MeOH]$^+$.

v) 340 mg (0.36 mmol) of N2-[N-[N-[O-tert-butyl-N-[(9-fluorenyl)methoxycarbonyl]-L-α-glutamyl]-2-methyl-L-phenylalanyl]-3-methyl-L-valyl]-N1-[1(S)-(dimethoxymethyl)-3-butynyl]-L-leucinamide were dissolved in 12 ml of dichloromethane and 3 ml of piperidine and the mixture was stirred at room temperature for 30 minutes. The mixture was evaporated to dryness and the residue was chromatographed on silica gel using firstly ethyl acetate/petrol (1:1) and then methanol/ dichloromethane (1:9) for the elution. Evaporation of the dichloromethane solution gave a gum which was added to a solution of 144 mg (0.35 mmol) of N-[(9-fluorenyl) methoxycarbonyl]-O-tert-butyl-L-α-aspartic acid, 54 mg (0.4 mmol) of hydroxybenzotriazole and 96 mg (0.5 mmol) of 1-(3-dimethylaminopropyl)-3-ethylcarbodiimide hydrochloride in 15 ml of dichloromethane. The mixture was stirred for 18 hours, then washed with 2M hydrochloric acid and saturated sodium bicarbonate solution, dried over magnesium sulphate and evaporated to dryness. Trituration of the residue with diethyl ether gave 360 mg of N2-[N-[N-[N-[O-tert-butyl-N-[(9-fluorenyl)methoxycarbonyl]-L-α-aspartyl]-O-tert-butyl-L-α-glutamyl]-2-methyl-L-phenylalanyl]-3-methyl-L-valyl]-N1-[1(S)-(dimethoxymethyl)-3-butynyl]-L-leucinamide as a white solid. MS: m/e 1077 [M+H−MeOH]$^+$.

vi) 350 mg (0.32 mmol) of N2-[N-[N-[N-[O-tert-butyl-N-[(9-fluorenyl)methoxycarbonyl]-L-α-aspartyl]-O-tert-butyl-L-α-glutamyl]-2-methyl-L-phenylalanyl]-3-methyl-L-valyl]-N1-[1(S)-(dimethoxymethyl)-3-butynyl]-L-leucinamide were dissolved in 12 ml of dichloromethane and 3 ml of piperidine and the mixture was stirred at room temperature for 30 minutes. The mixture was evaporated to dryness and the residue was chromatographed on silica gel using firstly ethyl acetate/petrol (1:1) and then methanol/ dichloromethane (1:9) for the elution. Evaporation of the dichloromethane solution gave a foam which was added to a solution of 104 mg (0.6 mmol) of succinic acid monotert-butyl ester, 81 mg (0.6 mmol) of hydroxybenzotriazole and 192 mg (1 mmol) of 1-(3-dimethylaminopropyl)-3-ethylcarbodiimide hydrochloride in 10 ml of dichloromethane. The mixture was stirred for 18 hours, then washed with 2M hydrochloric acid and saturated sodium bicarbonate solution, dried over magnesium sulphate and evaporated to dryness. Chromatography of the residue on silica gel using 4% methanol in dichloromethane for the elution and trituration with ethyl acetate gave 145 mg of N2-[N-[N-[N-[N-[3-(tert-butoxycarbonyl)propionyl]-O- tert-butyl-L-α-aspartyl]-O-tert-butyl-L-α-glutamyl]-2-methyl-L-phenylalanyl]-3-methyl-L-valyl]-N1-[1(S)-(dimethoxymethyl)-3-butynyl]-L-leucinamide as a white solid. MS: m/e 1043 [M+H]+, 1011 [M+H−MeOH]+.

EXAMPLE 3

94 mg (0.86 mmol) of N2-[N-[N-[N-[N-[3-(tert-butoxycarbonyl)-propionyl]-O-tert-butyl-L-α-aspartyl]-O-tert-butyl-L-α-glutamyl]-2-methyl-L-phenylalanyl]-3-methyl-L-valyl]-N1-[3,3,3-trifluoro-1(S)-(dimethoxymethyl)propyl]-L-leucinamide were stirred in a mixture of 4 ml of trifluoroacetic acid, 4 ml of dichloromethane and 30 mg of water at room temperature for 30 minutes. The solution was evaporated to dryness in a vacuum and the residue was chromatographed on silica gel using dichloromethane/methanol/acetic acid/water (120:15:3:2) for the elution. There were obtained 41 mg of 2(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4,4,4-trifluorobutyraldehyde (7:1 mixture of diastereoisomers) as a white solid. MS: m/e 873 [M+H]+.

The starting material was prepared as follows:

184 mg (0.2 mmol) of N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine were suspended in 6 ml of dichloromethane and treated with 34 mg (0.25 mmol) of hydroxybenzotriazole followed by 391 mg (1.75 mmol) of 3,3,3-trifluoro-1(S)-dimethoxymethyl-propylamine hydrochloride and 690 mg (6 mmol) of N-ethylmorpholine. The mixture was stirred for 2 hours, then washed in sequence with 2M hydrochloric acid and saturated sodium bicarbonate solution and dried over magnesium sulphate. The solvent was removed by evaporation and the resulting solid, after trituration with diethyl ether, was chromatographed on silica gel using 4% methanol in dichloromethane for the elution. There were obtained 101 mg of N2-[N-[N-[N-[N-[(3-tert-butoxycarbonyl)-O-tert-butyl-L-α-aspartyl-O-tert-butyl-L-α-glutamyl]-2-methyl-L-phenylalanyl]-3-methyl-L-valyl]-N1 -[3,3,3-trifluoro-1(S)-(dimethoxymethyl)propyl]-L-leucinamide as a white solid. MS: m/e 1088 [M+H]+.

EXAMPLE 4

0.02 g (0.006 mmol) of 5-[4-[[N-[N-[N-[(9-fluorenyl)-methoxycarbonyl]-2-methyl-L-phenylalanyl]-3-methyl-L-valyl]-L-leucyl]-N-3,3,3-trifluoro-1 (RS)-(dimethoxymethyl)propyl]-amino]methyl]-3,5-dimethoxyphenoxy]-N-(4-methyl-α-(RS)-phenylbenzyl) valeramide-polystyrene conjugate was suspended and agitated in 0.7 ml of dimethylformamide/piperidine (4:1). After 5 minutes the resin was drained and then resuspended in and agitated with 0.7 ml of dimethylformamide/piperidine (4:1) for a further 5 minutes. The resin was then drained and washed five times with 1.5 ml of dimethylformamide.

The resin was then suspended in a solution of 0.026 g (0.06 mmol) of N-[(9-fluorenyl)methoxycarbonyl]-3-(2-naphthyl)-D-alanine in 0.3 ml of dimethylformamide and then a mixture of 0.019 g (0.06 mmol) of 2-(1H-benzotriazol-1-yl)-1,1,3,3-tetramethyluronium tetrafluoraborate and 0.012 g (0.12 mmol) of N-methylmorpholine dissolved in 0.3 ml of dimethylformamide was added. After agitating for 2 hours the resin was drained and washed five times with 1.5 ml of dimethylformamide.

The resin was resuspended in and agitated with 1.5 ml of dimethylformamide/piperidine (4:1). After 5 minutes the resin was drained and resuspended in and agitated with dimethylformamide/piperidine (4:1) for a further 5 minutes. Then, the resin was drained and washed five times with 1.5 ml of dimethylformamide.

The resin was then suspended in a solution of 0.025 g (0.06 mmol) of N-[(9-fluorenyl)methoxycarbonyl]-O-tert-butyl-L-α-aspartic acid in 0.3 ml of dimethylformamide and then a mixture of 0.019 g (0.06 mmol) of 2-(1H-benzotriazol-1-yl)-1,1,3,3-tetramethyluronium tetrafluoraborate and 0.012 g (0.12 mmol) of N-methylmorpholine dissolved in 0.3 ml of dimethylformamide was added. After agitating for 2 hours the resin was drained and washed five times with 1.5 ml of dimethylformamide.

The resin was resuspended in and agitated with 1.5 ml of dimethylformamide/piperidine (4:1). After 5 minutes the resin was drained and resuspended in and agitated with dimethylformamide/piperidine (4:1) for a further 5 minutes. Then, the resin was drained and washed five times with 1.5 ml of dimethylformamide.

The resin was then suspended in a solution of 0.01 g (0.06 mmol) tert-butyl hydrogen succinate in 0.3 ml of dimethylformamide and treated with a mixture of 0.019 g (0.06 mmol) 2-(1H-benzotriazol-1-yl)-1,1,3,3-tetramethyluronium etrafluoroborate and 0.012 g (0.12 mmol) of N-methylmorpholine dissolved in 0.3 ml of dimethylformamide. After agitating for 2 hours the resin was drained and washed 5 times with 1.5 ml of dimethylformamide and then twice with 1.5 ml of dichloromethane.

The resin was treated with 0.8 ml of trifluoroacetic acid/water (19:1) and then agitated for 30 minutes. It was then filtered off and washed with 0.8 ml of trifluoroacetic acid/water (19:1). The combined trifluoroacetic acid/water mixtures were then evaporated in a vacuum centrifuge and the residue was suspended in 0.8 ml of acetonitrile/water (1:1) and freeze dried. There were obtained 6.3 mg of 2(RS)-[[N-[N-[N-[N-[N-(3-carboxypropionyl)-L-α-aspartyl]-3-(2-naphthyl)-D-alanyl]-2-methyl-L-phenylalanyl]-3-methyl-L-valyl]-L-leucyl]amino]-4,4,4-trifluorobutyraldehyde as a white solid; MS: m/e 941.5 [M+H]+.

The starting material was prepared as follows:

i) 18 g (60.0 mmol) of N,O-dimethyl 2(RS)-(tert-butoxyformamido)-4,4,4-trifluorobutyrohydroxamate were dissolved in 230 ml of anhydrous tetrahydrofuran and the solution was cooled to 0° C. 48 ml (48 mmol) of a 1M solution of lithium aluminium hydride in tetrahydrofuran were then added dropwise while maintaining the temperature at 0° C. The mixture was stirred for 10 minutes at 0° C. and then the reaction was quenched by the dropwise addition of saturated potassium hydrogen sulphate solution to pH 1 while maintaining the temperature at below 20° C. The resulting white slurry was stirred vigorously for a further 30 minutes and was then partitioned in three equal aliquots of diethyl ether. The combined diethyl ether fractions were washed with saturated sodium chloride solution, dried over anhydrous magnesium sulphate, filtered and evaporated. The residue was then dissolved in 100 ml of anhydrous saturated methanolic hydrogen chloride solution and left overnight at 4° C. The mixture was evaporated and the residue was triturated with dichloromethane. The filtrate was evaporated and the residue was chromatographed on silica gel using 5% methanol, 3% acetic acid and 1.5% water in dichloromethane for the elution. There were obtained 8.80 g of 3,3,3-trifluoro-2(RS)-(dimethoxymethyl)-propylamine hydrochloride as a white solid. $^1$H NMR: (CDCl$_3$)δ: 2.60–2.96 (m,2H), 3.49 (d,6H), 3.57–3.69 (q,1H), 4.66 (d,1H), 8.72 (br s,3H).

ii) To a stirred mixture of 5.6 g (25.0 mmol) of 3,3,3-trifluoro-2(RS)-(dimethoxymethyl)-propylamine hydrochloride 3.65 ml of triethylamine, 7.8 g (25.0 mmol) of 4-[4-(ethoxycarbonyl)butoxy]2,6-dimethoxybenzaldehyde and 25 g of 3 Å molecular sieves in dichloromethane were added 5.8 g (27.5 mmol) of sodium triacetoxyborohydride. After 3 hours the molecular sieves were removed by filtration. The filtrate was then washed with three equal aliquots of saturated sodium bicarbonate solution and dried over anhydrous magnesium sulphate and filtered. The solvent was removed by evaporation and the resulting orange oil was chromatographed on silica gel using 60% ethyl acetate in hexane for the elution. There were obtained 10.4 g of ethyl 5-[4-[[3,3,3-trifluoro-1(RS)-(dimethoxymethyl) propylamino]methyl]-3,5-dimethoxyphenoxy]valerate as a pale orange oil; $^1$H NMR : (CDCl$_3$)δ: 1.25 (t,3H), 1.78–1.87 (m,4H), 2.18–2.52 (m,4H), 2.86–2.92 (m,1H), 3.33 (d,6H), 3.77 (s,6H), 3.81 (d,2H), 3.96 (t,2H), 4.13 (q,2H), 4.26 (d,1H), 6.18 (s,2H); MS: m/e 482.2 [M+H], 504.2 [M+Na].

iii) A solution of 6.6 g (18.7 mmol) of N-[(9-fluorenyl)-methoxycarbonyl]-L-leucine and 9.7 g (18.7 mmol) of 7-azabenzotriazol-1-yloxytris(pyrrolidino)phosphonium hexafluorophosphate in 50 ml of anhydrous dichloromethane was stirred at room temperature for 15 minutes. To this mixture were then added 6.0 g (12.4 mmol) of ethyl 5-[4-[[3,3,3-trifluoro-1(RS)-(dimethoxymethyl) propylamino]methyl]-3,5-dimethoxyphenoxy]valerate and 4.3 ml of (24.8 mmol) diisopropylethylamine. After stirring overnight at 25° C. the mixture was diluted with dichloromethane and washed in sequence with water, 10% citric acid solution, saturated sodium hydrogen carbonate solution and saturated sodium chloride solution, then dried over anhydrous magnesium sulphate and filtered. The solvent was removed by evaporation and the residue was chromatographed on silica gel using 30% ethyl acetate in hexane for the elution. There were obtained 8.06 g of ethyl 5-[4-[[N-[N-[(9-fluorenyl)methoxycarbonyl]-L-leucyl]-N-[3,3,3-trifluoro-1(RS)-(dimethoxymethyl)propyl]amino]methyl]-3,5-dimethoxyphenoxy]valerate; MS: m/e 839.4 [M+Na], 855.3 [M+K].

iv) 8.0 g (9.8 mmol) of 5-[4-[[N-[N-[(9-fluorenyl) methoxycarbonyl]-L-leucyl]-N-[3,3,3-trifluoro-1(RS)-(dimethoxymethyl)-propyl]amino]methyl]-3,5-dimethoxyphenoxy]valerate and 40 ml of piperidine were dissolved in 145 ml of dry dichloromethane and the solution was stirred at room temperature for 30 minutes. It was then evaporated in a vacuum and the residue was chromatographed on silica gel using 2% methanol, 49% dichloromethane and 49% hexane followed by 5% methanol, 47.5% dichloromethane and 47.5% hexane for the elution. There were obtained 4.09 g of ethyl 5-[4-[[N-[3,3,3-trifluoro-1(RS)-dimethoxymethyl)propyl]-N-(L-leucyl) amino]-methyl]-3,5-dimethoxyphenoxy]valerate as a clear stiff oil; MS: m/e 595 [M+H].

v) A solution of 2.76 g (7.8 mmol) of N-[(9-fluorenyl) methoxycarbonyl]-3-methyl-L-valine, 1.60 g (8.5 mmol) of 1-(3-dimethylaminopropyl)-3-ethylcarbodiimide hydrochloride and 1.60 g (10.7 mmol) of N-hydroxybenzotriazole in 70 ml of dichloromethane was stirred at 0 C. for 15 minutes. There were then added 4.06 g (7.1 mmol) of ethyl 5-[4-[[N-[3,3,3-trifluoro-1 (RS)-(dimethoxymethyl)propyl]-N-(L-leucyl)-amino]methyl]-3,5-dimethoxyphenoxy] valerate and 2.7 ml (21.3 mmol) of N-ethylmorpholine in 70 ml of dichloromethane. After stirring overnight at room temperature the mixture was washed in sequence with 10% citric acid solution, saturated sodium hydrogen carbonate solution and saturated sodium chloride solution, dried over anhydrous magnesium sulphate, filtered and evaporated. The residue was chromatographed on silica gel using 35% ethyl acetate in hexane for the elution. There were obtained 6.11 g of ethyl 5-[4-[[N-[N-[N-[(9-fluorenyl) methoxycarbonyl]-3-methyl-L-valyl]-L-leucyl]-N-[3,3,3-trifluoro-1(RS)-(dimethoxyethyl)propyl]amino]methyl]-3, 5-dimethoxy-phenoxy]valerate as a white foam; MS: m/e 952.5 [M+Na], 968.5 [M+K].

vi) 5.8 g (6.3 mmol) of ethyl 5-[4-[[N-[N-[N-[(9-fluorenyl)methoxycarbonyl]-3-methyl-L-valyl]-L-leucyl]-N-[3,3,3-trifluoro-1(RS)-(dimethoxyethyl)propyl]amino] methyl]-3,5-dimethoxyphenoxy]valerate and 18 ml of piperidine were dissolved in 90 ml of dichloromethane and the solution was stirred at room temperature for 1 hour. It was then evaporated and the residue was chromatographed on silica gel using 3% methanol, 48.5% dichloromethane and 48.5% hexane for the elution. There were obtained 4.1 g of ethyl 5-[4-[[N-[3,3,3-trifluoro-1(RS)-(dimethoxymethyl)propyl]-N-[N-(3-methyl-L-valyl)-L-leucyl]amino]methyl]-3,5-dimethoxyphenoxy]-valerate as a white foam; MS: m/e 708.6 [M+H], 730.5 [M+Na].

vii) 4.0 g (5.7 mmol) of ethyl 5-[4-[[N-[3,3,3-trifluoro-1 (RS)-(dimethoxymethyl)propyl]-N-[N-(3-methyl-L-valyl)-L-leucyl]-amino]methyl]-3,5-dimethoxyphenoxy]-valerate were dissolved in 40 ml of methanol. 2.4 g (17.3 mmol) of potassium carbonate and 8.0 ml of water were then added and the mixture was stirred for 2 days at room temperature. The solvent was removed by evaporation and the residue was dissolved in 20 ml of water and 20 ml of dioxan. 2.9 g (8.6 mmol) of N-[(9-fluorenyl)-methoxycarbonyloxy]-succinimide were then added and the mixture was stirred for 3 hours. The mixture was adjusted to pH 3 with 10% citric acid and then washed with three equal aliquots of dichloromethane. The combined organic layers were washed with saturated sodium chloride solution, dried over anhydrous magnesium sulphate, filtered and the filtrate was evaporated. The residue was chromatographed on silica gel using 4% tert-butyl methyl ether in dichloromethane for the elution. There were obtained 5.12 g of 5-[4-[[N-[N-[N-[(9-fluorenyl) methoxycarbonyl]-3-methyl-L-valyl]-L-leucyl]-N-[3,3,3-trifluoro-1(RS)-(dimethoxymethyl)propyl]amino]methyl]-3,5-dimethoxyphenoxy]valeric acid as a white foam; MS: m/e 870.8 [M+H−MeOH], 888.7 [M+H−CH$_3$], 889.7 [M−CH$_3$]902.7 [M+H], 924.7 [M+Na].

viii) 5.4 g (5.4 mmol) of 4-methylbenzhydrylamine resin were swollen in 30 ml of dimethylformamide, excess solvent was drained from the resin and it was then washed twice with 20 ml dimethylformamide/N-methylmorpholine (9:1). The resin was then resuspended in 10 ml of dimethylformamide containing 4.98 g (5.4 mmol) of 5-[4-[[N-[N-[N-[(9-fluorenyl)methoxycarbonyl]-3-methyl-L-valyl]-L-leucyl]-N-[3,3,3-trifluoro-1(RS)-dimethoxymethyl)propyl]amino]methyl-3,5-dimethoxyphenoxy]-valeric acid and 1.74 g (5.4 mmol) of 2-(1H-benzotriazol-1-yl)-1,1,3,3-tetramethyluronium tetrafluoraborate. Thereto there were added 1.18 ml (10.8 mmol) of N-methylmorpholine dissolved in 10 ml of dimethylformamide. The resulting mixture was agitated for 2 hours and the resin was then drained and washed five times with 30 ml of dimethylformamide. The resin was then resuspended in 30 ml of dimethylformamide containing 2.03 ml (21.6 mmol) of acetic anhydride and 2.96 ml (27 mmol) of N-methylmorpholine. This mixture was agitated for 30 minutes and the resin was then drained and washed five times with 30 ml of dimethylformamide each time. The resin was resuspended in and agitated in 30 ml of dimethylformamide/piperidine (4:1). After 5 minutes the resin was drained, resuspended and again agitated in the foregoing dimethylformamide/piperidine mixture for a further 5 minutes. The resin was then drained and washed five times with 30 ml of dimethylformamide.

ix) A solution of 3.2 g (8.1 mmol) of N-[(9-fluorenyl)methoxycarbonyl]-3-(2-methylphenyl)-L-alanine and 2.17 g (6.75 mmol) of 2-(1H-benzotriazol-1-yl)-1,1,3,3-tetramethyluronium tetrafluoroborate in 22 ml of dimethylformamide was added to the resin from paragraph viii) and subsequently 1.5 ml (13.5 mmol) of N-methylmorpholine were added. The mixture was agitated for 30 minutes and then the resin was drained and washed five times with 30 ml of dimethylformamide, twice with 30 ml of dichloromethane, twice with 30 ml of ethyl acetate and twice with 30 ml of diethyl ether. After drying there were obtained 8.95 g of 5-[4-[[N-[N-[N-[(9-fluorenyl)methoxycarbonyl]-2-methyl-L-phenylalanyl]-3-methyl-L-valyl]-L-leucyl]-N-[3,3,3-trifluoro-1(RS)-(dimethoxymethyl)propyl]amino]methyl]-3,5-dimethoxyphenoxy]-N-(4-methyl-α-(RS)-phenylbenzyl)valeramide-polystyrene conjugate as a pale brown solid (0.31 mmol/g loading estimated by quantitation of dibenzofulvene at 301 nm).

EXAMPLE 5

0.236 g (0.215 mmol) of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(RS)-(4,4,5,5-tetramethyl-1,3,2-dioxaborolan-2-yl)-3-butenyl]-L-leucinamide was dissolved in 1.5 ml of water, 13.5 ml of trifluoroacetic acid and 7 ml of dichloromethane and the solution was stirred at room temperature for 1 hour and then left to stand at 4° C. for 18 hours. The solution was then diluted with toluene and evaporated. The residue was triturated with diethyl ether and the resulting solid was filtered off. The solid was purified by RP-HPLC on a Dynamax C18 column (5 micron, 300 Å, 21.4 mm×50 mm). The elution gradient comprised 95% SSA:5% SSB to 95%:SSB 5% SSA over 6 minutes and there were obtained, after lyophilization, 69 mg of 1(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-3-butenylboronic acid as a foam; MS: m/e 847 [M+H].

The starting material was prepared as follows:

i) 2 g (9.48 mmol) of 2-(dichloromethyl)-4,4,5,5-tetramethyl-1,3,2-dioxaborolane were dissolved in 30 ml of tetrahydrofuran and the solution was cooled under a nitrogen atmosphere to −78° C. 9.5 ml (9.5 mmol) of 1M allylmagnesium bromide were added dropwise and the solution was stirred at room temperature for 18 hours. The solution was partitioned between ethyl acetate, saturated sodium chloride solution and 2M hydrochloric acid solution. The aqueous layer was extracted with ethyl acetate and the organic layers were combined and dried over anhydrous sodium sulphate. After filtration and evaporation the oil obtained was distilled to give 1.45 g of 2-(1 (RS)-chloro-3-butenyl)-4,4,5,5-tetramethyl-1,3,2-dioxaborolane; b.p. 53° C./0.4 mm Hg.

ii) 6.6 ml (6.6 mmol) of 1M lithium bis(trimethylsilyl)amide in tetrahydrofuran were added dropwise to a solution of 1.43 g (6.6 mmol) of 2-(1 (RS)-chloro-3-butenyl)-4,4,5,5-tetramethyl-1,3,2-dioxaborolane in 20 ml of tetrahydrofuran under nitrogen at −78° C. The solution was then stirred overnight at room temperature. The solvent was removed by evaporation and the residue was taken up in diethyl ether. Insoluble material was removed by filtration and the filtrate was cooled to 0° C. 1.5 ml (19.8 mmol) of trifluoroacetic acid were added and the solution was stirred at 0° C. for 30 minutes. The resulting precipitate was filtered off and dried to give 0.5 g of α-(RS)-allyl-4,4,5,5-tetramethyl-1,3,2-dioxaborolane-2-methylamine trifluoroacetate which was used in the next step without further purification.

iii) 0.25 g (0.27 mmol) of N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine was dissolved in 4 ml of dimethylformamide and 4 ml of dichloromethane. 0.15 ml (1.6 mmol) of N-methylmorpholine was added and the solution was cooled to −15° C. under a nitrogen atmosphere. 50 mg (0.38 mmol) of isobutyl chloroformate were added and the solution was stirred for 10 minutes at −15° C. 0.1 g (0.32 mmol) of α-(RS)-allyl-4,4,5,5-tetramethyl-1,3,2-dioxaborolane-2-methylamine trifluoroacetate was added and the mixture was stirred at room temperature for 18 hours. After evaporation the residue was partitioned between ethyl acetate and 2M hydrochloric acid. The organic layer was washed with 2M hydrochloric acid, water and saturated sodium chloride solution and then dried over anhydrous sodium sulphate. After evaporation there was obtained 0.3 g of N2-N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1 -[1(RS)-(4, 4,5,5-tetramethyl-1,3,2-dioxaborolan-2-yl)-3-butenyl]-L-leucinamide in the form of a solid; MS: m/e 1097 [M+H].

EXAMPLE 6

0.25 g (0.23 mmol) of N2-N-[N-[N-[N-[N-[3-(tert-butoxycarbonyl)propionyl-O-tert-butyl-L-α-aspartyl]-O-tert-butyl-L-α-glutamyl]-2-methyl-L-phenylalanyl]-3-methyl-L-valyl]-N1-[1(RS)-(4,4,5,5-tetramethyl-1,3,2-dioxaborolan-2-yl)propyl]-L-leucinamide was dissolved in 1.5 ml of water, 13.5 ml of trifluoroacetic acid and 7 ml of dichloromethane and the solution was stirred at room temperature for 1 hour and then left to stand at 4° C. for 18 hours. The solution was diluted with toluene and evaporated. The residue was triturated with diethyl ether and the resulting solid was filtered off. The solid was purified by RP-HPLC on an Aquapore octyl column (20 micron, 100 mm×10 mm). The elution gradient comprised 95% SSA:5% SSB to 5% SSA:95% SSB over 6 minutes and there were obtained, after lyophilization, 92 mg of 1(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]propylboronic acid as a foam; MS: m/e 835 [M+H].

The starting material was prepared as follows:

i) 2.64 g (12.5 mmol) of 2-(dichloromethyl)-4,4,5,5-tetramethyl-1,3,2-dioxaborolane were dissolved in 30 ml of tetrahydrofuran and the solution was cooled under a nitrogen atmosphere to −78° C. 11.8 ml (12.5 mmol) of 1.06M ethylmagnesium bromide were added dropwise and the solution was stirred at room temperature for 18 hours. The solution was partitioned between ethyl acetate, saturated sodium chloride solution and 2M hydrochloric acid solution. The aqueous layer was extracted with ethyl acetate and the organic layers were combined and dried over anhydrous sodium sulphate. After filtration and evaporation the oil obtained was distilled to give 2.04 g of 2-[1(RS)-chloropropyl]-4,4,5,5-tetramethyl-1,3,2-dioxaborolane; b.p. 53° C./0.8 mm Hg.

ii) 10 ml (10 mmol) of 1M lithium bis(trimethylsilyl)amide in tetrahydrofuran were added dropwise to a solution of 2.03 g (9.9 mmol) of 2-[1(RS)-chloropropyl]-4,4,5,5-tetramethyl-1,3,2-dioxaborolane in 20 ml tetrahydrofuran under a nitrogen atmosphere at −78° C. The solution was then stirred overnight at room temperature. The solvent was removed by evaporation and the residue was taken up in diethyl ether. Insoluble material was removed by filtration and the filtrate was cooled to 0° C. 2.3 ml (30 mmol) of trifluoroacetic acid were added and the solution was stirred at 0° C. for 30 minutes. The resulting precipitate was filtered off and dried to give 0.5 g of a-(RS)-ethyl-4,4,5,5-tetramethyl-1,3,2-dioxaborolane-2-methylamine trifluoroacetate as a white solid.

Analysis for $C_{11}H_{21}BNF_3O_4$ [299.15]. Calculated: C, 44.17; H, 7.08; N, 4.68% Found: C, 44.06, H, 7.05, N, 4.71%.

iii) 0.25 g (0.27 mmol) of N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine was dissolved in 2 ml of dimethylformamide and 5 ml of dichloromethane. 0.15 ml (1.6 mmol) of N-methylmorpholine was added and the solution was cooled to −15° C. under a nitrogen atmosphere. 50 mg (0.38 mmol) of isobutyl chloroformate were added and the solution was stirred for 10 minutes at −15° C. 0.1 g (0.33 mmol) of α-(RS)-ethyl-4,4,5,5-tetramethyl-1,3,2-dioxaborolane-2-methylamine trifluoroacetate was added and the mixture was stirred at room temperature for 18 hours. After evaporation the residue was partitioned between ethyl acetate and 2M hydrochloric acid. The organic layer was washed with 2M hydrochloric acid, water and saturated sodium chloride solution and then dried over anhydrous sodium sulphate. After evaporation there was obtained 0.26 g of N2-N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(RS)-(4,4,5,5-tetramethyl-1,3,2-dioxaborolan-2-yl)propyl]-L-leucinamide in the form of a solid; MS: m/e 1085 [M+H].

EXAMPLE 7

0.16 g (14.6 mmol) of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(RS)-(4,4,5,5-tetramethyl-1,3,2-dioxaborolan-2-yl)butyl]-L-leucinamide was dissolved in 4 ml of trifluoroacetate acid and 4 ml of dichloromethane. 4 drops of water were added and the solution was stirred at room temperature for 3 hours. The residue was triturated with diethyl ether and the resulting solid was filtered off and dried to give, after lyophilization, 139 mg of 1(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]butylboronic acid as a foam; MS: m/e 849 [M+H].

The starting material was prepared as follows:

i) 0.5 g (2.37 mmol) of 2-(dichloromethyl)-4,4,5,5-tetramethyl-1,3,2-dioxaborolane was dissolved in 10 ml of tetra-hydrofuran and the solution was cooled under a nitrogen atmosphere to −78° C. 2.4 ml (2.4 mmol) of 1M propylmagnesium bromide were added dropwise and the solution was stirred at room temperature for 18 hours. The solution was partitioned between ethyl acetate, saturated sodium chloride solution and 2M hydrochloric acid solution. The aqueous layer was extracted with ethyl acetate and the organic layers were combined and dried over anhydrous sodium sulphate. After evaporation there was obtained 0.38 g of 2-[1(RS)-chlorobutyl]-4,4,5,5-tetramethyl-1,3,2-dioxaborolane as an oil which was used in the next step without further purification.

ii) 1.7 ml (1.7 mmol) of 1M lithium bis(trimethylsilyl)amide in tetrahydrofuran were added dropwise to a solution of 0.37 g (1.69 mmol) of 2-[1(RS)-chlorobutyl]-4,4,5,5-tetramethyl-1,3,2-dioxaborolane in 20 ml of tetrahydrofuran under nitrogen at −78° C. The solution was then stirred overnight at room temperature. The solvent was removed by evaporation and the residue was taken up in diethyl ether. Insoluble material was removed by filtration and the filtrate was cooled to 0° C. 0.39 ml (5.1 mmol) of trifluoroacetic acid was added and the solution was stirred at 0° C. for 30 minutes. The solution was evaporated and the residue was co-evaporated with toluene to give 0.62 g of α-(RS)-propyl-4,4,5,5-tetramethyl-1,3,2-dioxaborolane-2-methylamine trifluoroacetate as a brown oil which was used in the next step without further purification.

iii) 0.2 g (0.218 mmol) of N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine was dissolved in 2 ml of dimethylformamide and 6 ml of dichloromethane. 0.12 ml (1.1 mmol) of N-methylmorpholine was added and the solution was cooled to −15° C. under a nitrogen atmosphere. 40 mg (0.31 mmol) of isobutyl chloroformate were added and the solution was stirred for 10 minutes at −15° C. 0.14 g (0.44 mmol) of α-(RS)-propyl-4,4,5,5-tetramethyl-1,3,2-dioxaborolane-2-methylamine trifluoroacetate was added and the mixture was stirred at room temperature for 66 hours. After evaporation the residue was partitioned between ethyl acetate and 2M hydrochloric acid. The organic layer was washed with 2M hydrochloric acid, water and saturated sodium chloride solution and then dried over anhydrous sodium sulphate. After evaporation there was obtained 0.17 g of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-N1(RS)-(4,4,5,5-tetramethyl-1,3,2-dioxaborolan-2-yl)butyl]-L-leucinamide in the form of a solid; NMR (DMSO, 400 MHz) δ: 0.75–0.9 (m,17H), 1.01–1.08 (m,6H), 1.15–1.25 (m,1H), 1.35 9s,36H), 1.4–1.7 (m,4H), 1.75–1.8 (m,1H), 2.05–2.15

(m,2H), 2.23 (s,3H), 2.29–2.41 (m,6H), 2.55–2.6 (m,1H), 2.7–2.74 (m,1H), 2.95–3.05 (m,1H), 4.15–4.25 (m,3H), 4.48–4.55 (m,1H), 4.6–4.7 (m,1H), 7.05–7.11 (m,4H), 7.7–7.81 (m,2H), 8.05–8.12 (m,2H), 8.15–8.25 (m,2H).

EXAMPLE 8

0.126 g (0.116 mmol) of N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1[3,3-difluoro-[1(S)-(dimethoxymethyl)-butyl]-L-leucinamide was dissolved in 5 ml of trifluoroacetic acid and 5 ml of dichloromethane. A few drops of water were added and the solution was stirred at room temperature for 1 hour. The residue was evaporated, the residue was triturated with diethyl ether and the resulting solid was filtered off. The solid was purified by chromatography on silica gel using dichloromethane/methanol/acetic acid/water (75:15:3:2) for the elution. There were obtained 67 mg of 2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4,4-difluorovaleraldehyde as a cream coloured solid of melting point 128–130° C.

The starting material was prepared as follows:

i) 1.5 g (4.62 mmol) of 4,4-difluoro-L-norvaline p-toluenesulphonate were dissolved in dimethylformamide. 1.71 g (7.85 mmol) of di-tert-butyl dicarbonate and 3.23 ml (23.25 mmol) of triethylamine were added and the solution was stirred at 60° C. for 3 hours. The solution was evaporated and the residue was partitioned between ethyl acetate and 2M hydrochloric acid. The organic layer was dried over anhydrous sodium sulphate and evaporated. The resulting oil was purified by chromatography on silica gel using ethyl acetate for the elution. There were obtained 1.16 g of N-(tert-butoxycarbonyl)-4,4-difluoro-L-norvaline as an orange oil which was used directly in the next step.

ii) 1.16 g (4.62 mmol) of N-(tert-butoxycarbonyl)-4,4-difluoro-L-norvaline were dissolved in 30 ml of dichloromethane. 6.4 ml (46.2 mmol) of triethylamine, 564 mg (4.62 mmol) of N,N-dimethylaminopyridine, 1.77 g (9.24 mmol) of 1-(3-dimethylaminopropyl)-3-ethylcarbodiimide hydrochloride and 1.8 g (18.5 mmol) of N,O-dimethylhydroxylamine hydrochloride were added and the solution was stirred at room temperature for 18 hours. The mixture was diluted with ethyl acetate, washed with 2M hydrochloric acid and aqueous sodium hydrogen carbonate solution, dried over anhydrous sodium sulphate and evaporated to give an oil which was purified by chromatography on silica gel using ethyl acetate for the elution. There were obtained 547 mg of N,O-dimethyl 2(S)-(tert-butoxyformamido)-4,4-difluorovalerohydroxamate as a colourless oil; MS: m/e 297 [M+H].

iii) 547 mg (1.85 mmol) of N,O-dimethyl 2(S)-(tert-butoxyformamido)-4,4-difluorovalerohydroxamate were dissolved in 12 ml of tetrahydrofuran and the solution was stirred at 0° C. 1.76 ml (1.76 mmol) of 1M lithium aluminium hydride in tetrahydrofuran were added and the solution was stirred for 15 minutes. The mixture was partitioned between ethyl acetate and saturated aqueous potassium hydrogen sulphate solution. The organic layer was evaporated and the residue was dissolved in freshly prepared methanolic hydrogen chloride solution. After 1 hour the solution was evaporated to give 372 mg of 3,3-difluoro-1 (S)-(dimethoxymethyl)butylamine hydrochloride as a white solid; MS: m/e 184 [M+H].

iv) 0.3 g (0.33 mmol) of N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine was dissolved in 15 ml of dichloromethane. 0.22 ml (1.98 mmol) of N-methylmorpholine, 96 mg (0.5 mmol) of 1-(3-dimethylaminopropyl)-3-ethylcarbodiimide hydrochloride, 45 mg (0.33 mmol) of hydroxybenzotriazole and 217 mg (0.99 mmol) of 3,3-difluoro- 1(S)-(dimethoxymethyl) butylamine hydrochloride were added and the solution was stirred at room temperature for 18 hours. The mixture was washed with 2M hydrochloric acid and aqueous sodium hydrogen carbonate solution, dried over anhydrous sodium sulphate and evaporated. The residue was triturated with diethyl ether and the resulting solid was filtered off and dried. There were obtained 143 g of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[3,3-difluoro-1(S)-dimethoxymethyl)butyl]-L-leucinamide; MS: m/e 1106 [M+Na]+.

EXAMPLE 9

80 mg (0.075 mmol) of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N 1-[1(R)-dimethoxymethyl)-2-(methylthio)ethyl]-L-leucinamide were dissolved in 10 ml of trifluoroacetic acid/dichloromethane (1:1) containing 3 drops of water and the solution was stirred for 90 minutes under a nitrogen atmosphere. The solution was evaporated to dryness under a vacuum and the residue was re-evaporated twice with toluene. The solid was triturated with 10 ml of diethyl ether to give 60 mg of 2(R)-[N-[N-[N-[N-(3-carboxypropionyl)-L-α-aspartyl]-L-α-glutamyl]-2-methyl-L-phenylalanyl]-3-methyl-L-valyl]-L-leucyl]amino]-3-(methylthio)propionaldehyde as a white solid; MS: m/e 851.5 [M+H]$^+$.

The starting material was prepared as follows:

i) 2 g (8.51 mmol) of N-(tert-butoxycarbonyl)-S-methyl-L-cysteine were dissolved in 60 ml of anhydrous tetrahydrofuran and then 1.81 g (11.9 mmol) of 1-hydroxybenzotriazole hydrate, 2.28 g (11.88 mmol) of 1-(3-dimethylaminopropyl)-3-ethylcarbodiimide hydrochloride, 1.16 g (11.90 mmol) of N,O-dimethylhydroxylamine hydrochloride and 5.9 ml (33.87 mmol) of N,N-diisopropylethylamine were added. The mixture was stirred overnight at room temperature. The solvent was removed by evaporation and the residue was partitioned between ethyl acetate and 5% (w/v) aqueous citric acid. The organic phase was washed with saturated aqueous sodium bicarbonate solution and then with saturated sodium chloride solution, dried over magnesium sulphate and evaporated under a vacuum to give 2.27 g of N,O-dimethyl 2(R)-(tert-butoxyformamido)-3-(methylthio) propionohydroxamate as a colourless oil; MS: m/e 279 [M+H]$^+$.

ii) 2.22 g (7.90 mmol) of N,O-dimethyl 2(R)-(tert-butoxyformamido)-3-(methylthio)propionohydroxamate were dissolved in 25 ml of anhydrous tetrahydrofuran and the solution was cooled to 0° C. 4.69 ml (4.69 mmol) of a 1M solution of lithium aluminium hydride in tetrahydrofuran were added dropwise and the mixture was stirred for 15 minutes. The reaction was quenched by the dropwise addition of saturated aqueous potassium hydrogen sulphate solution and then 50 ml of diethyl ether were added. The mixture was stirred vigorously for 20 minutes. The organic phase was separated, washed with saturated aqueous sodium bicarbonate solution, dried over magnesium sulphate and evaporated to give 1.75 g of aldehyde which, without further purification, was dissolved in 20 ml of saturated methanolic hydrogen chloride solution and stirred for 2 hours under a nitrogen atmosphere at room temperature. The solvent was removed by evaporation and the residue was re-evaporated twice with toluene to give 1.3 g of dimethyl acetal as a colourless oil.

90 mg (0.45 mmol) of the dimethyl acetal were dissolved in 40 ml dichloromethane and then 200 mg (0.22 mmol) of N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine, 100 mg (0.87 mmol) of N-ethylmorpholine, 40 mg (0.26 mmol) of 1-hydroxybenzotriazole hydrate and 50 mg (0.26 mmol) of 1-(3-dimethylaminopropyl)-3-ethylcarbodiimide hydrochloride were added. The solution was stirred overnight at room temperature. The organic phase was washed with 5% (w/v) aqueous citric acid and then with saturated aqueous sodium bicarbonate solution, dried over magnesium sulphate and evaporated under a vacuum. The resulting oil was triturated with 10 ml of diethyl ether to give 165 mg of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(R)-(dimethoxymethyl)-2-(methylthio)ethyl]-L-leucinamide as a white solid; MS: m/e 1065.7 [M+H]$^+$.

EXAMPLE 10

50 mg (0.048 mmol) of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-3-butenyl]-L-leucinamide were dissolved in 4 ml of trifluoroacetic acid/dichloromethane (1:1) containing 3 drops of water and the solution was stirred for 1 hour under nitrogen. The solution was evaporated to dryness under a vacuum and the residue was re-evaporated twice with toluene. The solid was triturated with 10 ml of diethyl ether to give 30 mg of 2(RS)-[[N[[N-(N-[N-[N-(3-carboxypropionyl)-L-α-aspartyl]-L-α-glutamyl]-2-methyl-L-phenylalanyl]-3-methyl-L-valyl]-L-leucyl]amino]-4-pentenaldehyde; MS: m/e 831.5 [M+H]$^+$.

The starting material was prepared as follows:

i) 1.13 g (7.46 mmol) of L-allylglycine hydrochloride were dissolved in 20 ml of saturated aqueous sodium bicarbonate solution and 20 ml of dioxan. 1.95 g (8.93 mmol) of di-tert-butyl dicarbonate were added and the solution was stirred overnight and then evaporated to dryness under a vacuum. The residue was partitioned between diethyl ether and water. The aqueous phase was acidified with 2M hydrochloric acid and extracted with ethyl acetate. The organic phase was dried over magnesium sulphate and evaporated under a vacuum to give 1.6 g of N-(tert-butoxycarbonyl)-L-allylglycine as a colourless oil. $^1$H NMR (250 MHz, CDCl$_3$) δ: 1.4 (s,9H), 2.4–2.7 (m,2H), 4.3–4.5 (m,1H), 5.0 (br.d,1H), 5.1–5.2 (m,2H), 5.6–5.8 (m, 1H)

ii) N,O-Dimethyl 2(S)-(tert-butoxyformamido)-4-pentenohydroxamate was obtained in a manner analogous to that described in Example 10 i) from 1.6 g (7.44 mmol) of N-(tert-butoxycarbonyl)-L-allylglycine, 1.4 g (10.4 mmol) of 1-hydroxybenzotriazole, 1.99 g (10.4 mmol) of 1-(3-dimethylaminopropyl)-3-ethylcarbodiimide hydrochloride, 1.02 g (10.46 mmol) of N,O-dimethylhydroxylamine hydrochloride and 2.6 ml (14.93 mmol) of ethyl diisopropylamine. This gave 1.9 g of product as a colourless oil. $^1$H NMR (250 MHz, CDCl$_3$) δ: 1.4 (s,9H), 2.3–2.6 (m,2H), 3.2 (s,3H), 3.8 (s,3H), 4.6–4.7 (m,1H), 5.0–5.4 (m,3H), 5.6–5.8 (m,1H).

iii) 1.9 g (7.36 mmol) of N,O-dimethyl 2(S)-(tert-butoxyformamido)-4-pentenohydroxamate were dissolved in 20 ml of anhydrous tetrahydrofuran and the solution was cooled to 0° C. 5.40 ml (5.4 mmol) of a 1M solution of lithium aluminium hydride in tetrahydrofuran were added dropwise and the mixture was stirred for 25 minutes. The reaction was quenched by the dropwise addition of saturated aqueous potassium hydrogen sulphate and then 50 ml of diethyl ether were added. The mixture was stirred vigourously for 20 minutes. The organic phase was separated, washed with saturated aqueous sodium bicarbonate solution, dried over magnesium sulphate and evaporated to give the aldehyde which, without further purification, was dissolved in 25 ml of saturated methanolic hydrogen chloride solution and stirred for 2 hours at room temperature. The solvent was removed by evaporation and the residue was re-evaporated twice with toluene to give the amino acid acetal as a brown oil.

iv) 40 mg (0.22 mmol) of the amino acid acetal were dissolved in 4 ml of dichloromethane and then 200 mg (0.22 mmol) of N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine, 0.1 ml (0.78 mmol) of N-ethylmorpholine, 35 mg (0.22 mmol) of 1-hydroxybenzotriazole monohydrate and 50 mg (0.26 mmol) of 1-(3-dimethylaminopropyl)-3-ethylcarbodiimide hydrochloride were added. The solution was stirred overnight at room temperature. The organic phase was washed with 5% (w/v) aqueous citric acid solution and then with saturated aqueous sodium bicarbonate solution, dried over magnesium sulphate and evaporated under a vacuum. The resulting oil was triturated with 10 ml of diethyl ether to give 148 mg of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-3-butenyl]-L-leucinamide as a white solid; MS: m/e 1013.6 [M+H-MeOH]$^+$.

EXAMPLE 11

90 mg (0.081 mmol) of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[2-(butylthio)-1(R)-(dimethoxymethyl) ethyl]-L-leucinamide were dissolved in 10 ml of trifluoroacetic acid/dichloromethane (1:1) containing 3 drops of water and the solution was stirred for 90 minutes under nitrogen. The solution was evaporated to dryness under a vacuum and the residue was re-evaporated twice with toluene. The solid was triturated with 10 ml of diethyl ether to give 80 mg of 2(R)-[[N-[N-[N-[N-[N-(3-carboxypropionyl)-L-α-aspartyl-L-α-glutamyl]-2-methyl-L-phenylalanyl]-3-methyl-L-valyl]-L-leucyl]amino]-3-(butylthio)propionaldehyde as a white solid. MS: m/e 893.4 [M+H]$^+$.

The starting material was prepared as follows:

i) 2 g (16.53 mmol) of L-cysteine were dissolved in 40 ml of water/ethanol (1:1) together with 1.33 g (33.25 mmol) of sodium hydroxide pellets. 3.04 g (16.53 mmol) of butyl iodide were added and the mixture was stirred for 2 hours. The resulting S-alkylated product was treated with 3.96 g (18.14 mmol) of di-tert-butyl dicarbonate and the mixture was stirred for 1 hour. A further 3.61 g (16.53 mmol) of di-tert-butyl dicarbonate were added and the mixture was stirred overnight. The solution was evaporated to dryness under a vacuum and the residue was partitioned between diethyl ether and saturated aqueous sodium hydrogen carbonate solution. The aqueous phase was acidified by partitioning in 2M hydrochloric acid and ethyl acetate, the separated organic phase was dried over magnesium sulphate and the solvent was removed by evaporation to give 4.3 g of N-(tert-butoxycarbonyl)-S-butyl-L-cysteine as a brown oil; $^1$H NMR (250 MHz, CDCl$_3$) δ: 0.9 (t,3H), 1.3–1.6 (m,4H), 1.4 (s,9H), 2.55 (t,2H), 3.0 (br.d,2H), 4.5 (m,1H), 5.3 (br.d,1H).

ii) N,O-Dimethyl 2(R)-(tert-butoxyformamido)-3-(butylthio)-propionohydroxamate was obtained in a manner analogous to that described in Example 10 i) from 2.15 g (7.76 mmol) of N-(tert-butoxycarbonyl)-S-butyl-L-cysteine, 1.19 g (7.77 mmol) of 1-hydroxybenzotriazole monohydrate, 2.24 g (11.68 mmol) of 1-(3-dimethylaminopropyl)-3-ethylcarbodiimide hydrochloride, 1.14 g (11.68 mmol) of N,O-dimethylhydroxylamine hydrochloride and 1.34 g (11.64 mmol) of N-ethylmorpholine in 30 ml of dichloromethane. This gave 2.0 g of product as a colourless oil after column chromatography using ethyl acetate/petrol (1:2) as the eluent. $^1$H NMR (250 MHz, CDCl$_3$) δ: 0.9 (t,3H), 1.3–1.6 (m,4H), 1.4 (s,9H), 2.55 (t,2H), 2.6 –2.7 (dd,1H), 2.8–2.9 (dd,1H), 3.2 (s,3H), 3.75 (s,3H), 4.8–4.9 (m,1H), 5.3 (br.d,1H).

iii) 0.3 g (0.94 mmol) of N,O-dimethyl 2(R)-(tert-butoxyformamido)-3-(butylthio)propionohydroxamate was dissolved in 10 ml of anhydrous tetrahydrofuran and the solution was cooled to 0° C. 0.55 ml (0.55 mmol) of a 1M solution of lithium aluminium hydride in tetrahydrofuran was added dropwise and the mixture was stirred for 15 minutes. The reaction was quenched by the dropwise addition of saturated aqueous potassium hydrogen sulphate and then 20 ml of diethyl ether were added. The mixture was stirred vigorously for 20 minutes. The organic phase was separated, washed with saturated aqueous sodium bicarbonate solution, dried over magnesium sulphate and evaporated to give the aldehyde which, without further purification, was dissolved in 20 ml of saturated methanolic hydrogen chloride solution and stirred for 2 hours under a nitrogen atmosphere at room temperature. The solvent was removed by evaporation and the residue was re-evaporated twice with toluene to give the amino acid acetal as a brown oil.

200 mg (0.82 mmol) of the amino acid acetal were dissolved in 40 ml of dichloromethane and then 200 mg (0.22 mmol) of [N-[N-[N-[N-[N-[3-(tert-butoxycarbonyl) propionyl]-O-tert-butyl-L-α-aspartyl]-O-tert-butyl-L-α-glutamyl]-2-methyl-L-phenylalanyl]-3-methyl-L-valyl]-L-leucine, 100 mg (0.87 mmol) of N-ethylmorpholine, 40 mg (0.26 mmol) of 1-hydroxybenzotriazole and 50 mg (0.26 mmol) of 1-(3-dimethylaminopropyl)-3-ethylcarbodiimide hydrochloride were added. The solution was stirred for 2 hours at room temperature. The organic phase was washed with 5% (w/v) aqueous citric acid solution and then with saturated aqueous sodium bicarbonate solution, dried over magnesium sulphate and evaporated under a vacuum. The resulting oil was triturated with 10 ml of diethyl ether to give 160 mg of N2-[N-[N-[N-[N-[3-(tert-butoxycarbonyl) propionyl]-O-tert-butyl-L-α-aspartyl]-O-tert-butyl-L-α-glutamyl]-2-methyl-L-phenylalanyl]-3-methyl-L-valyl]-N1-[2-(butylthio)-[1(R)-(dimethoxymethyl)ethyl]-L-leucinamide as a white solid; MS: m/e 1075.6 [M+H–MeOH]$^+$.

EXAMPLE 12

56 mg (0.049 mmol) of N1-[2-(benzylthio)-1(R)-(dimethoxymethyl)ethyl]-N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucinamide were dissolved in 10 ml of trifluoroacetic acid/dichloromethane (1:1) containing 3 drops of water and the solution was stirred for 90 minutes. The solution was evaporated to dryness under a vacuum and the residue was re-evaporated twice with toluene. The solid was triturated with 10 ml of diethyl ether to give 40 mg of 3-(benzylthio)-2(R)-[[N-[N-[N-[N-(3-carboxypropionyl)-L-α-aspartyl]-L-α-glutamyl]-2-methyl-L-phenylalanyl]-3-methyl-L-valyl]-L-leucyl]amino] propionaldehyde as a white solid. MS: m/e 927.6 (M+H)$^+$.

The starting material was prepared as follows:

i) S-Benzyl-N-(tert-butoxycarbonyl)-L-cysteine was obtained in a manner analogous to that described in Example 10 i) from 1 g (4.74 mmol) of S-benzyl-L-cysteine, 0.8 g (9.5 mmol) of sodium bicarbonate and 1.4 g (6.4 mmol) of di-tert-butyl dicarbonate. There were obtained 1.4 g of a colourless oil; $^1$H NMR (250 MHz, CDCl$_3$) δ: 1.4 (s,9H), 2.8–2.9 (m,2H), 3.7 (s,2H), 4.4–4.5 (m,1H), 5.3 (d,1H), 7.2–7.4 (m,5H)

ii) N,O-Dimethyl 3-(benzyl)-2(R)-(tert-butoxyformamido) propionohydroxamate was obtained in a manner analogous to that described in Example 9 i) from 1.4 g (4.52 mmol) of S-benzyl-N-(tert-butoxycarbonyl)-L-cysteine, 0.70 g (4.6 mmol) of 1-hydroxybenzotriazole monohydrate, 1.30 g (6.77 mmol) of 1-(3-dimethylaminopropyl)-3-ethylcarbodiimide hydrochloride, 0.66 g (6.77 mmol) of N,O-dimethylhydroxylamine hydrochloride and 0.78 g (6.77 mmol) of N-ethylmorpholine in 40 ml of dichloromethane. There were obtained 0.60 g of a colourless oil; $^1$H NMR (250 MHz, CDCl$_3$) δ: 1.4 (s,9H), 2.55–2.65 (dd,1H), 2.75–2.85, (dd,1H), 3.2 (s,3H), 3.7 (s,3H), 3.72 (s,2H), 4.9 (m,1H), 5.3 (d,1H), 7.2–7.35 (m,5H).

iii) 0.48 g (1.36 mmol) of N,O-dimethyl 3-(benzyl)-2(R)-(tert-butoxyformamido)propionohydroxamate was dissolved in 10 ml of anhydrous tetrahydrofuran and the solution was cooled to 0° C. 0.95 ml (0.95 mmol) of a 1 M solution of lithium aluminium hydride in tetrahydrofuran was added dropwise and the mixture was stirred for 15 minutes. The reaction was quenched by the dropwise addition of saturated aqueous potassium hydrogen sulphate and then 20 ml of diethyl ether were added. The mixture was stirred vigorously for 20 minutes. The organic phase was separated, washed with saturated aqueous sodium bicarbonate solution, dried magnesium sulphate and evaporated to give the aldehyde which, without further purification, was dissolved in 10 ml of saturated methanolic hydrogen chloride solution and stirred for 2 hours at room temperature. The solvent was removed by evaporation and the residue was re-evaporated twice with toluene to give the amino acid acetal as a brown oil.

100 mg (0.36 mmol) of the amino acid acetal were dissolved in 40 ml of dichloromethane and then 200 mg (0.22 mmol) of N-[N-[N-[N-[3-(tert-butoxycarbonyl) propionyl]-O-tert-butyl-L-α-aspartyl]-O-tert-butyl-L-α-glutamyl]-2-methyl-L-phenylalanyl]-3-methyl-L-valyl]-L- leucine, 100 mg (0.87 mmol) of N-ethylmorpholine, 40 mg (0.30 mmol) of 1-hydroxybenzotriazole and 50 mg (0.26 mmol) of 1-(3-dimethylaminopropyl)-3-ethylcarbodiimide hydrochloride were added. The solution was stirred overnight at room temperature. The organic phase was washed with 5% (w/v) aqueous citric acid solution and then with saturated aqueous sodium bicarbonate solution, dried over magnesium sulphate and evaporated under a vacuum. The resulting oil was triturated with 10 ml of diethyl ether to give 160 mg of N1-[2-(benzylthio)-1(R)-(dimethoxymethyl) ethyl]-N2-[N-[N-[N-[3-(tert-butoxycarbonyl) propionyl]-O-tert-butyl-L-α-aspartyl]-O-tert-butyl-L-α-glutamyl]-2-methyl-L-phenylalanyl]-3-methyl-L-valyl]-L-leucinamide as a white solid; MS: m/e 1109.8 [M+H−MeOH]⁺.

EXAMPLE 13

49 mg (0.046 mmol) of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-3-pentynyl]-L-leucinamide were dissolved in 4 ml of trifluoroacetic acid/dichloromethane (1:1) containing 3 drops of water and the solution was stirred for 1 hour under a nitrogen atmosphere. The solution was evaporated to dryness under a vacuum and the residue was re-evaporated twice with toluene. The solid was triturated with 10 ml of diethyl ether to give 30 mg of 2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-4-hexynal as a white solid; MS: m/e 843.6 [M+H]⁺.

The starting material was prepared as follows:
i) N-(tert-Butoxycarbonyl)-L-(2-butynyl)glycine was obtained in a manner analogous to that described in Example 10 i) from 1.0 g (7.80 mmol) of L-(2-butynyl)glycine (prepared according to Sasaki et al. Int. J. Peptide Protein Res 1986, 27, 360–365), 2.66 g 1 5 (31.7 mmol) of sodium bicarbonate and 1.89 g (8.66 mmol) of di-tert-butyl dicarbonate. There was obtained 1.94 g of a colourless oil; ¹H NMR (250 MHz, CDCl₃) δ: 1.45 (s,9H), 1.75 (t,3H), 2.6–2.9 (m,2H), 4.4–4.5 (m,1H), 5.3 (br.d,1H).
ii) N,O-Dimethyl 2(S)-(tert-butoxyformamido)-4-hexynohydroxamate was obtained in a manner analogous to that described in Example 9 i) from 1.74 g (7.67 mmol) of N-(tert-butoxycarbonyl)-L-(2-butynyl)glycine, 1.45 g (9.5 mmol) of 1-hydroxybenzotriazole, 2.06 g (10.73 mmol) of 1-(3-dimethylaminopropyl)-3-ethylcarbodiimide hydrochloride, 1.05 g (10.77 mmol) of N,O-dimethylhydroxylamine hydrochloride and 5.3 ml (30.43 mmol) of ethyldiisopropylamine in 80 ml of tetrahydrofuran. There were obtained 2.0 g of a colourless oil; 1H NMR (250 MHz, CDCl₃) δ: 1.4 (s,9H), 1.75 (t,3H), 2.55 (m,2H), 3.2 (s,3H), 3.5 (s,3H), 4.7–4.8 (m,1H), 5.35 (br.d,1H).
iii) 1.0 g (3.70 mmol) of N,O-dimethyl 2(S)-(tert-butoxyformamido)-4-hexynohydroxamate was dissolved in 10 ml of anhydrous tetrahydrofuran and the solution was cooled to 0° C. 2.59 ml (2.59 mmol) of a 1M solution of lithium aluminium hydride in tetrahydrofuran were added dropwise and the mixture was stirred for 30 minutes. The reaction was quenched by the dropwise addition of 20 ml of saturated aqueous potassium hydrogen sulphate and then 50 ml of diethyl ether were added. The mixture was stirred vigorously for 30 minutes. The organic phase was separated, washed with saturated aqueous sodium bicarbonate solution, dried over magnesium sulphate and evaporated to give the aldehyde which, without further purification, was dissolved in 10 ml of saturated methanolic hydrogen chloride solution and stirred for 2 hours under a nitrogen atmosphere at room temperature. The solvent was removed by evaporation and the residue was re-evaporated twice with toluene to give the amino acid acetal as a brown oil.

47 mg (0.24 mmol) of the amino acid acetal were dissolved in 20 ml of dichloromethane and then 200 mg (0.22 mmol) of N-[N-[N-[N-[3-(tert-butoxycarbonyl) propionyl]-O-tert-butyl-L-α-aspartyl]-O-tert-butyl-L-α-glutamyl]-2-methyl-L-phenylalanyl]-3-methyl-L-valyl]-L-leucine, 0.1 ml (0.78 mmol) of N-ethylmorpholine, 42 mg (0.27 mmol) of 1-hydroxybenzotriazole and 59 mg (0.31 mmol) of 1-(3-dimethylaminopropyl)-3-ethylcarbodiimide hydrochloride were added. The solution was stirred overnight at room temperature. The organic phase was washed with 5% (w/v) aqueous citric acid solution and then with saturated aqueous sodium bicarbonate solution, dried over magnesium sulphate and evaporated under a vacuum. The resulting oil was triturated with 10 ml of diethyl ether to give 110 mg of N2-[N-[N-[N-[3-(tert-butoxycarbonyl) propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-3-pentynyl]-L-leucinamide as a white solid. MS: m/e 1025.8 [M+H−MeOH]⁺.

EXAMPLE 14

0.065 g (0.06 mmol) of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1 (RS)-(dimethoxymethyl)-2-(3-thienyl)ethyl]-L-leucinamide was dissolved in 10 ml of dichloromethane/trifluoroacetic acid (1:1) containing 3 drops of water. The solution was stirred for 3 hours at room temperature. After removal of the solvent by evaporation the crude product was chromatographed on silica gel using dichloromethane:methanol:acetic acid:water (120:15:3:2) as the eluent to give 0.035 g of 2(RS)-[[N-[N-[N-[N-[N-(3-carboxypropionyl)-L-α-aspartyl-L-α-glutamyl]-2-methyl-L-phenylalanyl]-3-methyl-L-valyl]-L-leucyl]amino]-3(3-thienyl)propionaldehyde as a white solid; MS: m/e 887.7 [M+H]⁺.

The starting material was prepared as follows:
i) 0.5 g (2.92 mmol) of 3-(3-thienyl)-DL-alanine was dissolved in 15 ml of water and 15 ml of dioxan. 2.5 g (29.76 mmol) of sodium hydrogen carbonate and 3.53 g (16.19 mmol) of di-tert-butyl dicarbonate were added and the solution was stirred for 2 hours and then evaporated to dryness under a vacuum. The residue was partitioned between diethyl ether and saturated aqueous sodium hydrogen carbonate solution. The aqueous phase was acidified with 2M hydrochloric acid and extracted with ethyl acetate. The organic phase was dried over magnesium sulphate and the solvent was evaporated under a vacuum to give 0.685 g of N-(tert-butoxycarbonyl)-3-(3-thienyl)-DL-alanine as a colourless oil; ¹H NMR (250 MHz, CDCl₃) δ: 1.4 (s,9H), 2.9 (dd,1H), 3.15 (dd,1H), 4.3 (m,1H), 7.0 (d,1H), 7.1 (br s,H), 7.3 (m,1H).
ii) 0.69 g (2.55 mmol) of N-(tert-butoxycarbonyl)-3-(3-thienyl)-DL-alanine was dissolved in 40 ml of dichloromethane. 0.34 g (3.56 mmol) of N,O-dimethylhydroxylamine hydrochloride, 0.54 g (3.53 mmol)

of 1-hydroxybenzotriazole monohydrate, 0.68 g (3.55 mmol) of 1-(3-dimethylaminopropyl)-3-ethylcarbodiimide hydrochloride and 1.0 g (8.70 mmol) of 4-ethylmorpholine were added and the resulting solution was stirred at room temperature overnight. The solution was then washed with 5% citric acid solution, saturated sodium hydrogen carbonate solution and saturated sodium chloride solution and dried over anhydrous magnesium sulphate. After evaporation of the solvent the crude product was chromatographed on silica gel using 30% ethyl acetate in petroleum ether as the eluent to give 0.75 g of N,O-dimethyl 2(RS)-(tert-butoxyformamido)-3-(3-thienyl)propionohydroxamate as a white solid; $^1$H NMR (250 MHz, CDCl$_3$) δ: 1.4 (s,9H), 2.95 (dd,1H), 3.05 (dd,1H), 3.15 (s,3H), 3.65 (s,3H), 4.9 (m,1H), 5.15 (br d,1H), 6.9 (d,1H), 7.0 (d,1H), 7.2 (m,1H).

iii) 0.2 g (0.64 mmol) of N,O-dimethyl 2(RS)-(tert-butoxyformamido)-3-(3-thienyl)propionohydroxamate was dissolved in 10 ml of anhydrous tetrahydrofuran and the solution was cooled to 0° C. 0.5 ml (0.5 mmol) of a 1M solution of lithium aluminium hydride in tetrahydrofuran was added dropwise and the solution was stirred for 15 minutes. The reaction was quenched by the dropwise addition of saturated potassium hydrogen sulphate solution and then 30 ml of diethyl ether were added. The resulting two phase system was stirred vigorously for 1 hour. The organic phase was separated, washed with saturated sodium hydrogen carbonate solution and saturated sodium chloride solution, dried over magnesium sulphate and evaporated to give the aldehyde which, without purification, was dissolved in 10 ml of a saturated methanolic hydrogen chloride solution and stirred at room temperature for 2 hours. After removal of the solvent by evaporation the dimethyl acetal was used in the next step without purification.

The dimethyl acetal was dissolved in 40 ml of dichloromethane and then 0.15 g (0.16 mmol) of N-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine, 0.03 g (0.2 mmol) of 1-hydroxybenzotriazole, 0.038 g (0.2 mmol) of 1-(3-dimethylaminopropyl)-3-ethylcarbodiimide hydrochloride and 0.08 g (0.65 mmol) of N-ethylmorpholine were added and the resulting solution was stirred at room temperature for 2 hours. The solution was washed with 5% citric acid solution, saturated sodium hydrogen carbonate solution and saturated sodium chloride solution and dried over anhydrous magnesium sulphate. After removal of the solvent by evaporation the crude product was chromatographed on silica gel using 5% methanol in dichloromethane as the eluent to give 0.07 g of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(RS)-(dimethoxymethyl)-2-(3-thienyl)ethyl-L-leucinamide as a white solid; MS: m/e 1069 [M+H–MeOH]$^+$.

EXAMPLE 15

0.08 g (0.07 mmol) of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N 1-[1(S)-(dimethoxymethyl)-2-(2-thienyl)ethyl]-L-leucinamide was dissolved in 10 ml of dichloromethane/trifluoroacetic acid (1:1) containing 3 drops of water and the solution was stirred for 2 hours at room temperature. After removal of the solvent by evaporation the crude product was chromatographed on silica gel using dichloromethane:methanol:acetic acid:water (120:15:3:2) as the eluent to give 0.021 g of 2(S)-[[N-[N-[N-[N-[N-(3-carboxypropionyl)-L-α-aspartyl-L-α-glutamyl]-2-methyl-L-phenylalanyl]-3-methyl-L-valyl]-L-leucyl]amino]-3(2-thienyl)propionaldehyde as a white solid; MS: m/e 887.4 [M+H]$^+$.

The starting material was prepared as follows:

i) 0.63 g (2.33 mmol) of N-(tert-butoxycarbonyl)-3-(2-thienyl)-L-alanine was dissolved in 50 ml of dichloromethane and then 0.34 g (3.48 mmol) of N,O-dimethylhydroxylamine hydrochloride, 0.36 g (2.35 mmol) of 1-hydroxybenzotriazole monohydrate, 0.67 g (3.49 mmol) of 1-(3-dimethylaminopropyl)-3-ethylcarbodiimide hydrochloride and 0.40 g (3.47 mmol) of N-ethylmorpholine were added. The resulting solution was stirred at room temperature overnight. The solution was washed with 5% citric acid, then with saturated sodium hydrogen carbonate solution and saturated sodium chloride solution, dried over anhydrous magnesium sulphate and evaporated to give 0.70 g of N,O-dimethyl 2(S)-(tert-butoxyformamido)-3-(2-thienyl)propionohydroxamate as a white solid; $^1$H NMR (250 MHz, CDCl$_3$) δ: 1.4 (s,9H), 3.1 (dd,1H), 3.15 (s,3H), 3.2 (dd,1H), 3.7 (s,3H), 4.9 (br d,1H), 5.8 (m,1H), 6.8 (d,1H), 6.9 (dd,1H), 7.15 (d,1H).

ii) 0.4 g (1.27 mmol) of N,O-dimethyl 2(S)-(tert-butoxyformamido)-3-(2-thienyl)propionohydroxamate was dissolved in 10 ml of anhydrous tetrahydrofuran and the solution was cooled to 0° C. 0.9 ml (0.9 mmol) of a 1M solution of lithium aluminium hydride in tetrahydrofuran was added and the resulting solution stirred for 15 minutes. The reaction was quenched by the dropwise addition of 15 ml of saturated potassium hydrogen sulphate solution and then 30 ml of diethyl ether were added. The resulting two phase system was stirred vigorously for 40 minutes. The organic phase was separated, washed with saturated sodium hydrogen carbonate solution and saturated sodium chloride solution and dried over anhydrous magnesium sulphate. After removal of the solvent by evaporation the aldehyde, without further purification, was dissolved in 10 ml of a saturated methanolic hydrogen chloride solution and stirred at room temperature for 2 hours. After removal of the solvent by evaporation the dimethyl acetal was used in the next step without purification.

The dimethyl acetal was dissolved in 40 ml of dichloromethane and then 0.20 g (0.22 mmol) of N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine, 0.04 mg (0.26 mmol) of 1-hydroxybenzotriazole, 0.05 g (0.26 mmol) of 1-(3-dimethylaminopropyl)-3-ethylcarbodiimide hydrochloride and 0.10 g (0.87 mmol) of N-ethylmorpholine were added. The resulting solution was stirred at room temperature for 2 hours, then washed in sequence with 5% citric acid solution, saturated sodium hydrogen carbonate solution and saturated sodium chloride solution and dried over anhydrous magnesium sulphate. After removal of the solvent by evaporation the crude product was triturated with diethyl ether to give 0.16 g of N2-[N-[N-[N-[N-[3-(tert-butoxycarbonyl) propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-2-(2-thienyl)ethyl-L-leucinamide as a white solid. MS: m/e 1069.6 [M+H–MeOH]+$^+$.

EXAMPLE 16

In an analogous manner to that described in Example 4, by replacing N-[(9-fluorenyl)methoxycarbonyl]-3-(2- naphthyl)-D-alanine with N-[(9-fluorenyl) methoxycarbonyl]-L-cyclohexyl-glycine there was obtained 2(RS)-[[N-[N-[N-[N-(3-carboxypropionyl)-L-α-aspartyl]-L-2-cyclohexylglycyl]-2-methyl-L-phenylalanyl]-3-methyl-L-valyl]-L-leucyl]amino]-4,4,4-trifluorobutyraldehyde as a white solid; MS: m/e 883.5 [M+H].

EXAMPLE 17

In an analogous manner to that described in Example 4, by replacing N-[(9-fluorenyl)methoxycarbonyl]-3-(2-naphthyl)-D-alanine with N-[(9-fluorenyl) methoxycarbonyl]-L-valine there was obtained 2(RS)-[[N-[N-[N-[N-(3-carboxypropionyl)-L-α-aspartyl]-L-valyl]-2-methyl-L-phenylalanyl]-3-methyl-L-valyl]-L-leucyl] amino]-4,4,4-trifluorobutyraldehyde as a white solid; MS: m/e 843.5 [M+H].

EXAMPLE 18

In an analogous manner to that described in Example 4, by replacing N-[(9-fluorenyl)methoxycarbonyl]-3-(2-naphthyl)-D-alanine with N-[(9-fluorenyl) methoxycarbonyl]-D-alanine there was obtained 2(RS)-[[N-[N-[N-[N-(3-carboxypropionyl)-L-α-aspartyl]-D-alanyl]-2-methyl-L-phenylalanyl]-3-methyl-L-valyl]-L-leucyl]amino]-4,4,4-trifluorobutyraldehyde as a white solid; MS: m/e 815.4 [M+H].

EXAMPLE 19

In an analogous manner to that described in Example 4, by replacing N-[(9-fluorenyl)methoxycarbonyl]-3-(2-naphthyl)-D-alanine with N-[(9-fluorenyl) methoxycarbonyl]-D-valine there was obtained 2(RS)-[[N-[N-[N-[N-(3-carboxypropionyl)-L-α-aspartyl]-D-valyl]-2-methyl-L-phenylalanyl]-3-methyl-L-valyl]-L-leucyl] amino]-4,4,4-trifluorobutyraldehyde as a white solid; MS: m/e 843.4 [M+H].

EXAMPLE 20

0.2 g (0.2 mmol) of N2-[N-[N-[N-[N-(carboxypropionyl)-L-α-aspartyl]-L-α-glutamyl]-2-methyl-L-phenylalanyl]-3-methyl-L-valyl]-N1-[1(R)-(3a(S),4(S),5,6(S),7,7a(R)-hexahydro-3a,5,5-trimethyl-4,6-methano-1,3,2-benzodioxaborol-2-yl)pentyl]-L-leucinamide was dissolved in 12 ml of acetone and 12 ml of 0.1M ammonium acetate in water were added. 0.21 g (1 mmol) of sodium periodate was added and the resulting mixture was stirred at room temperature for 22 hours. 7 ml of water were then added together with a small amount of sodium periodate. The resulting solution was stirred for a further 5 hours. The acetone was removed under a vacuum and the aqueous residue was acidified with 2N hydrochloric acid and then extracted with ethyl acetate. Saturated aqueous sodium chloride was added to the aqueous layer which was then extracted with ethyl acetate. The organic extracts were combined, dried over sodium sulphate and evaporated. The residue was trituated with diethyl ether, filtered off and dried to give 167 mg of 1 (R)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino] pentylboronic acid as a white solid; MS: m/e 845.4 [M+H-H$_2$O]$^+$.

The starting material was prepared as follows:

i) In an analogous manner to that described in Example 21 i) and ii), by replacing 3-butenylmagnesium bromide with butylmagnesium bromide there was obtained α-(R)-butyl-3a(S),4(S), 5,6(S),7,7a(R)-hexahydro-3a,5,5-trimethyl-4,6-methano-1,3,2-benzodioxaborole-2-methylamine trifluoroacetate (1:1) which was used in the next step without further purification.

ii) 0.25 g (0.27 mmol) of N-[N-[N-[N-(tert-butoxycarbonyl)-O-tert-butyl-L-α-aspartyl]-O-tert-butyl-L-a-glutamyl]-2-methyl-L-phenylalanyl]-3-methyl-L-valyl]-L-leucine was dissolved in 2 ml of dimethylformamide and 4 ml of dichloromethane. 0.15 ml (1.4 mmol) of N-methylmorpholine was added and the solution was cooled to −10° C. under a nitrogen atmosphere. 45 mg (0.32 mmol) of isobutyl chloroformate were added and the solution was stirred for 10 minutes at −10° C. 0.2 g (0.54 mmol) of α-(R)-butyl-3a(S),4(S),5,6(S),7,7a(R)-hexahydro-3a,5,5-trimethyl-4,6-methano-1,3,2-benzodioxaborole-2-methylamine trifluoroacetate (1.1) was added and the mixture was stirred at room temperature for 16 hours. The solution was diluted with dichloromethane, washed with 2M hydrochloric acid and water and dried over anhydrous sodium sulphate. After evaporation the residue was triturated with diethyl ether and dried. There was obtained 0.227 g of N2-[N-[N-[N-[N-[3-(tert-butoxycarbonyl)propionyl]-O-tert-butyl-L-a-aspartyl]-O-tert-butyl-L-α-glutamyl]-2-methyl-L-phenylalanyl]-3-methyl-L-valyl]-N1-[1(R)-(3a (S), 4(S),5,6(S), 7,7a(R)-hexahydro-3a,5,5-trimethyl-4,6-methano-1,3,2-benzodioxaborol-2-yl)pentyl]-L-leucinamide as a white solid; MS: m/e 1165.9 [M+H]$^+$.

iii) 300 mg (0.26 mmol) of N2-[N-[N-[N-[N-(tert-butoxycarbonyl)-O-tert-butyl-L-α-aspartyl]-O-tert-butyl-L-α-glutamyl]-2-methyl-L-phenylalanyl]-3-methyl-L-valyl]-N1-[1(R)-(3a(S),4(S),5,6(S),7,7a(R)-hexahydro-3a,5,5-trimethyl-4,6-methano-1,3,2-benzodioxaborol-2-yl)-4-pentenyl]-L-leucinamide were dissolved in 3.5 ml of trifluoroacetic acid and 3.5 ml of dichloromethane. The solution was stirred at room temperature for 45 minutes, then diluted with toluene and evaporated. The residue was triturated with diethyl ether and the resulting solid was filtered off and dried and then purified by chromatography on silica gel using dichlomethane/methanol/acetic acid/water (170:15:3:2) for the elution. There were obtained 135 mg of N2-[N-[N-[N-[N-(3-carboxypropionyl)-L-α-aspartyl]-L-a-glutamyl]-2-methyl-L-phenylalanyl]-3-methyl-L-valyl]-N1-[1(R)-(3a(S), 4(S),5,6(S),7,7a(R)-hexahydro-3a,5,5-trimethyl-4,6-methano-1 ,3,2-benzodioxaborol-2-yl)-4-pentenyl]-L-leucinamide as a white solid: MS: m/e 995.3 [M+H]$^+$.

EXAMPLE 21

N2-[N-[N-[N-[N-(3-Carboxypropionyl)-L-α-aspartyl]-L-α-glutamyl]-2-methyl-L-phenylalanyl]-3-methyl-L-valyl]-N1-[1 (R)-(3a(S),4(S),5,6(S),7,7a(R)-hexahydro-3a,5,5-trimethyl-4,6-methano-1,3,2-benzodioxaborol-2-yl)-4-pentenyl]-L-leucinamide can be converted into N2-[N-[N-[N-[N-(3-carboxypropionyl)-L-α-aspartyl]-L-α-glutamyl]-2-methyl-L-phenylalanyl]-3-methyl-L-valyl]-L-leucyl] amino]-4-pentenylboronic acid in an analogous manner to that described in the first paragraph of Example 20.

The starting material was prepared as follows:

i) 0.5 g (1.9 mmol) of 2-(dichloromethyl)-3a(S),4(S),5,6(S), 7,7a(R)-hexahydro-3a,5,5-trimethyl-4,6-methano-1 ,3,2-benzodioxaborole was dissolved in 5 ml of tetrahydrofuran and the solution was cooled to −78° C. under a nitrogen atmosphere. 4.5 ml (2.3 mmol) of 0.5M 3-butenylmagnesium bromide in tetrahydrofuran were added dropwise and the resulting solution was stirred for 2 minutes. 3 ml (1.52 mmol) of 0.5M zinc (II) chloride solution were then added and the mixture was stirred for 16 hours while slowly warming to room temperature. The mixture was diluted with ethyl acetate and then washed with 2M hydrochloric acid and brine. The organic phase was dried over sodium sulphate and then evaporated under a vacuum. The residue was purified by chromatography on silica gel using diethyl ether/hexane (1:9) for the elution to give 177 mg of 2-[1(S)-chloro-4-pentenyl]-3a(S)-4(S),5,6 (S),7,7a(R)-hexahydro-3a,5,5-trimethyl-4,6-methano-1,3,2-benzodioxaborole. NMR: (CDCl$_3$) 0.83 (s, 3H), 1.15 (d, 1H, 1.30 (s, 3H), 1.42 (s, 3H), 1.42 (s, 3H), 1.85–1.95 (m, 4H), 2.08 (t, 1H), 2.15–2.35 (m, 4H), 3.49 (dd, 1H), 4.35 (dd, 1H), 5.0 (dd, 1H), 5.07 (dd, 1H), 5.78 (m, 1 H).

ii) 0.158 g (0.56 mmol) of 2-[1(S)-chloro-4-pentenyl]-(3a (S),5,6(S),7,7a(R)-hexahydro-3a,5,5-trimethyl-4,6-methano-1,3,2-benzodioxaborole was dissolved in 2 ml of tetrahydrofuran and then cooled to −78° C. under a nitrogen atmosphere. 0.56 ml (0.56 mmol) of 1M lithium bis (trimethylsilyl)amide in tetrahydrofuran was added dropwise. The solution was then stirred overnight while slowly warming to room temperature. The solvent was removed by evaporation and the residue was taken up in diethyl ether. Insoluble material was removed by filtration. The solvent was removed by evaporation, the residue was dissolved in 2 ml of diethyl ether and the solution was cooled to 0° C. 0.12 ml (1.7 mmol) of trifluoroacetic acid was added and the solution was stirred at 0° C. for 30 minutes. The solution was evaporated and the residue was co-evaporated with toluene to give 0.0226 g of a-(R)-(3-butenyl)-3a(S),4(S),5,6(S),7,7a(R)-hexahydro-3a,5,5-trimethyl-4,6-methano-1,3,2-benzodioxaborole-2-methylamine trifluoroacetate (1:1) as an oil which was used in the next step without further purification.

iii) 0.35 g (0.38 mmol) of N-[N-[N-[N-(tert-butoxycarbonyl)-O-tert-butyl-L-α-aspartyl]-O-tert-butyl-L-α-glutamyl]-2-methyl-L-phenylalanyl]-3-methyl-L-valyl]-L-leucine was dissolved in 2 ml of dimethylformamide and 6 ml of dichloromethane. 0.21 ml (1.9 mmol) of N-methylmorpholine was added and the solution was cooled to −15° C. under a nitrogen atmosphere. 66 mg (0.46 mmol) of isobutyl chloroformate were added and the solution was stirred for 10 minutes at −15° C. 0.2 g (0.53 mmol) of α-(R)-(3-butenyl)-3a(S),4(S),5,6(S),7,7a(R)-hexahydro-3a, 5,5-trimethyl-4,6-methano-1,3,2-benzoxaborole-2-methylamine trifluoroacetate (1.1) was added and the mixture was stirred at room temperature for 5 hours. The solution was diluted with dichloromethane, washed with 2M hydrochloric acid and water and dried over anhydrous sodium sulphate. After evaporation the residue was triturated with diethyl ether and dried. There was obtained 0.309 g of N2-[N-[N-[N-[N-(tert-butoxycarbonyl)-O-tert-butyl-L-α-aspartyl]-O-tert-butyl-L-α-glutamyl]-2-methyl-L-phenylalanyl]-3-methyl-L-valyl]-N1-[1(R)-(3a(S),4(S),5,6 (S),7,7a(S)-hexahydro-3a,5,5-trimethyl-4,6-methano-1,3,2-benzodioxaborol-2-yl)-4-pentenyl-L-leucinamide as as solid which was used without further purification.

iv) 300 mg (0.26 mmol) of N2-[N-[N-[N-[N-(tert-butoxycarbonyl)-O-tert-butyl-L-α-aspartyl]-O-tert-butyl-L-α-glutamyl]-2-methyl-L-phenylalanyl]-3-methyl-L-valyl]-N1-[1(R)-(3a(S),4(S),5,6(S),7,7a(R)-hexahydro-3a,5,5-trimethyl-4,6-methano-1,3,2-benzodioxaborol-2-yl)-4-pentenyl]-L-leucinamide were dissolved in 3.5 ml of trifluoroacetic acid and 3.5 ml of dichloromethane. The solution was stirred at room temperature for 45 minutes, then diluted with toluene and evaporated. The residue was triturated with diethyl ether and the resulting solid was filtered off and dried and then purified by chromatography on silica gel using dichlomethane/methanol/acetic acid/water (170:15:3:2) for the elution. There were obtained 135 mg of N2-[N-[N-[N-[N-(3-carboxypropionyl)-L-α-aspartyl]-L-α-glutamyl]-2-methyl-L-phenylalanyl]-3-methyl-L-valyl]-N1-[1(R)-(3a(S), 4(S),5,6(S),7,7a(R)-hexahydro-3a,5,5-trimethyl-4,6-methano-1 ,3,2-benzodioxaborol-2-yl)-4-pentenyl]-L-leucinamide as a white solid: MS: m/e 995.3 [M+H]$^+$

EXAMPLE 22

N2-[N-[N-[N-[N-(3-Carboxypropionyl)-L-α-aspartyl]-L-α-gluatamyl]-2-methyl-L-phenylalanyl]-3-methyl-L-valyl]-N1-[1(R)-(3a(S),4(S),5,6(S),7,7a(R)-hexahydro-3a,5,5-trimethyl-4,6-methano-1,3,2-benzodioxaborol-2-yl)propyl]-L-leucinamide can be converted into 1 (R)-[[N-[N-[N-[N-(3-carboxypropionyl)-L-α-aspartyl]-L-α-glutamyl]-2-methyl-L-phenylalanyl]-3-methyl-L-valyl]-L-leucyl]amino] propylboronic acid in a manner analogous to that described in the first paragraph of Example 20.

The starting material was prepared as follows:

i) In an analogous manner to that described in Example 21 i) and ii), by replacing 3-butenylmagnesium bromide with ethylmagnesium bromide there was obtained α(R)-ethyl-3a (R)-ethyl-3a(S),4,(S),5,6(S),7,7a(R)-hexahydro-3a,5,5-trimethyl-4,6-methano-1,3,2-benzodioxaborole-2-methylamine trifluoroacetate (1:1) which was used in the next step without further purification.

ii) 0.35 g (0.38 mmol) of N-[N-[N-[N-(tert-butoxycarbonyl)-O-tert-butyl-L-α-aspartyl]-O-tert-butyl-L-α-glutamyl]-2-methyl-L-phenylalanyl-3-methyl-L-valyl]-L-valyl]-L-leucine was dissolved in 3 ml of dimethylformamide and 7 ml of dichloromethane. 0.2 ml (1.9 mmol) of N-methylmorpholine was added and the solution was cooled to −10° C. under a nitrogen atmosphere. 68 mg (0.53 mmol) of isobutyl chloroformate were added and the solution was stirred for 10 minutes at −10° C. 0.18 g (0.53 mmol) of α(R)-ethyl-3a(S)4(S),5,6,(S),7,7a(R)-hexahydro-3a,5,5-trimethyl-4,6-methano-1,3,2-benzodioxaborole-2-methylamine trifluoroacetate (1:1) was added and the mixture was stirred at room temperature for 16 hours. After evaporation the residue was partitioned between ethyl acetate and 2M hydrochloric acid. The organic layer was washed with water and saturated sodium chloride solution and then dried over anhydrous sodium sulphate. The solution was evaporated and the residue was trituated with diethyl ether, filtered off and dried to give 0.22 g of N2-[N-[N-[N-[3-(tert-butoxycarbonyl)-propionyl]-O-tert-butyl-L-α-aspartyl]-O-tert-butyl-L-α-glutamyl]-2-methyl-L-phenylalanyl]-3-methyl-L-valyl]-N1-[1(R)-(3a (S),4(S),5,6(S),7,7a(R)-hexahydro-3a,5,5-trimethyl-4,6-methano-1,3,2-benzodioxaborol-2-yl)propyl]-L-leucinamide as a solid which was used without further purification.

iii) 0.22 g (0.19 mmol) of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(R)-3a(S),4(S),5,6,(S),7,7a(R)-hexahydro-3a,5,5-trimethyl-4,6-methano-1,3,2-benzodioxaborol-2-yl) propyl]-L-leucinamide was dissolved in 5 ml of trifluoroacetic acid and 5 ml of dichloromethane, the solution was stirred at room temperature for 1 hour and then diluted with toluene and evaporated. The residue was triturated with diethyl ether and the resulting solid was filtered off and dried to give 170 mg of N2-[N-[N-[N-[N-(3-carboxypropionyl]-L-α-aspartyl]-L-α-gluatamyl]-2-methyl-L-phenylalanyl]-3-methyl-L-valyl]-N1-[1(R)-(3a(S),4(S),5,6(S),7,7a(R)-hexahydro-3a, 5,5-trimethyl-4,6-methano-1,3,2-benzodioxaborol-2-yl)propyl]-L-leucinamide as a white solid; MS: m/e 969.4 [M+H]$^+$.

EXAMPLE 23

4 g of 0.25 mmol/g 5-[2-[1 (RS)-[[N-[(9-fluorenyl)methoxy-carbonyl]-L-leucyl]amino]propyl]-4(RS),5,5-trimethyl-1,3,2-dioxoborolan-4-yl]-3(RS)-methyl-N-[a(RS)-(4-methylphenyl)benzyl]valeramide-polystyrene conjugate were swollen in dimethylformamide for 20 minutes and then suspended and agitated in dimethylformamide/piperidine (4.1). After 5 minutes the resin was drained and then suspended in and agitated with dimethylformamide/piperidine (4.1) for a further 5 minutes. The resin was then drained and washed five times with dimethylformamide.

The resin was then suspended in a solution of 2.1 g (6 mmol) of N-[(9-fluorenyl)methoxycarbonyl]-3-methyl-L-valine in dimethylformamide and then a mixture of 1.9 g of 2-(1H-benzotriazol-1 -yl)-1,1,3,3-tetramethyluronium tetrafluoroborate and 1.3 ml of N-methylmorpholine dissolved in dimethylformamide was added. After agitating for 40 minutes the resin was drained and washed five times with dimethylformamide.

The resin was resuspended in and agitated with dimethylformamide/piperidine (4:1). After 5 minutes the resin was drained and resuspended in and agitated with dimethylformamide/piperidine (4:1) for a further 5 minutes. Then, the residue was drained and washed five times with dimethyl formamide.

The resin was then suspended in a solution of 2.4 g (6 mmol) of N-[(9-fluorenyl)methoxycarbonyl]-3-(2-methylphenyl)-L-alanine in dimethylformamide and a mixture of 1.9 g of 2(1H-benzotriazol-1-yl)-1,1,3,3-tetramethyluronium tetrafluoroborate and 1.3 ml of N-methylmorpholine dissolved in dimethylformamide was added. After agitating for 40 minutes the resin was drained and washed five times with dimethyl formamide.

40 mg of this resin were resuspended in and agitated with 0.7 ml of dimethylformamide/piperidine (4:1). After 5 minutes the resin was drained and resuspended in and agitated with dimethylformamide/piperidine (4:1) for a further 5 minutes. Then, the resin was drained and washed five times with dimethylformamide.

The resin was then suspended in 0.5 ml of a 0.2M solution of N-[(9-fluorenyl)methoxycarbonyl]-O-tert-butyl-L-α-glutamic acid in dimethyl sulphoxide and then 0.5 ml of a mixture of 0.2M 2-(1H-benzotriazol-1 -yl)-1 ,1,3,3-tetramethyluronium tetrafluoroborate and 0.4M N-methylmorpholine in dimethylformamide was added. After agitating for 1 hour the resin was drained and washed five times with 1 ml of dimethylformamide The resin was resuspended in and agitated with 0.7 ml of dimethylformamide/piperidine (4:1). After 5 minutes the resin was drained and resuspended in and agitated with dimethylformamide/piperidine (4:1) for a further 5 minutes. Then, the resin was drained and washed five times with 1 ml of dimethylformamide.

The resin was suspended in 0.5 ml of a solution of N-(9-fluorenylmethoxycarbonyl)-O-tert-butyl-L-tyrosine in dimethyl sulphoxide and 0.5 ml of a mixture of 0.2M 2-(1H-benzotriazol-1-yl)-1,1,3,3-tetramethyluronium tetrafluoroborate and 0.4M N-methylmorpholine in dimethylformamide was added. After agitating for 1 hour the resin was drained and washed five times with 1 ml of dimethylformamide.

The resin was resuspended in and agitated with 0.7 ml of dimethylformamide/piperidine (4:1). After 5 minutes the resin was drained and resuspended in and agitated with dimethylformamide/piperidine (4:1) for a further 5 minutes. Then, the resin was drained and washed five times with 1 ml of dimethylformamide.

The residue was suspended in 0.5 ml of a 0.2M solution of tert-butyl hydrogen succinate in dimethylformamide and then 0.5 ml of 0.2M 2-(1H-benzotriazol-1-yl)-1,1,3,3-tetramethyluronium tetrafluoroborate and 0.4M N-methylmorpholine dissolved in dimethylformamide was added. After agitating for 1 hour the resin was drained and washed five times with 1 ml of dimethylformamide and then twice with 1 ml of dichloromethane.

0.2 ml of dichloromethane was added to the resin which was then treated with 0.7 ml of trifluoroacetic acid/water (19:1) and agitated for 90 minutes. The resin was then filtered off and washed with 0.7 ml of trifluoroacetic acid/water (19:1). The combined trifluoroacetic acid and water solutions were then evaporated in a vacuum centrifuge and the residue was suspended in acetonitrile/water (1:1) and freeze dried. There were obtained 16.8 mg of 1(RS)-[[N-[N-[N-[N-[N-(3-carboxypropionyl)-L-tyrosyl]-L-α-glutamyl]-2-methyl-L-phenylalanyl]-3-methyl-L-valyl]-L-leucyl]amino]propylboronic acid as a white solid; MS m/e 807.4 [M+H–H$_2$O]$^+$.

The starting material was prepared as follows:

i) 25 ml of isobutylene were condensed at –78° C. and added to a mixture of 19.4 g (114 mmol) of 3(RS),7-dimethyl-6-octenoic acid and 1 ml of concentrated sulphuric acid in 25 ml of dichloromethane. The mixture was stirred for 24 hours under a dry ice condenser. A further 20 ml of isobutylene were added and the mixture was stirred for 24 hours under a dry ice condenser. The mixture was diluted with dichloromethane, washed with saturated sodium bicarbonate solution, dried over anhydrous magnesium sulphate and evaporated under a vacuum. The resulting oil was purified by chromatography on silica gel using ethyl acetate/hexane (1:9) for the elution. There were obtained 20.8 g of tert-butyl 3(RS),7-dimethyl-6-octenoate as a colourless oil. $^1$H NMR (250 MHz, CDCl$_3$) d: 0.9 (d, 3H), 1.1–1.3 (m, 3H), 1.4 (s, 9H), 1.6 (s, 3H), 1.65, (s, 3H), 1.8–2.2 (br m, 4H), 5.05, (m, 1H).

ii) 1.5 g (6.64 mmol) of tert-butyl 3(RS),7-dimethyl-6-octenoate were dissolved in a mixture of 10 ml of acetone, 2 ml of water and 2 ml of glacial acetic acid. 2 g (12.6 mmol) of potassium permanganate were added and the resulting mixture was stirred at 30° C. for 2 hours. 22 ml of 2M sulphuric acid and 0.8 g (11.3 mmol) of sodium nitrite were added and the organic phase was separated. The aqueous phase was extracted with dichloromethane and the combined organic phases were washed with water, dried over magnesium sulphate and evaporated under a vacuum to give 1.55 g of tert-butyl 7-hydroxy-3(RS),7-dimethyl6-oxo-octenoate as a clear oil; MS: m/e 259 [M+H]$^+$.

iii) 0.25 g (0.97 mmol) of tert-butyl 7-hydroxy-3(RS),7-dimethyl-6-oxo-octenoate was dissolved in 3 ml of diethyl ether at 0° C. under a nitrogen atmosphere. 0.36 ml (1.1 mmol) of 3M methylmagnesium bromide in diethyl ether was added dropwise and the resulting solution was stirred at 0° C. for 2 hours, refluxed for 6 hours and then stirred at room temperature for 16 hours. The solution was diluted with ethyl acetate and then extracted with 2M hydrochloric acid and saturated sodium chloride solution. The organic phase was dried over anhydrous sodium sulphate and evaporated under a vacuum. The resulting oil was purified by chromatography on silica gel using ethyl acetate/ hexane (1:2) for the elution. There were obtained 118 mg of tert-butyl 6(RS),7-dihydroxy-3(RS),6,7-trimethyl-6-octenoate as a clear oil; MS: m/e 275 [M+H]+.

iv) 0.64 g (2.3 mmol) of tert-butyl 6(RS),7-dihydroxy-3-(RS), 6,7-trimethyl-6-octenoate was stirred in 3 ml of tetrahydrofuran with 0.5 g (2.5 mmol) of dichloromethyl diisopropoxyborane at room temperature for 16 hours. The resulting mixture was evaporated and the residue was co-evaporated with toluene to give 0.86 g of tert-butyl 5-[2-(dichloromethyl)-4(RS),5,5-trimethyl-1,3,2-dioxaborolan-4-yl]-3(RS)-methylvalerate as an oil which was used in the next step without further purification.

v) 0.86 g (2.3 mmol) of tert-butyl 5-[2-(dichloromethyl)-4 (RS), 5,5-trimethyl-1,3,2-dioxaborolan-4-yl]-3(RS)-methylvalerate was dissolved in 5 ml of tetrahydrofuran and the solution was cooled to −78° C. under a nitrogen atmosphere. 2.6 ml (2.6 mmol) of 1M ethylmagnesium bromide in tetrahydrofuran were added dropwise, the resulting solution was stirred for 16 hours while slowly warming to room temperature and then diluted with ethyl acetate and extracted with 2M hydrochloric acid and brine. The organic phase was dried over sodium sulphate and then evporated under a vacuum to give 0.83 g of tert-butyl 5-[2-(1(RS)-chloropropyl)-4(RS),5,5-trimethyl-1 ,3,2-dioxaborolan-4-yl]-3(RS)-methylvalerate as an oil which was used in the next step without purification.

vi) 0.82 g (2.27 mmol) of tert-butyl 5-[2-(1(RS)-chloropropyl)-4(RS),5,5-trimethyl-1 ,3,2-dioxaborolan-4-yl]-3(RS)-methylvalerate was dissolved in 10 ml of tetrahydrofuran and then cooled to −78° C. under a nitrogen atmosphere. 2.3 ml (2.3 mmol) of 1M lithium bis(trimethylsilyl)amide in tetrahydrofuran were added dropwise. The solution was then stirred overnight while slowly warming to room temperature. The solvent was removed by evaporation and the residue was taken up in diethyl ether. Insoluble material was removed by filtration and the filtrate was cooled to 0° C. 0.52 ml (6.8 mmol) of trifluoroacetic acid was added and the solution was stirred at 0° C. for 30 minutes. The solution was evaporated and the residue was co-evaporated with toluene to give 1 g of tert-butyl 5-[2-(1 (RS)-aminopropyl)-4(RS), 5,5-trimethyl-1 ,3,2-dioxaborolan-4-yl]-3(RS)-methylvalerate as an oil which was used in the next step without purification.

vii) 0.5 g (1.42 mmol) of N-[(9-fluorenyl)methoxycarbonyl]-L-leucine was dissolved in 7 ml of dichloromethane. 0.6 ml (5.7 mmol) of N-methylmorpholine was added and the solution was cooled to −10° C. under a nitrogen atmosphere. 0.22 ml (1.7 mmol) of isobutyl chloroformate was added and the solution was stirred for 7 minutes at −10° C. 1 g (2.13 mmol) of tert-butyl 5-[2-(1 (RS)-aminopropyl)-4(RS),5,5-trimethyl-1,3,2-dioxaborolan-4-yl]-3(RS)-methylvalerate was added and the mixture was stirred at room temperature for 16 hours, then diluted with dichloromethane and extracted with 2M hydrochloric acid. The organic phase was extracted with 2M hydrochloric acid and saturated sodium hydrogen carbonate solution and then dried over anhydrous magnesium sulphate. After evaporation the residue was purified by chromatography on silica gel using ethyl acetate/hexane (1:2) for the elution. There was obtained 0.56 g of tert-butyl 5-[2-[1(RS)-[[N-[(9-fluorenyl)methoxycarbonyl]-L-leucyl]amino]propyl]-4(RS) ,5,5-trimethyl-1,3,2-dioxaborolan-4-yl]-3(RS)-methylvalerate as an oil; MS: m/e 677 [M+H]+.

viii) 50 mg (0.074 mmol) of tert-butyl 5-[2-[1(RS)-[[N-[(9-fluorenyl)methoxycarbonyl]-L-leucyl]amino]propyl]-4(RS) ,5,5-trimethyl-1,3,2-dioxaborolan-4-yl]-3(RS)-methylvalerate were dissolved in 1 ml of trifluoroacetic acid and 1 ml of dichloromethane. The solution was stirred at room temperature for 15 minutes and then evaporated under a vacuum. The residue was co-evaporated with toluene to give 46 mg of 5-[2-[1 (RS)-[[N-[(9-fluorenyl)methoxycarbonyl]-L-leucyl]amino]propyl]- 4(RS),5,5-trimethyl-1,3,2-dioxaborolan-4-yl]-3(RS)-methylvaleric acid as an oil; MS: m/e 621 [M+H]+.

ix) 5 g (5.25 mmol) of 4-methylbenzhydrylamine resin were swollen in dimethylformamide and excess solvent was drained from the resin. The resin was then resuspended in dimethylformamide containing 3.4 g (5.48 mmol) of 5-[2-[1(RS)-[[N-[(9-fluorenyl)methoxycarbonyl]-L-leucyl]amino]propyl]-4(RS),5,5-trimethyl-1,3,2-dioxaborolan-4-yl]-3(RS)-methylvaleric acid and 3 g (8.2 mmol) of 2-(1H-benzotriazol-1-yl)-1,1,3,3-tetramethyluronium hexafluorophosphate. Thereto there were added 3.0 ml (16.5 mmol) of diisopropylamine. The resulting mixture was agitated for 100 minutes and the resin was then drained and washed three times with dimethylformamide. The resin was then resuspended in dimethylformamide containing 5 ml (54.8 mmol) of acetic anhydride and 11.5 ml (110 mmol) of N-methylmorpholine. The mixture was agitated for 30 minutes and the resin was then drained. The resin was then resuspended in dimethylformamide containing 5 ml (54.8 mmol) of acetic anhydride and 11.5 ml (110 mmol) of N-methylmorpholine. The mixture was agitated for 30 minutes and the resin was then drained and washed three times with dimethylformamide, twice with ethyl acetate, twice with dichloromethane and twice with diethyl ether and then dried under a vacuum. After drying there was obtained 6 g of 5-[2-[1(RS)-[[N-[(9-fluorenyl)methoxycarbonyl]-L-leucyl]amino]propyl]-4-(RS),5,5-trimethyl-1,3,2-dioxoborolan-4-yl]-3(RS)-methyl-N-[a(RS)-(4-methylphenyl)benzyl]valeramide-polystyrene conjugate as a pale brown solid (0.25 mmol/g loading estimated by quantitation of dibenzofulvene at 301 nM).

EXAMPLE 24

In an analogous manner to that described in Example 5, from N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]- 3-cyclopentyl-N1-[1(RS)-(4,4,5,5-tetramethyl-1,3,2-dioxaborolan-2-yl)-3-butenyl]-L-alaninamide there was obtained 1(RS)-[[N-[N-[N-[N-[N-(3-carboxypropionyl)-L-α-aspartyl]-L-α-glutamyl]-2-methyl-L-phenylalanyl]-3-methyl-L-valyl]-3-cyclopentyl-L-alanyl]amino]-3-butenylboronic acid as a white solid; MS: m/e 855 [M+H−H$_2$O].

The starting material was prepared as follows:

i) A mixture of 1.2 g (4.67 mmol) of N-(tert-butoxycarbonyl)-3-cyclopentyl-L-alanine, 540 mg (5 mmol) of benzyl alcohol, 675 mg (5 mmol) of 1-hydroxybenzotriazole, 1.152 g (6 mmol) of 1-(3-dimethylaminopropyl)-3-ethylcarbodiimide hydrochloride and 0.031 g (0.25 mmol) of 4-dimethylaminopyridine was stirred in 20 ml of dichloromethane for 1 hour and then a further 610 mg (5 mmol) of 4-dimethylaminopyridine were added. After 4 hours the solution was extracted with 2M hydrochloric acid and saturated sodium bicarbonate solution, dried over anhydrous magnesium sulphate and evaporated. The oil obtained was chromatographed on silica gel using ethyl acetate/ petrol (1:6) for the elution to give 1.55 g of N-(tert-butoxycarbonyl)-3-cyclopentyl-L-alanine benzyl ester as a colourless oil; MS: m/e 348 [M+H].

ii) 1.54 g (4.44 mmol) of N-(tert-butoxycarbonyl)-3-cyclopentyl-L-alanine benzyl ester and 2.53 g (13.32 mmol) of 4-toluenesulphonic acid hydrate were dissolved in 20 ml of acetonitrile and the solution was left to stand at room temperature for 18 hours. The white precipitate formed was filtered off and added to a mixture of 867 mg (3.75 mmol) of N-(tert-butoxycarbonyl)-3-methyl-L-valine, 557 mg (3.64 mmol) of 1-hydroxybenzotriazole, 793 mg (4.14 mmol) of 1-(3-dimethylaminopropyl)-3-ethylcarbodiimide hydrochloride and 475 mg (4.13 mmol) of N-ethylmorpholine in 25 ml of dichloromethane and stirred at room temperature for 18 hours. The solution was extracted with 2M hydrochloric acid and saturated sodium bicarbonate solution and then dried over anhydrous magnesium sulphate. Evaporation and chromatography on silica gel using ethyl acetate/petrol (1:3) for the elution gave 1.06 g of N-[N-(tert-butoxycarbonyl)-3-methyl-L-valyl]-3-cyclopentyl-L-alanine benzyl ester as an off-white foam; MS: m/e 461 [M+H].

iii) 993 mg (2.16 mmol) of N-[N-(tert-butoxycarbonyl)-3-methyl-L-valyl]-3-cyclopentyl-L-alanine benzyl ester and 1.23 g (6.47 mmol) of 4-toluenesulphonic acid hydrate were dissolved in 20 ml of acetonitrile and the solution was stirred at room temperature for 2 hours. The solvent was removed by evaporation and the residue was triturated with diethyl ether and filtered off. The solid obtained was added to a mixture of 602 mg (2.16 mmol) of N-(tert-butoxycarbonyl)-2-methyl-L-phenylalanine, 338 mg (2.21 mmol) of 1-hydroxybenzotriazole, 576 mg (3 mmol) of 1-(3-dimethylaminopropyl)-3-ethylcarbodiimide hydrochloride and 345 mg (3 mmol) of N-ethylmorpholine in 20 ml of dichloromethane and stirred at room temperature for 18 hours. The solution was extracted with 2M hydrochloric acid and saturated sodium bicarbonate solution, then dried over anhydrous magnesium sulphate and evaporated. Chromatography of the residue on silica gel using ethyl acetate/ petrol (3:7) for the elution gave 990 mg of N-[N-[N-(tert-butoxycarbonyl)-2-methyl-L-phenylalanyl]-3-methyl-L-valyl]-3-cyclopentyl-L-alanine benzyl ester as a white solid; MS: m/e 622 [M+H].

iv) 980 mg (1.578 mmol) of N-[N-[N-(tert-butoxycarbonyl)-2-methyl-L-phenylalanyl]-3-methyl-L-valyl]-3-cyclopentyl-L-alanine benzyl ester and 900 mg (4.73 mmol) of 4-toluenesulphonic acid hydrate were dissolved in 16 ml of acetonitrile and the solution was stirred at room temperature for 2 hours. The solvent was removed by evaporation and the residue was triturated with diethyl ether and filtered off. The solid obtained was added to a mixture of 671 mg (1.578 mmol) of N-(9-fluorenylmethoxycarbonyl)-O-tert-butyl-L-α-glutamic acid, 247 mg (1.614 mmol) of 1-hydroxybenzotriazole, 419 mg (2.19 mmol) of 1-(3-dimethylaminopropyl)-3-ethylcarbodiimide hydrochloride and 252 mg (2.19 mmol) of N-ethylmorpholine in 16 ml of dichloromethane and stirred at room temperature for 18 hours. The solution was extracted with 2M hydrochloric acid and saturated sodium bicarbonate solution and then dried over anhydrous magnesium sulphate. Evaporation and chromatography on silica gel using methanol/dichloromethane (1:49) for the elution gave 530 mg of N-[N-[N-[O-tert-butyl-N-(9-fluorenylmethoxycarbonyl)-L-α-glutamyl]-2-methyl-L-phenylalanyl]-3-methyl-L-valyl]-3-cyclopentyl-L-alanine benzyl ester as a white solid; MS: m/e 929 [M+H].

v) A solution of 520 mg (0.56 mmol) of N-[N-[N-[O-tert-butyl-N-[(9-fluorenyl)methoxycarbonyl]-L-a-glutamyl]-2-methyl-L-phenylalanyl]-3-methyl-L-valyl]-3-cyclopentyl-L-alanine benzyl ester in 3 ml of piperidine and 12 ml of dichloromethane was stirred at room temperature for 30 minutes. The solvent was removed by evaporation and the residue was chromatographed on silica gel using firstly ethyl acetate/petrol (1:1) and then methanol/dichloromethane (1:9) for the elution. The resulting amine was added to a solution of 207 mg (0.504 mmol) of N-(9-fluorenylmethoxycarbonyl)-O-tert-butyl-L-α-aspartic acid, 78 mg (0.51 mmol) of 1-hydroxybenzotriazole and 134 mg (0.7 mmol) of 1-(3-dimethylaminopropyl)-3-ethylcarbodiimide hydrochloride in 10 ml of dichloromethane and stirred at room temperature for 18 hours. The solution was then extracted with 2M hydrochloric acid and saturated sodium bicarbonate solution and dried over anhydrous magnesium sulphate. Evaporation, trituration with diethyl ether and filtration gave 440 mg of N-[N-[N-[N-O-tert-butyl-N-[(9-fluorenyl)methoxycarbonyl]-L-a-aspartyl]-O-tert-butyl-L-α-glutamyl]-2-methyl-L-phenylalanyl]-3-methyl-L-valyl]-3-cyclopentyl-L-alanine benzyl ester as a white solid; MS: m/e 1101 [M+H].

vi) A solution of 430 mg (0.39 mmol) of N-[N-[N-[N-O-tert-butyl-N-[(9-fluorenyl)methoxycarbonyl]-L-α-aspartyl]-O-tert-butyl-L-α-glutamyl]-2-methyl-L-phenylalanyl]-3-methyl-L-valyl]-3-cyclopentyl-L-alanine benzyl ester in 4 ml of piperidine and 16 ml of dichloromethane was stirred at room temperature for 30 minutes and then evaporated. The residue was chromatographed on silica gel using firstly ethyl acetate/petrol (1:1) and then methanol/dichloromethane (1:9) for the elution. The amine obtained was added to a solution of 174 mg (1 mmol) of tert-butyl hydrogen succinate, 135 mg (1 mmol) of 1-hydroxybenzotriazole and 192 mg (1 mmol) of 1-(3-dimethylaminopropyl)-3-ethylcarbodiimide hydrochloride in 15 ml of dichloromethane and the mixture was stirred at room temperature for 18 hours, extracted with 2M hydrochloric acid and saturated sodium bicarbonate solution and then dried over anhydrous magnesium sulphate. Evaporation and chromatography on silica gel using methanol/ dichloromethane (1:24) for the elution followed by trituration with diethyl ether gave 240 mg of N-[N-[N-[N-[3-(tert-butoxycarbonyl)propionyl]-O-tert-butyl-L-a-aspartyl]-O-tert-butyl-L-α-glutamyl]-2-methyl-L-phenylalanyl]-3-methyl-L-valyl]-3-cyclopentyl-L-alanine benzyl ester as a white solid; MS: m/e 1035 [M+H].

vii) A solution of 230 mg (0.223 mmol) of N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-3-cyclopentyl-L-alanine benzyl ester in 10 ml of dimethylformamide was hydrogenated over 25 mg of 10% palladium/carbon for 3 hours. The catalyst was removed by filtration, the filtrate was evaporated and the residue was triturated with diethyl ether to give 206 mg of N-[N-[N-[N-[N-[3-(tert-butoxycarbonyl) propionyl]-O-tert-butyl-L-α-aspartyl]-O-tert-butyl-L-α-glutamyl]-2-methyl-L-phenylalanyll-3-methyl-L-valyl]-3-cyclopentyl-L-alanine as a white solid; MS: m/e 944 [M+H].

viii) 163 mg (0.173 mmol) of N-[N-[N-[N-[3-(tert-butoxy-carbonyl)propionyl]-O-tert-butyl-L-α-aspartyl]-O-tert-butyl-L-α-glutamyl]-2-methyl-L-phenylalanyl]-3- methyl-L-valyl]-3-cyclopentyl-L-alanine were dissolved in 2 ml of dimethylformamide and 4 ml of dichloromethane. 80 mg (0.69 mmol) of N-ethylmorpholine were added and the solution was cooled to −10° C. 26 mg (0.19 mmol) of isobutyl chloroformate were added and the solution was stirred for 30 minutes at −10° C. 107 mg (0.345 mmol) of α-(RS)-allyl-4,4,5,5-tetramethyl-1,3,2-dioxaborolane-2-methylamine trifluoroacetate in 1 ml of dichloromethane were added and the mixture was stirred at −10° C. for 30 minutes and at room temperature for 3 hours. The solution was extracted with 2M hydrochloric acid and saturated sodium bicarbonate solution and then dried over anhydrous magnesium sulphate. Evaporation and chromatography on silica gel using methanol/dichloromethane (1:24) for the elution gave 54 mg of N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyll-3-methyl-L-valyl]-3-cyclopentyl-N1 -[1 (RS)-(4,4,5,5-tetramethyl-1,3,2-dioxaborolan-2-yl)-3-butenyl]-L-alaninamide as a white solid; MS: m/e 1024 [M+H–$C_6H_{12}O$].

EXAMPLE 25

In an analogous manner to that described in Example 5, from N2-[N-[N-[N-[N-[3-(tert-butoxycarbonyl)propionyl]-0-tert-butyl-L-α-aspartyl]-O-tert-butyl-L-α-glutamyl]-2-methyl-L-phenylalanyl]-3-cyclohexyl-L-alanyl]-N1-[1(RS)-(4,4,5,5-tetramethyl-1,3,2-dioxaborolan-2-yl)-3-butenyl-L-leucinamide, MS: m/e 1037 [M+H–$C_6H_1O$], there was obtained 1(RS)-[[N-[N-[N-[N-[N-(3-carboxy-propionyl)-L-α-aspartyl]-L-α-glutamyl]-2-methyl-L-phenylalanyl]-3-cyclohexyl-L-alanyl]-L-leucyl]amino]-3-butenylboronic acid; MS: m/e 869 [M+H–$H_2O$].

The starting material was prepared in an analogous manner to that described in Example 5 via the following intermediates:

i) N-[N-(tert-Butoxycarbonyl)-3-cyclohexyl-L-alanyl]-L-leucine benzyl ester; MS: mie 475 [M+H];

ii) N-[N-[N-(tert-butoxycarbonyl)-2-methyl-L-phenylalanyl]-3-cyclohexyl-L-alanyl]-L-leucine benzyl ester; MS: m/e 636 [M+H];

iii) N-[N-[N-[O-tert-butyl-N-[(9-fluorenyl) methoxycarbonyl]-L-α-glutamyl]-2-methyl-L-phenylalanyl]-3-cyclohexyl-L-alanyl]-L-leucine benzyl ester; MS: m/e 944 [M+H];

iv) N-[N-[N-[O-tert-butyl-N-[(9-fluorenyl) methoxycarbonyl]-L-α-aspartyl]-O-tert-butyl-L-α-glutamyl]-2-methyl-L-phenylalanyl]-3-cyclohexyl-L-alanyl]-L-leucine benzyl ester; MS: m/e 1114 [M+H];

v) N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-cyclohexyl-L-alanyl]-L-leucine benzyl ester; MS: m/e 1049 [M+H]; and vi) N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-cyclohexyl-L-alanyl]-L-leucine; MS: m/e 958 [M+H].

EXAMPLE 26

In an analogous manner to that described in Example 5, from N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-L-2-phenylglycyl]-N1-[1 (RS)-(4, 4,5,5-tetramethyl-1 ,3,2-dioxaborolan-2-yl)-3-butenyl-L-leucinamide, MS: m/e 1017 [M+H-$C_6H_{12}O$], there was obtained 1 (RS)-[[N-[N-[N-[N-[N-(3-carboxy-propionyl)-L-α-aspartyl]-L-α-glutamyl]-2-methyl-L-phenylalanyl]-L-2-phenylglycyl]-L-leucyl]amino]-3-butenylboronic acid; MS: m/e 849 [M+H–$H_2O$].

The starting material was prepared in an analogous manner to that described in Example 5 via the following intermediates:

i) N-[N-(tert-Butoxycarbonyl)-L-2-phenylglycyl]-L-leucine benzyl ester; MS: m/e 455 [M+H];

ii) N-[N-[N-(tert-butoxycarbonyl)-2-methyl-L-phenylalanyl]-L-2-phenylglycyl]-L-leucine benzyl ester; MS: m/e 616 [M+H];

iii) N-[N-[N-[O-tert-butyl-N-[(9-fluorenyl) methoxycarbonyl]-L-α-glutamyl]-2-methyl-L-phenylalanyl]-L-2-phenylglycyl]-L-leucine benzyl ester; MS: m/e 923 [M+H];

iv) N-[N-[N-[N-[O-tert-butyl-N-[(9-fluorenyl) methoxycarbonyl]-L-α-aspartyl]-O-tert-butyl-L-α-glutamyl]-2-methyl-L-phenylalanyl]-L-2-phenylglycyl]-L-leucine benzyl ester; MS: m/e 1094 [M+H];

v) N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-L-2-phenylglycyl]-L-leucine benzyl ester; MS: m/e 1028 [M+H]; and vi) N- N- N-[N-[N-[3-(tert-butoxycarbonyl)propionyl]-O-tert-butyl-L-α-aspartyl]-O-tert-butyl-L-α-glutamyl]-2-methyl-L-phenylalanyl]-L-2-phenylglycyl]-L-leucine; MS: m/e 938 [M+H].

EXAMPLE 27

In an analogous manner to that described in Example 5, from N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-L-2-cyclohexylglycyl]-N1-[1(RS)-(4,4,5,5-tetramethyl-1,3,2-dioxaborolan-2-yl)-3-butenyl-L-leucinamide, MS: m/e 1023 [M+H–$C_6H_{12}O$], there was obtained 1(RS)-[[N-[N-[N-[N-[N-(3-carboxypropionyl)-L-α-aspartyl]-L-α-glutamyl]-2-methyl-L-phenylalanyl]-L-2-cyclohexylglycyl]-L-leucyl]amino]-3-butenylboronic acid; MS: m/e 855 [M+H–$H_2O$].

The starting material was prepared in an analogous manner to that described in Example 5 via the following intermediates:

i) N-[N-(tert-Butoxycarbonyl)-L-2-cyclohexylglycyl]-L-leucine benzyl ester; MS: m/e 461 [M+H];

ii) N-[N-[N-(tert-butoxycarbonyl)-2-methyl-L-phenylalanyl]-L-2-cyclohexylglycyl]-L-leucine benzyl ester; MS: m/e 622 [M+H];

iii) N-[N-[N-[O-tert-butyl-N-[(9-fluorenyl) methoxycarbonyl]-L-α-glutamyl]-2-methyl-L-phenylalanyl]-L-2-cyclohexylglycyl]-L-leucine benzyl ester; MS: m/e 929 [M+H];

iv) N-[N-[N-[O-tert-butyl-N-[(9-fluorenyl) methoxycarbonyl]-L-α-aspartyl]-O-tert-butyl-L-α-glutamyl]-2-methyl-L-phenylalanyl]-L-2-cyclohexylglycyl]-L-leucine benzyl ester; MS: m/e 1100 [M+H];

v) N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-L-2-cyclohexylglycyl]-L-leucine benzyl ester; MS: m/e 1034 [M+H]; and vi) N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-L-2-cyclohexylglycyl]-L-leucine; MS: m/e 944 [M+H].

EXAMPLE 28

In an analogous manner to that described in Example 5, from N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(RS)-(4,4,5,5-tetramethyl-1,3,2-dioxaborolan-2-yl)-3-butenyl-L-prolinamide, MS: m/e 981 [M+H-C$_6$H$_{12}$O], there was obtained 1(RS)-[[N-[N-[N-[N-[N-(3-carboxy-propionyl)-L-α-aspartyl]-L-α-glutamyl]-2-methyl-L-phenylalanyl]-3-methyl-L-valyl]-L-prolyl]amino]-3-butenylboronic acid as a white solid; MS: m/e 813 [M+H-H$_2$O].

The starting material was prepared in an analogous manner to that described in Example 5 via the following intermediates:

i) N-[N-(tert-Butoxycarbonyl)-3-methyl-L-valyl]-L-proline benzyl ester;
ii) N-[N-[N-(tert-butoxycarbonyl)-2-methyl-L-phenylalanyl]-3-methyl-L-valyl]-L-proline benzyl ester;
iii) N-[N-[N-[O-tert-butyl-N-[(9-fluorenyl)methoxycarbonyl]-L-α-glutamyl]-2-methyl-L-phenylalanyl]-3-methyl-L-valyl]-L-proline benzyl ester;
iv) N-[N-[N-[O-tert-butyl-N-[(9-fluorenyl)methoxycarbonyl]-L-α-aspartyl]-O-tert-butyl-L-α-glutamyl]-2-methyl-L-phenylalanyl]-3-methyl-L-valyl]-L-proline benzyl ester;
v) N-[N-[N-[N-[O-tert-butyl-N-[3-(tert-butoxycarbonyl)-propionyl]-L-α-aspartyl]-O-tert-butyl-L-α-glutamyl]-2-methyl-L-phenylalanyl]-3-methyl-L-valyl-L-proline benzyl ester; MS: m/e 992 [M+H]; and
vi) N-[N-[N-[N-[O-tert-butyl-N-[3-(tert-butoxycarbonyl)-propionyl]-L-α-aspartyl]-O-tert-butyl-L-α-glutamyl]-2-methyl-L-phenylalanyl]-3-methyl-L-valyl-L-proline.

EXAMPLE 29

In an analogous manner to that described in Example 5, from N2-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-L-phenylalanyl]-N1-[1 (RS)-(4,4,5,5-tetramethyl-1,3,2-dioxaborolan-2-yl)-3-butenyl-L-leucinamide, MS: m/e 1031 [M+H-C$_6$H$_2$O], there was obtained 1(RS)-[[N-[N-[N-[N-(3-carboxy-propionyl)-L-α-aspartyl]-L-α-glutamyl]-2-methyl-L-phenylalanyl]-L-phenylalanyl]-L-leucyl]amino]-3-butenylboronic acid as a white solid; MS: m/e 863 [M+H-H$_2$O].

The starting material was prepared in an analogous manner to that described in Example 5 via the following intermediates:

i) N-[N-[N-[O-tert-Butyl-N-[(9-fluorenyl)methoxycarbonyl]-L-α-glutamyl]-2-methyl-L-phenylalanyl]-L-phenylalanyl]-L-leucine benzyl ester;
ii) N-[N-[N-[O-tert-butyl-N-[(9-fluorenyl)methoxycarbonyl]-L-α-aspartyl]-O-tert-butyl-L-α-glutamyl]-2-methyl-L-phenylalanyl]-L-phenylalanyl]-L-leucine benzyl ester;
iii) N-[N-[N-[N-N-[3-(tert-butoxycarbonyl)propionyl]-O-tert-butyl-L-α-aspartyl]-O-tert-butyl-L-α-glutamyl]-2-methyl-L-phenylalanyl]-L-phenylalanyl]-L-leucine benzyl ester; MS m/e 1042 [M+H]; and
iv) N-[N-[N-N-[3-(tert-butoxycarbonyl)propionyl]-3-O-tert-butyl-L-α-aspartyl]-O-tert-butyl-L-α-glutamyl]-2-methyl-L-phenylalanyl]-L-phenylalanyl]-L-leucine.

EXAMPLE 30

0.04 g (0.03 mmol) of (E)-N2-[N-[N-[N-[N-(tert-butoxycarbonyl)propionyl]-O-tert-butyl-L-α-aspartyl]-O-tert-butyl-α-glutamyl]-2-methyl-L-phenylalanyl]-3-methyl-L-valyl]-N1-[1(S)-(dimethoxymethyl)-3-pentyl]-L-leucinamide was dissolved in 4 ml of a 1:1 solution of dichloromethane and trifluoroacetic acid containing 3 drops of water. The resulting solution was stirred at room temperature for 1 hour. After removal of the solvent by evaporation and trituration of the residue with diethyl ether there was obtained 0.014 g of (E)-2(S)-[[N-[N-[N-[N-[N-(3-carboxy-propionyl)-L-α-aspartyl]-L-α-glutamyl]-2-methyl-L-phenylalanyl]-3-methyl-L-valyl]-L-leucyl]amino]-4-hexenal; MS: m/e 845.7 [M+H]+.

The starting material was prepared as follows:

i) 25 g (347 mmol) of trans-2-buten-1-ol were dissolved in 750 ml of anhydrous diethyl ether. 7.25 ml (89.63 mmol) of anhydrous pyridine were added and the resulting solution was cooled to 0° C. 88.25 ml of phosphorus tribromide were added dropwise and the mixture was stirred for 2 hours at 0° C. The reaction was quenched by pouring the solution on to ice. The organic phase was washed with saturated sodium chloride solution and dried over anhydrous magnesium sulphate. After removal of the solvent by evaporation there was obtained (E)-1-bromo-2-butane which was used in the next step without purification.

ii) 3.86 g (168 mmol) of sodium metal were dissolved in 106 ml of anhydrous ethanol. 36.35 g (168 mmol) of diethyl acetamidomalonate dissolved in 225 ml of anhydrous ethanol were added and the mixture was heated under reflux for 10 minutes. 22.66 g (168 mmol) of (E)-1-bromo-2-butene were added dropwise at room temperature and the mixture was stirred overnight and then evaporated to dryness under a vacuum. The residue was partitioned between ethyl acetate and 0.1M hydrochloric acid. The organic phase was washed with saturated sodium hydrogen carbonate solution and then with saturated sodium chloride solution and dried over anhydrous magnesium sulphate. The solvent was evaporated to give 40 g of diethyl (E)-2-acetamido-2-(2-butenyl) malonate as a colourless oil; $^1$H NMR (250 MHz, CDCl$_3$) d: 1.25 (t, 6H), 1.6 (d, 3H), 2.0 (s, 3H), 2.9 (d, 2H), 4.2 (q, 4H), 5.15 (m, 1H) 5.5 (m, 1H), 6.7 s, 1H).

iii) 39.63g (146 mmol) of diethyl (E)-2-acetamido-2-(2-butenyl)malonate were dissolved in 200 ml of ethanol and a solution of 19.24 g (481 mmol) of sodium hydroxide in 100 ml of water was added. The mixture was stirred for 2 hours at 60° C., evaporated to dryness under a vacuum and the residue was partitioned between diethyl ether and water. The aqueous phase was acidified with 2M hydrochloric acid and extracted with ethyl acetate. The organic phase was dried over magnesium sulphate and the solvent was removed by evaporation under a vacuum to give 26.1 g of (E)-2-acetamido-2-(2-butenyl)malonic acid as a white solid which was used in the next step without further purification. $^1$H NMR (250 MHz, MeOD) δ: 1.65 (d, 3H), 2.0 (s, 3H), 2.9 (d, 2H), 5.25 (m, 1H), 5.5 (m, 1H).

iv) 26.1 g (121 mmol) of (E)-2-acetamido-2-(butenyl) malonic acid were dissolved in 200 ml of toluene. 34 ml (242 mmol) of triethylamine were added and the mixture was heated under reflux for 1 hour. The solution was extracted with 1M hydrochloric acid and the aqueous layer was extracted with ethyl acetate. The combined organic phases were dried over magnesium sulphate and the solvent was removed under a vacuum to give 18.73 g of (E)-N-acetyl-DL-2-(2-butenyl)glycine as a white solid which was used in the next step without purification. $^1$H NMR (250 Hz, MeOD) δ: 1.65 (d, 3H), 2.0 (s, 3H), 2.4 (m, 2H), 4.3 (m, 1H), 5.4 (m, 1H), 5.5 (m, 1H).

v) 9 g (52.63 mmol) of (E)-N-acetyl-DL-2-(2-butenyl) glycine were dissolved in 100 ml of water and the pH adjusted to 7.5 using ammonia solution. 0.09 g of acylase I extracted from porcine kidney, and 0.042 g (0.3 mmol) of cobalt (II) chloride were added and the mixture was stirred at 37° C. overnight. A further 0.09 g of acylase 1 extracted from porcine kidney was added and the pH adjusted to 7.5 using ammonia solution. The mixture was stirred at 37° C. overnight and the solution was then heated at 80° C. for 30 minutes and was then acidified to pH 1 using 2 M hydrochloric acid. The solvent was removed by evaporation under vacuum and the crude product purified by trituration using ethyl acetate to yield 4.2 g of (E)-L-2-(2-butenyl)glycine hydrochloride. $^1$H NMR (250 MHz, D$_2$O) δ: 1.7 (d, 3H), 2.6 (m, 2H), 4.0 (m, 1H), 5.35 (m, 1H), 5.7 (m, 1H).

vi) 2.1 g (12.69 mmol) of (E)-L-(2-butenyl)glycine hydrochloride were suspended in 20 ml of water and 20 ml of dioxan. 8.26 g (98.32 mmol) of sodium hydrogen carbonate and 8.15 g (37.33 mmol) of di-tert-butyl dicarbonate were added and the resulting solution was stirred for overnight. The solution was evaporated to dryness under a vacuum and the residue was partitioned between diethyl ether and saturated aqueous sodium hydrogen carbonate solution. The aqueous phase was acidified with 2M hydrochloric acid while partitioning in ethyl acetate. The organic phase was dried over magnesium sulphate and the solvent was removed by evaporation to give 1.34 g of (E)-N-(tert-butoxycarbonyl)-L-2-(2-butenyl)glycine; $^1$H NMR (250 MHz, CDCl$_3$) d: 1.4 (s, 9H), 1.65 (d, 3H), 2.5 (m, 2H), 4.3 (m, 1H), 5.0 (m, 1H), 5.35 (m, 1H), 5.6 (m, 1H).

vii) 1.34 g (5.85 mmol) of (E)-N-(tert-butoxycarbonyl)-L-2-(2-butenyl)glycine were dissolved in 50 ml of anhydrous tetrahydrofuran and the solution was treated in sequence with 0.80 g (8.20 mmol) of N,O-dimethylhydroxylamine hydrochloride, 1.10 g (7.19 mmol) of 1-hydroxybenzotriazole monohydrate, 1.57 g (8.22 mmol) of 1-(3-dimethylaminopropyl)-3-ethylcarbodiimide hydrochloride and 4 ml (22.96 mmol) of ethyldiisopropylamine. The solution obtained was stirred at room temperature overnight, then washed with saturated sodium hydrogen carbonate solution and with saturated sodium chloride solution and dried over magnesium sulphate. Removal of the solvent by evaporation yielded 1.56 g of N,O-dimethyl (E)-2(S)-(tert-butoxyformamido)-4-hexenohydroxamate as a colourless oil which was used in the next step without purification. $^1$H NMR (250 MHz, CDCl$_3$) δ: 1.4 (s, 9H), 1.65 (d, 3H), 2.3 (m, 2H), 3.15 (s, 3H), 3.75 (s, 3H), 4.7 (m, 1H), 5.1 (d, 1H), 5.35 (m, 1H), 5.5 (m, 1H).

viiii) 1.56 g (5.74 mmol) of N,O-dimethyl (E)-2(S)-(tert-butoxy-formamido)-4-hexenohydroxamate were dissolved in 10 ml of anhydrous tetrahydrofuran and cooled to 0° C. 4.0 ml of a 1M solution of lithium aluminium hydride in tetrahydrofuran were added and the resulting solution was stirred for 30 minutes. The reaction was quenched by the dropwise addition of saturated potassium hydrogen sulphate solution followed by diethyl ether. The resulting two-phase system was stirred vigorously for 3 minutes. The organic phase was washed with saturated sodium hydrogen carbonate solution followed by saturated sodium chloride solution and dried over anhydrous magnesium sulphate. After removal of the solvent by evaporation the resulting aldehyde was used without purification.

1 g (4.69 mmol) of the aldehyde was dissolved in a saturated solution of hydrogen chloride in methanol and stirred at room temperature for 2 hours. After removal of the solvent by evaporation the dimethyl acetal obtained was used without purification.

0.15 mg (0.16 mmol) of N-[N-[N-[N-[N-3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine, 0.033 g (0.22 mmol) of 1-hydroxybenzotriazole monohydrate, 0.047 g (0.25 mmol) of 1-(3-dimethylaminopropyl)-3-ethylcarbodiimide hydrochloride and 0.77 g (6.69 mmol) of 4-ethylmorpholine were dissolved in 15 ml of dichloromethane. 0.05 g (0.22 mmol) of the dimethyl acetal dissolved in 5 ml of dichloromethane was added and the resulting solution was stirred at room temperature for 3 days. The mixture was washed with 5% citric acid solution followed by saturated sodium hydrogen carbonate solution and saturated sodium chloride solution and then dried over anhydrous magnesium sulphate. After evaporation of the solvent the crude product was chromatographed on silica gel using 2% methanol in dichloromethane for the elution to give 0.079 g of (E)-N2-[N-[N-[N-[N-(3-tert-butoxycarbonyl)propionyl]-tert-butyl-L-α-aspartyl]-O-tert-butyl-α-glutamyl]-2-methyl-L-phenylalanyl]-3-methyl-L-valyl]-N1-[1(S)-(dimethoxymethyl)-3-pentyl]-L-leucinamide as a white solid foam; m/e 1027.9 [M+H–MeOH]+.

EXAMPLE 31

0.05 g (0.04 mmol) of (Z)-N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N 1-[1(S)-(dimethoxymethyl)-3-pentenyl]-L-leucinamide was dissolved in 4 ml of a 1:1 solution of dichloromethane and trifluoroacetic acid and containing 3 drops of water. The solution was stirred at room temperature for 1 hour. After removal of the solvent by evaporation the crude product was triturated using diethyl ether to afford 0.03 g of (Z)-2(S)-[[N-[N-[N-[N-[N-(3-carboxypropionyl)-L-alpha-aspartyl]-L-alpha-glutamyl]-2-methyl-L-phenylalanyl]-3-methyl-L-valyl]-L-leucyl]amino]-4-hexenal as a white solid; MS: m/e 845.7 [M+H]$^+$.

The starting material was prepared as follows:

i) 25 g (347 mmol) of cis-2-buten-1-ol were dissolved in 750 ml of anhydrous diethyl ether. 7.25 ml of anhydrous pyridine were added and the resulting solution cooled to OOC. 88.25 ml of phosphorus tribromide was added dropwise and the mixture was stirred for 2 hours at 0° C. The reaction was quenched by pouring the solution onto ice. The organic phase was washed with saturated sodium chloride solution and dried over anhydrous magnesium sulphate. After removal of the solvent by evaporation there was obtained 25.65 g of (Z)-1-bromo-2-butene; $^1$H NMR (250 MHz, CDCl$_3$) δ: 1.65 (d, 3H), 3.9 (d, 2H), 5.6 (m, 2H).

ii) 4.37 g (190 mmol) of sodium metal were dissolved in 110 ml of anhydrous ethanol. 41.14 g (189.6 mmol) of diethyl acetamidomalonate dissolved in 270 ml of anhydrous ethanol were added and the mixture was heated under reflux for 10 minutes. 25.65 g (168 mmol) of (Z)-1-bromo-2-butene were added dropwise at room temperature and the mixture was stirred overnight, then evaporated to dryness under vacuum and the residue was partitioned between ethyl acetate and 0.1 M hydrochloric acid. The organic phase was washed with saturated sodium hydrogen carbonate solution followed by saturated sodium chloride solution and dried over anhydrous magnesium sulphate. After removal of the solvent by evaporation the crude product was chromatographed on silica gel using 66% ethyl acetate in petroleum ether as eluent to obtain 44.69 g of diethyl (Z)-2-acetamido-2-(2-butenyl)malonate as a colourless oil;$^1$H NMR (250

MHz, CDCl₃) δ: 1.2 (t, 6H), 1.6 (d, 3H), 2.0 (s, 3H), 3.1 (d, 2H), 4.2 (q, 4H), 5.1(m, 1H), 5.6 (m, 1H), 6.7 (s, 1H).

iii) 44.69 g (165 mmol) of diethyl (Z)-2-acetamido-2-(2-butenyl)malonate were dissolved in 230 ml of ethanol and a solution of 21.69 g (542 mmol) of sodium hydroxide in water was added. The mixture was stirred for 2 hours at 60° C., evaporated to dryness under a vacuum and the residue was partitioned between diethyl ether and water. The aqueous phase was acidified using 2M hydrochloric acid and extracted with ethyl acetate. The organic phase was dried over magnesium sulphate and the solvent removed by evaporation in a vacuum to give 33.5 g of (Z)-2-acetamido-2-(2-butenyl)malononic acid as a white solid; 1 H NMR (250 MHz, MeOD) δ: 1.6 (d, 3H), 2.0 (s, 3H), 2.85 (d, 2H), 5.25 (m, 1H), 5.6 (m, 1H).

iv) 16.82 g (78.23 mmol) of (Z)-2-acetamido-2-(2-butenyl)-malononic acid were dissolved in 100 ml of toluene. 34 ml (242 mmol) of triethylamine were added and the mixture was heated under reflux for 1 h, then washed with 1M hydrochloric acid and the aqueous phase was extracted with ethyl acetate. The combined organic phases were dried over magnesium sulphate and the solvent was removed under a vacuum to give 9.4 g of (Z)-N-acetyl-DL-2-(2-butenyl) glycine as a white solid; 1 H NMR (250 MHz, MeOD) δ: 1.6 (d, 3H), 2.0 (s, 3H), 2.5 (m, 2H), 4.4 (m, 1H), 5.4 (m, 1H), 5.6 (m, 1H).

v) 9.4 g (54.97 mmol) of (Z)-N-acetyl-DL-2-(2-butenyl) glycine were dissolved in 100 ml of water and the pH was adjusted to 7.8 with ammonia solution. 0.09 g of acylase I extracted from porcine kidney, and 0.042 g (0.3 mmol) of cobalt (II) chloride were added and the resulting reaction mixture was stirred at 37° C. overnight. The pH was adjusted to 7.8 using ammonia solution. The mixture was stirred at 370C overnight and was then heated at 80° C. for 30 minutes and was then acidified to pH 1 using 2M hydrochloric acid. The solution was acidified to pH 1 using 2M hydrochloric acid and then heated at 80° C. for 30 minutes. The solvent was removed by evaporation under a vacuum and the crude product obtained purified by trituration using ethyl acetate to yield 5.86 g of (Z)-L-2-(2-butenyl)glycine hydrochloride; ¹H NMR (250 MHz, D₂O) δ: 1.6 (d, 3H), 2.7 (t, 2H), 4.1 (t, 1H), 5.3 (m, 1H), 5.8 (m, 1H).

vi) 2.9 g (17.52 mmol) of (Z)-L-2-(2-butenyl)glycine hydrochloride were suspended in 25 ml of water and 25 ml of dioxan. 11.4 g (136 mmol) of sodium hydrogencarbonate and 8.49 g (38.94 mmol) of di-tert-butyl dicarbonate were added and the resulting solution was stirred for 48 hours. The solution was evaporated to dryness under a vacuum and the residue was partitioned between diethyl ether and saturated aqueous sodium hydrogen carbonate solution. The aqueous phase was acidified using 2M hydrochloric acid whilst being partitioned with ethyl acetate. The organic phase was dried over magnesium sulphate and the solvent removed by evaporation to give 2.26 g of (Z)-N-(tert-butoxycarbonyl)-L-2-(2-butenyl)glycine; ¹H NMR (250 MHz, CDCl₃) δ: 1.4 (s, 9H), 1.6 (d, 3H), 2.6 (m, 2H), 4.4 (m, 1H), 5.05 (m, 1H), 5.3 (m, 1H), 5.6 (m, 1H).

vii) 2.26 g (9.87 mmol) of (Z)-N-(tert-butoxycarbonyl)-L-2-(2-butenyl)glycine were dissolved in 50 ml of anhydrous tetrahydrofuran. 1.15 g (11.79 mmol) of N,O-dimethylhydroxylamine hydrochloride, 1.6 g (10.46 mmol) of 1- hydroxybenzotriazole monohydrate, 2.27 g (11.88 mmol) of 1-(3-dimethylaminopropyl)-3-ethylcarbodiimide hydrochloride and 5.8 ml of ethyldiisopropylamine were added and the resulting solution was stirred at room temperature overnight. The solution was washed with saturated sodium hydrogen carbonate solution followed by saturated sodium chloride solution and then dried over anhydrous magnesium sulphate. Removal of the solvent by evaporation yielded 2.46 g of N,O-dimethyl (Z)-2(S)-(tert-butoxyformamido)-4-hexenohydroxamate as a colourless oil; ¹H NMR (250 MHz, CDCl₃) δ: 1.4 (s, 9H), 1.6 (d, 3H), 2.35 (m, 1H), 2.5 (m, 1H), 3.2 (s, 3H), 3.75 (s, 3H), 4.7 (m, 1H), 5.2 (d, 1H), 5.35 (m, 1H), 5.6 (m, 1H).

viii) 1.01 g (3.71 mmol) of N,O-dimethyl (Z)-2(S)-(tert-butoxyformamido)-4-hexenohydroxamate were dissolved in 10 ml of anhydrous tetrahydrofuran and cooled to 0° C. 2.6 ml of a 1M solution of lithium aluminium hydride in tetrahydrofuran were added and the resulting solution was stirred for 30 minutes. The reaction was quenched by the dropwise addition 15 ml of saturated potassium hydrogen sulphate solution followed by 30 ml of diethyl ether. The resulting two-phase system was stirred vigorously for one hour. The organic phase was washed with saturated sodium hydrogen carbonate solution followed by saturated sodium chloride solution and dried over magnesium sulphate. After removal of the solvent by evaporation the aldehyde was used without further purification. 0.79 g (3.71 mmol) of the aldehyde was dissolved in a saturated solution of hydrogen chloride in 10 ml of methanol and stirred at room temperature for 2 hours. After removal of the solvent by evaporation the dimethylacetal obtained was used without purification 0.15 g (0.16 mmol) of N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-L-leucine, 0.033 g (0.22 mmol) of 1-hydroxybenzotriazole mono hydrate, 0.047 g (0.25 mmol) of 1-(3-dimethylaminopropyl)-3-ethylcarbodiimide hydrochloride and 0.77 g (6.69 mmol) of 4-ethylmorpholine were dissolved in 15 ml of dichloromethane. 0.05 g (0.22 mmol) of the foregoing dimethyl acetal dissolved in 5 ml of dichloromethane was added and the resulting solution was stirred at room temperature for 3 days. The solution was washed with 5% citric acid solution followed by saturated sodium hydrogen carbonate solution and saturated sodium chloride solution and then dried over magnesium sulphate. After removal of the solvent by evaporation the crude product was chromatographed on silica gel using 2% methanol in dichloromethane for the elution to give 0.092 g of (Z)-N2-[N-[N-[N-[N-[3-(tert-butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1 (S)-(dimethoxymethyl)-3-pentenyl]-L-leucinamide, as a white solid foam; MS: m/e 1027.9 [M+H–MeOH]⁺.

EXAMPLE 32

In an analogous manner to that described in Example 10, but using N-(tert-butoxycarbonyl)-3-(2-furyl)-L-alanine in place of N-(tert-butoxycarbonyl)-L-allylglycine there was obtained 2(RS)-[[N-[N-[N-[N-[N-(3-carboxypropionyl)-L-a-aspartyl]-L-a-glutamyl]-2-methyl-L-phenylalanyl]-3-methyl-L-valyl]-L-leucyl]amino]-3-(2-furyl) propionaldehyde; MS: m/e 871.4 [M+H]⁺.

The starting material was prepared in an analogous manner to that described in Example 10 via the following intermediates:

i) N,O-Dimethyl 2(S)-(tert-butoxyformamido)-2-(2-furyl)-propionohydroxamate; ¹H NMR (250 MHz, CDCl₃) δ: 1.4 (s, 9H), 3.0 (m, 2H), 3.2 (s, 3H), 3.7 (s, 3H), 4.9 (m, 1H), 5.3 (br. d, 1H), 6.1 (br. s, 1H), 6.3 (br. s, 1H), 7.3 (br. s, 1H).

ii) N2-[N-[N-[N-[3-(tert-Butoxycarbonyl)propionyl]-O-tert-butyl-L-α-aspartyl]-O-tert-butyl-L-α-glutamyl]-2- methyl-L-phenylalanyl]-3-methyl-L-valyl]-N1-[2-(2-furyl)-1(S)-(dimethoxymethyl)ethyl]-L-leucinamide; used directly in the next step.

EXAMPLE 33

In an analogous manner to that described in Example 10, but using N-(tert-butoxycarbonyl)-L-norvaline in place of N-(tert-butoxycarbonyl)-L-allylglycine there was obtained 2(S)-[[N-[N-[N-[N-[N-(3-carboxypropionyl)-L-a-aspartyl]-L-a-glutamyl1-2-methyl-L-phenylalanyl]-3-methyl-L-valyl]-L-leucyl]amino]valeraldehyde; MS: m/e 833.4 [M+H]+.

The starting material was prepared in an analogous manner to that described in Example 10 via the following intermediates:

N,O-Dimethyl 2(S)-(tert-butoxyformamido)valerohydroxamate; $^1$H NMR (250 MHz, CDCl$_3$) δ: 0.8 (m, 3H), 1.2–1.7 (m, 4H), 1.4 (s, 9H), 3.1 (s, 3H), 3.7 (s, 3H), 4.6 (m, 1H), 5.1 (br. d, 1H).

N2-[N-[N-[N-[N-[3-(tert-Butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)butyl]-L-leucinamide; MS: m/e 1069.6 [M+Na]+.

EXAMPLE 34

In an analogous manner to that described in Example 10, but using N-(tert-butoxycarbonyl)-L-butylglycine in place of N-(tert-butoxycarbonyl)-L-allylglycine there was obtained 2(S)-[[N-[N-[N-[N-[N-(3-carboxypropionyl)-L-a-aspartyl]-L-a-glutamyl]-2-methyl-L-phenylalanyl]-3-methyl-L-valyl]-L-leucyl]amino]hexanal; MS: m/e 847.4 [M+H]+.

The starting material was prepared in an analogous manner to that described in example 10 via the following intermediates:

i) N,O-Dimethyl 2(S)-(tert-butoxyformamido)hexanohydroxamate; $^1$H NMR (250 MHz, CDCl$_3$) δ: 0.9 (m, 3H), 1.2–1.8 (m, 6H), 1.4 (s, 9H), 3.2 (s, 3H), 3.7 (s, 3H), 4.6 (m, 1H), 5.1 (br. d, 1H).

ii) N2-[N-[N-[N-[3-(tert-Butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-pentyl]-L-leucinamide; MS: m/e 1083 [M+Na]+.

EXAMPLE 35

In an analogous manner to that described in Example 10, but using DL-hexylglycine in place of L-allylglycine hydrochloride there was obtained 2(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]octanal; MS: m/e 875.5 [M+H]+.

The starting material was prepared in an analogous manner to that described in Example 10 via the following intermediates:

i) 2(RS)-(tert-Butoxyformamido)octanoic acid; $^1$H NMR (250 MHz, CDCl$_3$) δ: 0.9 (m, 3H), 1.2–1.9 (m, 10H), 1.4 (s, 9H), 4.3 (m, 1H), 5.0 (br. d, 1H)

ii) N,O-Dimethyl 2(RS)-(tert-butoxyformamido)octanohydroxamate; $^1$H NMR (250 MHz, CDCl$_3$) δ: 0.9 (m, 3H), 1.2-1.8 (m, 1OH), 1.4 (s, 9H), 3.2 (s, 3H), 3.7 (s, 3H) 4.6 (m, 1H), 5.1 (br. d, 1H)

iii) N2-[N-[N-[N-[N-[3-(tert-Butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(RS)-(dimethoxymethyl)heptyl]-L-leucinamide; MS: m/e 1111.6 [M +Na]+.

EXAMPLE 36

In an analogous manner to that described in Example 10, but using 2(S)-amino-5-methylhexanoic acid in place of L-allylglycine hydrochloride there was obtained 2(S)-[[N-[N-[N-[N-N-(3-carboxypropionyl)-L-α-aspartyl]-L-α-glutamyl]-2-methyl-L-phenylalanyl]-3-methyl-L-valyl]-L-leucyl]amino]-5-methylhexanal; MS: m/e 861.3 [M+H]+.

The starting material was prepared in an analogous manner to that described in Example 10 via the following intermediates:

i) 2(S)-(tert-Butoxyformamido)-5-methylhexanoic acid; 1H NMR (250 MHz, CDCl$_3$) δ: 0.9 (d, 6H), 1.2 (m, 2H), 1.4 (s, 9H), 1.5 (m, 1H), 1.7 (m, 1H), 1.9 (m, 1H), 4.3 (m, 1H), 4.9 (br. d, 1H).

ii) N,O-Dimethyl 2(S)-(tert-butoxyformamido)-5-methylhexanohydroxamate; 1H NMR (250 MHz, CDCl$_3$) δ: 0.85 (d, 3H), 0.9 (d, 3H), 1.2 (m, 2H), 1.4 (s, 9H), 1.4–1.8 (m, 3H), 3.2 (s, 3H), 3.8 (s, 3H), 4.6 (m, 1H), 5.1 (br. d, 1H).

iii) N2-[N-[N-[N-[N-[3-(tert-Butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1 (S)-(dimethoxymethyl)-4-methylpentyl]-L-leucinamide; MS: m/e 1043.8 [M+H-MeOH]+.

EXAMPLE 37

In an analogous manner to that described in Example 10, but using 2(S)-amino-5-hexenoic acid in place of L-allylglycine hydrochloride there was obtained 2(S)-[[N-[N-[N-[N-(3-carboxy-propionyl)-L-α-aspartyl]-L-α-glutamyl]-2-methyl-L-phenylalanyl]-3-methyl-L-valyl]-L-leucyl]amino]-5-hexenal; MS: m/e 845.3 [M+H]+.

The starting material was prepared in an analogous manner to that described in Example 10 via the following intermediates:

i) 2(S)-tert-Butoxyformamido)-5-hexenoic acid; 1 H NMR (250 MHz, CDCl$_3$) δ: 1.4 (s, 9H), 1.8 (m, 1H), 1.95 (m, 1H), 2.2 (m, 2H), 4.3 (m, 1H), 5.0 (m, 3H), 5.8 (m, 1H).

ii) N,O-Dimethyl 2(S)-(tert-butoxyformamido)-5-hexenohydroxamate; 1H NMR (250 MHz, CDCl$_3$) δ: 1.4(s, 9H), 1.6–1.8 (m, 2H), 2.1 (m, 2H), 3.2 (s, 3H), 3.7 (s, 3H) 4.7 (m, 1H), 5.0 (m, 3H), 5.8 (m, 1H).

iii) N2-[N-[N-[N-[N-[3-(tert-Butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-4-pentenyl]-L-leucinamide; MS: m/e 1081.6 [M+Na]+.

EXAMPLE 38

In an analogous manner to that described in Example 10, but using 2(S)-amino-5-hexynoic acid in place of L-allylglycine hydrochloride there was obtained 2(S)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-5-hexynal; MS: m/e 843.3 [M+H]+.

The starting material was prepared in an analogous manner to that described in Example 10 via the following intermediates:

i) 2(S)-(tert-Butoxyformamido)-5-hexynoic acid; 1H NMR (250 MHz, MeOD) δ: 1.4 (s, 9H), 1.8 (m, 1H), 2.0 (m, 1H), 2.3 (m, 3H), 4.2 (m, 1H).

ii) N,O-Dimethyl 2(S)-(tert-butoxyformamido)-5-hexynohydroxamate; 1H NMR (250 MHz, MeOD) δ: 1.4 (s, 9H), 1.7 (m, 1H), 1.9 (m, 1H), 2.3 (m, 3H), 3.2 (s, 3H), 3.8 (s, 3H), 4.7 (m, 1H)

iii) N2-[N-[N-[N-[N-[3-(tert-Butoxycarbonyl)propionyl]-O-tert-butyl-L-α-aspartyl]-O-tert-butyl-L-α-glutamyl]-2-methyl-L-phenylalanyl]-3-methyl-L-valyl]-N 1-[1(S)-(dimethoxymethyl)-4-pentynyl]-L-leucinamide; MS: m/e 1079.5 [M+Na]+

EXAMPLE 39

In an analogous manner to that described in Example 10, but using N-(tert-butoxycarbonyl)-L-methionine in place of N-(tert-butoxycarbonyl)-L-allylglycine there was obtained 2(RS)-[[N-[N-[N-[N-[N-(3-carboxypropionyl)-L-α-aspartyll-L-α-glutamyl]-2-methyl-L-phenylalanyl]-3-methyl-L-valyl]-L-leucyl]aminol-4-(methylthio) butyraldehyde; MS: m/e 865.3 [M+H]+.

The starting material was prepared in an analogous manner to that described in Example 10 via the following intermediates:

i) N,O-Dimethyl 2(S)-(tert-butoxyformamido)-4-(methylthio)butyrohydroxamate; 1H NMR (250 MHz, CDCl3) δ: 1.4 (s, 9H), 1.75 (m, 1H), 2.0 (m, 1H), 2.05 (s, 3H), 2.5 (m, 2H), 3.2 (s, 3H), 3.75 (s, 3H), 4.7 (m, 1H), 5.2 (m, 1H).

ii) N2-[N-[N-[N-[3-(tert-Butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1(S)-(dimethoxymethyl)-2-(methylthio)propyl]-L-leucinamide; MS: m/e 1047.5 [M+H-MeOH]+.

EXAMPLE 40

In an analogous manner to that described in Example 10, but using S-(3-phenylpropyl)-L-cysteine in place of L-allylglycine hydrochloride there was obtained 2(R)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino]-2-[3-(phenyl)propylthio]propionaldehyde; MS: m/e 955.4 [M+H]+.

The starting material was prepared in an analogous manner to that described in Example 10 via the following intermediates:

i) N-(tert-Butoxycarbonyl)-S-(3-phenylpropyl)-L-cysteine; 1H NMR (250 MHz, CDCl3) δ: 1.4 (s, 9H), 1.9 (m, 2H), 2.55 (t, 2H), 2.7 (t, 2H), 3.0 (m, 2H), 4.5 (m, 1H), 5.4 (m, 1H), 7.2 (m, 5H).

ii) N,O-Dimethyl 2(S)-(tert-butoxyformamido)-3-(3-phenyl-propylthio)propionohydroxamate; 1H NMR (250 MHz, CDCl3) δ: 1.4 (s, 9H), 1.9 (m, 2H), 2.5 (t, 2H), 2.7 (t, 2H), 2.8 (m, 2H), 3.2 (s, 3H), 3.7 (s, 3H), 4.8 (m, 1H), 5.3 (m, 1H), 7.2 (m, 5H).

iii) N2-[N-[N-[N-[N-[3-(tert-Butoxycarbonyl)propionyl]-O-tert-butyl-L-α-aspartyl]-O-tert-butyl-L-α-glutamyl]-2-methyl-L-phenylalanyl]-3-methyl-L-valyl]-N1-[1 (R)-(dimethoxymethyl)-2-(3-phenylpropylthio)ethyl]-L-leucinamide; MS: m/e 1191.8 [M+Na]+.

EXAMPLE 41

In an analogous manner to that described in Example 1, but sing N,O-Dimethyl 2(S)-(tert-butoxyformamido) hexanohydroxamate in place of N,O-Dimethyl 2(S)-(tert-butoxyformamido)butyrohydroxamate and N-(9-fluorenylmethoxycarbonyl)-D-valine in place of N-(9-fluorenylmethoxycarbonyl)-O-tert-butyl-L-α-glutamic acid there was obtained 2(S)-[[N-[N-[N-N-(3-carboxypropionyl)-L-α-aspartyl]-D-valyl]-2-methyl-L-phenyl-alanyl]-3-methyl-L-valyl]-L-leucyl]amino]hexanal; MS: m/e 817.4 [M+H]+.

The starting material was prepared in an analogous manner to that described in Example 1 via the following intermediates:

i) N-[N-[N-[N-[(9-Fluorenyl)methoxycarbonyl]-D-valyl]-2-methyl-L-phenylalanyl]-3-methyl-L-valyl]-L-leucine benzyl ester; MS: m/e 817.4 [M+H]+.

ii) N N-[N-[N-[N-[(9-Fluorenyl)methoxycarbonyl]-O-tert-butyl-L-α-aspartyl]-D-valyl]-2-methyl-L-phenylalanyl]-3-methyl-L-valyl] L-leucine benzyl ester; MS: m/e 988.4 [M+H]+.

iii) N-[N-[N-[N-[N-3-(tert-Butoxycarbonyl)propionyl]-O-tert-butyl-L-α-aspartyl]-D-valyl]-2-methyl-L-phenylalanyl]-3-methyl-L-valyl]-L-leucine benzyl ester; MS: m/e 922.5 [M+H]+.

iv) N-[N-[N-[N-[N-3-(tert-Butoxycarbonyl)propionyl]-O-tert-butyl-L-α-aspartyl]-D-valyl]-2-methyl-L-phenylalanyl]-3-methyl-L-valyl]-L-leucine; MS: m/e 832.5 [M+H]+.

v) N2-[N-[N-[N-[N-3-(tert-Butoxycarbonyl)propionyl]-O-tert-butyl-L-α-aspartyl]-D-valyl]-2-methyl-L-phenylalanyl]-3-methyl-L-valyl]-N1-[1(S)-(dimethoxymethyl)pentyl]-L-leucinamide; MS: m/e 997.5 [M+Na]+.

EXAMPLE 42

In an analogous manner to that described in Example 1, but using N,O-dimethyl 2(S)-(tert-butoxyformamido) hexanohydroxamate in place of N,O-dimethyl 2(S)-(tert-butoxyformamido)butyrohydroxamate, using N-(9-fluorenylmethoxycarbonyl)-D-valine in place of N-(9-fluorenylmethoxycarbonyl)-O-tert-butyl-L-α-glutamic acid and using O-tert-butyl-N-[(9-florenyl)methoxycarbonyl]-L-serine in place of N-(9-fluorenylmethoxycarbonyl)-O-tert-butyl-L-α-aspartic acid there was obtained 2(S)-[[N-[N-[N-[N-[N-(3-carboxypropionyl)-L-seryl]-D-valyl]-2-methyl-L-phenyl-alanyl]-3-methyl-L-valyl]-L-leucyl]amino]hexanal; MS: m/e 789.3 [M+H]+.

The starting material was prepared in an analogous manner to that described in Example 1 via the following intermediates:

i) N-[N-[N-[N-[N-[(9-Fluorenyl)methoxycarbonyl]-O-tert-butyl-L-seryl]-D-valyl]-2-methyl-L-phenylalanyl]-3-methyl-L-valyl]-L-leucine benzyl ester; MS: m/e 960.4 [M+H]+.

ii) N-[N-[N-[N-[N-3-(tert-Butoxycarbonyl)propionyl]-O-tert-butyl-L-seryl]-D-valyl]-2-methyl-L-phenylalanyl]-3-methyl-L-valyl]-L-leucine benzyl ester; MS: m/e 894.5 [M+H]+.

iii) N-[N-[N-[N-[N-3-(tert-Butoxycarbonyl)propionyl]-O-tert-butyl-L-seryl]-D-valyl]-2-methyl-L-phenylalanyl]-3-methyl-L-valyl]-L-leucine; MS: m/e 804.4 [M+H]+.

iv) N2-[N-[N-[N-[N-3-(tert-Butoxycarbonyl)propionyl]-O-tert-butyl-L-seryl]-D-valyl]-2-methyl-L-phenylalanyl]-3-methyl-L-valyl]-N1-[1(S)-(dimethoxymethyl)pentyl]-L-leucinamide; MS: m/e 969.7 [M+Na]+.

EXAMPLE 43

In an analogous manner to that described in Example 1, but using N,O-dimethyl 2(S)-(tert-butoxyformamido)

hexanohydroxamate in place of N,O-dimethyl 2(S)-(tert-butoxyformamido)butyrohydroxamate using N-(9-fluorenylmethoxycarbonyl)-D-valine in place of N-(9-fluorenylmethoxycarbonyl)-O-tert-butyl-L-α-glutamic acid, using O-tert-butyl-N-[(9-florenyl)methoxycarbonyl]-L-serine in place of N-(9-fluorenylmethoxycarbonyl)-O-tert-butyl-L-α-aspartic acid and using acetic anhydride in place of tert-butyl hydrogen succinate there was obtained 2(S)-[[N-[N-[N-[N-(N-acetyl-L-seryl)-D-valyl]-2-methyl-L-phenylalanyl]-3-methyl-L-valyl]-L-leucyl]amino]hexanal; MS: m/e 731.3 [M+H]+.

The starting material was prepared in an analogous manner to that described in Example 1 via the following intermediates:

i) N-[N-[N-[N-(N-acetyl-O-tert-butyl-L-seryl)-D-valyl]-2-methyl-L-phenylalanyl]-3-methyl-L-valyl]-L-leucine; MS: m/e 690.4 [M+H]+.

ii) N2-[N-[N-[N-(N-acetyl-O-tert-butyl-L-seryl)-D-valyl]-2-methyl-L-phenylalanyl]-3-methyl-L-valyl]-N1-[1(S)-(dimethoxy-methyl)pentyl]-L-leucinamide; MS: mle 833.5 [M+H]+.

The reaction with acetic anhydride was carried out as follows:

0.5 ml of N-ethylmorpholine and 0.37 ml of acetic anhydride were added in sequence to a solution of 1.95 g of N-[N-[N-[N-(O-tert-butyl-L-seryl)-D-valyl]-2-methyl-L-phenylalanyl]-3-methyl-L-valyl]-L-leucine benzyl ester in 70 ml of anhydrous dichloromethane. The mixture was stirred at room temperature for 1 hour and was then washed in sequence with 5% aqueous citric acid solution, saturated aqueous sodium bicarbonate solution and saturated brine. The organic phase was dried over anhydrous magnesium sulphate and evaporated. Chromatography of the residue on silica using 5% methanol in dichloromethane for the elution gave afforded 1.45 g of N-[N-[N-[N-(N-acetyl-O-tert-butyl-L-seryl)-D-valyl]-2-methyl-L-phenylalanyl]-3-methyl-L-valyl]-L-leucine benzyl ester; MS: m/e 780.6 [M+H]+.

EXAMPLE 44

59 mg (0.058 mmol) of N1-[4-bromo-1(RS)-(4,4,5,5-tetramethyl-1,3,2-dioxoborolan-2-yl)butyl]-N2-[N-[N-[N-[N-(3-carboxypropionyl)-L-α-aspartyl]-L-α-glutamyl]-2-methylL-phenylalanyl]-3-methyl-L-valyl]-L-leucinamide were dissolved in 3 ml of trifluoroacetic acid and 3 ml of dichloromethane. 5 drops of water were added and the solution was stirred at room temperature for 3 hours. The solution was diluted with toluene and evaporated. The residue was triturated with diethyl ether and the resulting solid was filtered off and dried and then redissolved in 5 ml of trifluoroacetic acid and 5 ml of dichloromethane. The solution was stirred at room temperature for 3 hours and then diluted with toluene and evaporated. The residue was triturated with diethyl ether and the solid obtained was filtered off and dried to give 30 mg of 4-bromo-1(RS)-[[N-[N-[N-[N-[N-(3-carboxypropionyl)-L-α-aspartyl]-L-α-glutamyl]-2-methylL-phenylalanyl]-3-methyl-L-valyl]-L-leucyl]amino]butylboronic acid in the form of a solid; MS: m/e 911.3 [M+H–H₂O]+.

The starting material was prepared as follows:

i) 1.7 ml (1.7 mmol) of 1 M lithium bis(trimethylsilyl)amide in tetrahydrofuran were added dropwise to a solution of 0.5 g (1.7 mmol) of 2-(4-bromo-1(RS)-chlorobutyl)-4,4,5,5-tetramethyl-1,3,2-dioxaborolane (prepared according to EP-A-0 293 881) in 5 ml of tetrahydrofuran under nitrogen at −78° C. The solution was then stirred overnight at room temperature. The solvent was removed by evaporation and the residue was taken up in diethyl ether. Insoluble material was removed by filtration and the solvent was removed by evaporation to give 0.63 g of product which was immediately redissolved in diethyl ether and cooled to 0° C. 0.34 ml 0.34 ml (5.0 mmol) of trifluoroacetic acid was added and the solution was stirred at 0° C. for 30 minutes. The solution was evaporated and the residue was evaporated with toluene to give 0.58 g of α-(RS)-3-bromopropyl-4,4,5,5-tetramethyl-1,3,2-dioxaborolane-2-methylamine trifluoroacetate (1:1) as a brown oil which was used in the next step without purification.

ii) 0.20 g (0.22 mmol) of N-[N-[N-[N-(tert-butoxycarbonyl)-O-tert-butyl-L-α-aspartyl]-O-tert-butyl-L-α-glutamyl]-2-methyl-L-phenylalanyl]-3-methyl-L-valyl]-L-leucine was dissolved in 2 ml of dimethylformamide and 6 ml of dichloromethane. 0.2 ml (1.52 mmol) of N-methylmorpholine was added and the solution was cooled to −10° C. under a nitrogen atmosphere. 44 mg (0.3 mmol) of isobutyl chloroformate were added and the solution was stirred for 15 minutes at −10° C. 0.3 g (0.66 mmol) of a(RS)-3-bromopropyl-4,4,5,5-tetramethyl-1,3,2-dioxaborolane-2-methylamine trifluoroacetate (1:1) was added and the mixture was stirred at room temperature for 5 hours. Dichloromethane was added and the solution was extracted with 2M hyrochloric acid and water and then dried over anhydrous sodium sulphate. After evaporation there was obtained 0.122 g of N2-[N-[N-[N-[N-(tert-butoxycarbonyl)-O-tert-butyl-L-α-aspartyl]-O-tert-butyl-L-α-glutamyl]-2-methyl-L-phenylalanyl]-3-methyl-L-methyl-L-valyl]-N1-[4-bromo-1 (RS)-(4,4,5,5-tetramethyl-1,3,2-dioxaborolan-2-yl)butyl]-L-leucinamide in the form of a solid; MS: m/e 1079.5 [M+H−100]+.

iii) 115 mg (0.098 mmol) of N2-[N-[N-[N-[N-(tert-butoxycarbonyl)-O-tert-butyl-L-α-aspartyl]-O-tert-butyl-L-α-glutamyl]-2-methyl-L-phenylalanyl]-3-methyl-L-valyl]-N1-[4-bromo-1(RS)-(4,4,5,5-tetramethyl-1,3,2-dioxaborolan-2-yl)butyl]-L-leucinamide were dissolved in 3 ml of trifluoroacetic acid and 3 ml of dichloromethane. 5 drops of water were added and the solution was stirred at room temperature for 3 hours. The solution was diluted with toluene and evaporated. The residue was triturated with ether and the resulting solid was filtered off and dried to give 72 mg of N1-[4-bromo-1(RS)-(4,4,5,5-tetramethyl-1,3,2-dioxoborolan-2-yl)butyl]-N2-[N-[N-[N-[N-(3-carboxypropionyl)-L-α-aspartyl-L-α-glutamyl]-2-methyl-L-phenylalanyl]-3-methyl-L-methyl-valyl]-L-leucinamide as a white solid; MS: m/e 911.3 [M+H−100]+

EXAMPLE 45

In an analogous manner to that described in Example 23, but replacing N-[(9-fluorenyl)methoxycarbonyl]-O-tert-butyl-L-tyrosine with N-[(9-fluorenyl)methoxycarbonyl]-O-tert-butyl-L-aspartic acid and replacing N-[(9-fluorenyl)methoxycarbonyl]-3-methyl-L-valine with N-[(9-fluorenyl)methoxycarbonyl]-L-2-cyclohexylglycine there was obtained 1 (RS)-[[N-[N-[N-[N-[N-(3-carboxypropionyl)-L-α-aspartyl]-L-α-glutamyl]-2-methylL-phenylalanyl]-L-2-cyclohexylglycyl]-L-leucyl]amino]propylboronic acid as a white solid; MS: m/e 843.4 [M+H−H₂O]+.

EXAMPLE 46

In an analogous manner to that described in Example 23, but replacing N-[(9-fluorenyl)methoxycarbonyl]-O-tertbutyl-L-tyrosine with N-[(9-fluorenyl)methoxycarbonyl]-O-tert-butyl-L-aspartic acid and replacing N-[(9-fluorenyl)methoxycarbonyl-2-methyl-L-phenylalanine with N-[(9-fluorenyl)methoxycarbonyl]-L-2-cyclohexylglycine there was obtained 1 (RS)-[[N-[N-[N-[N-(3-carboxypropionyl)-L-α-aspartyl]-L-α-glutamyl]-L-2-cyclohexyl-glycyl]-3-methyl-L-valyl]-L-leucyl]amino] propylboronic acid as a white solid; MS: m/e 795.5 [M+H–H$_2$O]$^+$.

EXAMPLE 47

In an analogous manner to Example 4, by replacing N-[(9-fluorenyl)methoxycarbonyl]-3-(2-naphthyl)-D-alanine with N-[(9-fluorenyl)methoxycarbonyl]-3-cyclohexyl-L-alanine there was obtained 2(RS)-[[N-[N-[N-[N-[N-(3-carboxypropionyl)-L-α-aspartyl]- 3-cyclohexyl-L-alanyl]-2-methyl-L-phenylalanyl]-3-methyl-L-valyl]-L-leucyl]amino]-4,4,4-trifluorobutyraldehyde as a white solid; MS m/e 897.6 [M+H].

EXAMPLE 48

In an analogous manner to Example 4, by replacing N-[(9-fluorenyl)methoxycarbonyl]-3-(2-naphthyl)-D-alanine with N-[(9-fluorenyl)methoxycarbonyl]-D-valine and replacing N-[(9-fluorenyl)methoxycarbonyl]-O-t-butyl-L-α-aspartic acid with N-[(9-fluorenyl)methoxycarbonyl]-O-t-butyl-L-serine there was obtained 2(RS)-[[N-[N-[N-[N-[N-(3-carboxypropionyl)-L-seryl]-D-valyl]-2-methyl-L-phenylalanyl]-3-methyl-L-valyl]-L-leucyl]amino]-4,4,4-trifluorobutyraldehyde as a white solid; MS: m/e 815.5 [M+H].

EXAMPLE 49

In an analogous manner to Example 4, by replacing N-[(9-flurenyl)methoxycarbonyl]-3-(2-naphthyl)-D-alanine with [(9-fluorenyl)methoxycarbonylI-D-norleucine there was obtained 2(RS)-[[N-[N-[N-[N-[N-(3-carbonylpropionyl)-L-a-aspartyl]-D-norleucyl]-2-methyl-L-phenylalanyl]-3-methyl-L-valyl]-L-leucyl]amino]-4,4,4-trifluorobutyraldehyde as a white solid;MS: m/e 857.4 [M+H].

EXAMPLE 50

In an analogous manner to Example 4, by replacing N-[(9-fluorenyl)methoxycarbonyl]-3-(2-naphthyl)-D-alanine with N-[(9-fluorenyl)methoxycarbonyl]-D-norvaline there was obtained 2(RS)-[[N-[N-[N-[N-[N-(3-carboxypropionyl)-L-α-aspartyl]-D-norvalyl]-2-methyl-L-phenylalanyl]-3-methyl-L-valyl]-L-leucyl]-amino]-4,4,4-trifluorobutyraldehyde as a white solid; MS: m/e 843.4 [M+H].

EXAMPLE 51

In an analogous manner to Example 4, by replacing N-[(9-fluorenyl)methoxycarbonyl]-3-(2-naphthyl)-D-alanine with N-[(9-fluorenyl)methoxycarbonyl]-D-2-cyclohexylglycine there was obtained 2(RS)-[[N-[N-[N-[N-[N-(3-carboxypropionyl)-L-α-aspartyl]-D-2-cyclohexylglycyl]-2-methyl-L-phenylalanyl]-3-methyl-L-valyl]-L-leucyl]amino]-4,4,4-trifluorobutyraldehyde as a white solid, MS: m/e 897.4 [M+H].

EXAMPLE 52

In an analogous manner to Example 4, by replacing N-[(9-fluorenyl)methoxycarbonyl]-3-(2-naphthyl)-D-alanine with N-[(9-fluorenyl)methoxycarbonyl]-4-nitro-D-phenylalanine there was obtained 2(RS)-[[N-[N-[N-[N-(3-carboxypropionyl)-L-α-aspartyl]-4-nitro-D-phenylalanyl]-2-methyl-L-phenylalanyl]-3-methyl-L-valyl]-L-leucyl]amino]-4,4,4-trifluorobutyraldehyde as a white solid; MS: m/e 936.3 [M+H].

EXAMPLE 53

In an analogous manner to Example 4, by replacing N-[(9-fluorenyl)methoxycarbonyl]-3-methyl-L-valine with N-[(9-fluorenyl)methoxycarbonyl]-L-2-cyclohexylglycine and by replacing N-[(9-fluorenyl)methoxycarbonyl]-3-(2-naphthyl)-D-alanine with N-[(9-fluorenyl)methoxycarbonyl]-O-tert-butyl-L-α-glutamic acid there was obtained 2(RS)-[[N-[N-[N-(N-[N-(3-carboxypropionyl)-L-α-aspartyl]-L-α-glutamyl]-2-methyl-L-phenylalanyl]-L-2-cyclohexylglycyl]-L-leucyl]amino]-4,4,4-trifluorobutyraldehyde as a white solid; MS: m/e 899.5 [M+H].

EXAMPLE 54

In an analogous manner to Example 4, by replacing N-[(9-methoxycarbonyl]-3-(2-methylphenyl)-L-alanine with N-[(9-methoxycarbonyl]-L-2-cyclohexylglycine and by replacing N-[(9-fluorenyl)methoxycarbonyl]-3-(2-naphthyl)-D-alanine with N-[(9-fluorenyl)methoxycarbonyl]-O-t-butyl-L-α-glutamic acid there was obtained 2(RS)-[[N-[N-[N-[N-(3-carboxypropionyl)-L-α-aspartyl]-L-α-glutamyl]-L-2-cyclohexylglycyl]-3-methyl-L-valyl]-L-leucyl]-amino]-4,4,4-trifluorobutyraldehyde as a white solid; MS: m/e 851.4 [M+H].

EXAMPLE 55

In an analogous manner to Example 4, by replacing N-[(9-fluorenyl)methoxycarbonyl]-3-(2-naphthyl)-D-alanine with N-[(9-fluorenyl)methoxycarbonyl]-O-t-butyl-L-α-glutamic acid and by replacing tert-butyl hydrogen succinate with 3-acetamidobenzoic acid there was obtained 2(RS)-[[N-[N-[N-[N-[N-(3-acetamido-benzoyl)-L-α-aspartyl]-L-α-glutamyl]-2-methyl-L-phenylalanyl]-3-methyl-L-valyl]-L-leucyl]amino-4,4,4-trifluororbutyraldehyde as a white solid; MS: m/e 934.4 [M+H].

EXAMPLE 56

In an analogous manner to Example 4, by replacing N-[(9-fluorenyl)methoxycarbonyl]-3-(2-naphthyl)-D-alanine with N-[(9-fluorenyl)methoxycarbonyl]-O-t-butyl-L-α-glutamic acid and by rep[lacing tert-butyl hydrogen succinate with 4-acetamido-3-nitrobenzoic acid there was obtained 2(RS)-[[N-[N-[N-[N-(4-acetamido-3-nitrobenzoyl)-L-α-aspartyl]-L-α-glutamyl]-2-methyl-L-phenylalanyl-3-methyl-L-valyl]-L-leucyl]amino]-4,4,4-trifluoro-butyraldehyde as a white solid; MS: m/e 979.4 [M+H].

EXAMPLE 57

In an analogous manner to Example 4, by replacing N-[(9-fluorenyl)methoxycarbonyl]-3-(2-naphthyl)-D- alanine with N-[(9-fluorenyl)methoxycarbonyl]-O-tert-butyl-L-α-glutamic acid and by replacing tert-butyl hydrogen succinate with 4-acetamidobenzoic acid there was obtained 2(RS)-[[N-[N-[N-[N-[N-(4-acetamidobenzoyl)-L-α-aspartyl]-L-α-glutamyl]-2-methyl-L-phenylalanyl]-3-methyl-L-valyl]-L-leucyl]amino]-4,4,4-trifluorobutyraldehyde as a white solid; MS: m/e 934.4 [M+H].

EXAMPLE 58

In an analogous manner to Example 4, by replacing N-[(9-fluorenyl)methoxycarbonyl]-3-(2-naphthyl)-D-alanine with N-[(9-fluorenyl)methoxycarbonyl]-O-tert-L-α-glutamic acid and by replacing tert-butyl hydrogen succinate with 3,5-dichlorobenzoic acid there was obtained 2(RS)-[[N-[N-[N-[N-[N-(3,5-dichloro-benzoyl)-L-α-aspartyl]-L-α-glutamyl]-2-methyl-L-phenylalanyl]-3-methyl-L-valyl]-L-leucyl]amino]-4,4,4-trifluorobutyraldehyde as a white solid; MS: m/e 945.3 [M+H].

EXAMPLE 59

0.78 g of 0.235 mmol/g 5-[2-[1 (RS)-[[N-[(9-fluorenyl)-methoxycarbonyl]-L-leucyl]amino]propyl]-4(RS),5,5-trimethyl-1,3,2-dioxoborolan-4-yl]-3(RS)-methyl-N-[α(RS)-(4-methyl-phenyl)benzyl]valeramide-polystyrene conjugate was swollen in dimethylformamide for 20 minutes and then suspended and agitated in dimethylformamide/piperidine (4:1). After 5 minutes the resin was drained and then resuspended in and agitated with dimethylformamide/piperidine (4:1) for a further five minutes. The resin was then drained and washed five times with dimethylformamide.

The resin was then suspended in a solution of 0.4 g, 1.08 mmol of N-[(9-fluorenyl)methoxycarbonyl]-3-methyl-L-valine in dimethylformamide and then a mixture of 0.42 g (1.08 mmol) 2-(1H-benzotriazol-1-yl)-1,1,3,3-tetramethyluronium tetrafluoroborate and 0.25 ml (2.2 mmol) of N-methylmorpholine dissolved in dimethylformamide was added. After agitating for 40 minutes the resin was drained and washed five times with dimethylformamide.

The resin was resuspended in and agitated with dimethylformamide/piperidine (4:1). After 5 minutes the resin was drained, resuspended in and agitated with dimethylformamide/piperidine (4:1) for a further 5 minutes. Then the resin was drained and washed five times with dimethyl formamide.

The resin was then suspended in a solution of 0.44 g (1.08 mmol) of N-[(9-fluorenyl)methoxycarbonyl]-3-(2-methylphenyl)-L-alanine in dimethylformamide and then a mixture of 0.42 g 2-(1H-benzotriazol-1-yl)-1,1,3,3-tetramethyluronium tetrafluoroborate and 0.25 ml (2.2 mmol) of N-methylmorpholine dissolved in dimethylformamide was added. After agitating for 40 minutes the resin was drained and washed five times with dimethylformamide.

The resin was resuspended in and agitated with dimethylformamide/piperidine (4:1). After 5 minutes the resin was drained, resuspended in and agitated with dimethylformamide/piperidine (4:1) for a further 5 minutes. Then the resin was drained and washed five times with dimethyl formamide.

The resin was then suspended in a solution of 0.37 g (1.08 mmol) of N-[(9-fluorenyl)methoxycarbonyl]-D-valine in dimethylformamide and then a mixture of 0.42 g of 2-(1H-benzotriazol-1-yl)-1,1,3,3-tetramethyluronium tetrafluoroborate and 0.25 ml (2.2 mmol) of N-methylmorpholine dissolved in dimethylformamide was added. After agitating for 40 minutes the resin was drained and washed five times with dimethylformamide.

The resin was resuspended in and agitated with 0.7 ml of dimethylformamide/piperidine (4:1). After 5 minutes the resin was drained, resuspended in and agitated with dimethylformamide/piperidine (4:1) for a further 5 minutes. Then, the resin was drained and washed five times with 1 ml of dimethylformamide.

98 mg of this resin were then suspended in a solution of 0.06 g (0.19 mmol) of N-(benzyloxycarbonyl)-O-tert-butyl-L-α-aspartic acid in dimethylformamide and then a mixture of 0.06 g (0.19 mmol) of 2-(1 H-benzotriazol-1-yl)-1,1,3,3-tetramethyluronium tetrafluoroborate and 0.1 ml (0.88 mmol) of N-methylmorpholine dissolved in dimethylformamide was added. After agitating for 40 minutes the resin was drained and washed three times with dimethylformamide, three times with ethyl acetate and three times with dichloromethane.

1 ml of dichloromethane was added to the resin which was then treated with 3 ml of a 9:1 mixture of trifluoroacetic acid and water and then agitated for 30 minutes. The resin was then filtered off and washed with dichloromethane. The filtrate and washings were combined and evaporated and then co-evaporated with toluene. The residue was triturated with diethyl ether and dried. There were obtained 12 mg of 1 (RS)-[[N-[N-[N-[N-[N-(benzyloxycarbonyl)-L-α-aspartyl]-D-valyl]-2-methyl-L-phenylalanyl]-3-methyl-L-valyl]-L-leucyl]amino]propylboronic acid; MS: m/e 821.4 [M+H−H$_2$O]$^+$.

EXAMPLE 60

200 mg (0.18 mmol) of N2-[N-[N-[N-[N-(tert-butoxycarbonyl)-O-tert-butyl-L-α-aspartyl]-O-tert-butyl-L-α-glutamyl]-2-methyl-L-phenylalanyl]-3-methyl-L-valyl]-N1-[4-fluoro-1(RS)-(4,4,5,5-tetramethyl-1,3,2-dioxaborolan-2-yl)butyl]-L-leucinamide were dissolved in 4.75 ml of trifluoroacetic acid and 0.25 ml of water. 2 ml of dichloromethane were added and the solution was stirred at room temperature for 3 hours. The solution was diluted with toluene and evaporated. The residue was triturated with diethyl ether and the resulting solid was filtered off and dried to give 95 mg of 4-fluoro-1(RS)-[[N-[N-[N-[N-[N-(3-carboxypropionyl)-L-α-aspartyl]-L-α-glutamyl]-2-methyl-L-phenylalanyl]-3-methyl-L-valyl]-L-leucyl]amino] butylboronic acid; MS: m/e 849.4 [M+H−H$_2$O]$^+$ The starting material was prepared as follows:
i) 2.5 ml (25 mmol) of borane-dimethyl sulphide (1:1) complex were dissolved in 50 ml of dimethoxyethane and the solution was cooled to 0° C. under nitrogen. 5.3 ml (52.5 mmol) of cyclohexene were then added. The solution was stirred at 0° C. for 15 minutes, then at room temperature for 1 hour and then cooled to −10° C. 1.6 g (27 mmol) of 3-fluoropropene were condensed and then added to the foregoing solution which was then stirred at room temperature under a dry ice condenser. After 1 hour the condenser was removed and stirring was continued for a further 1 hour. 3.9 g (52 mmol) of trimethylamine N-oxide were added and the solution was stirred for 1 hour. 3.1 g (26.3 mmol) of 2,3-dimethyl-2,3-butanediol were added and the solution was stirred for 16 hours. The solution was evaporated and the residue was distilled. The distillate boiling at 35–65° C./1mm Hg was collected and purified by chromatography on silica gel using diethyl ether/ hexane (1:9) for the elution to give 1.67 g of 4,4,5,5-tetramethyl-2-(3-fluoropropyl)-1,3,2-dioxaborolane as a colourless oil; $^1$H NMR (250 MHz, CDCl$_3$) δ: 0.75–0.85 (m, 2H), 1.25 (s, 12H), 1.7-1.9 (m, 2H), 4.28 (t, 1H), 4.48 (t, 1H).

ii) 1.3 ml (8.8 mmol) of diisopropylamine and 5.5 ml (8.8 mmol) of butyllithium in hexane were added to 7 ml of tetrahydrofuran at −78° C. The cooled solution was added to a solution of 1.65 g (8.8 mmol) of 4,4,5,5-tetramethyl-2-(3-fluoropropyl)-1,3,2-dioxaborolane in 0.7 ml of dichloromethane, 15 ml of cyclohexane and 8 ml of tetrahydrofuran at −20° C. under nitrogen. The solution was then stirred for 16 hours while slowly warming to room temperature. The solution was partitioned between 2M hydrochloric acid, brine and ethyl acetate, and the aqueous layer was extracted with ethyl acetate. The organic extracts were combined, washed with brine and dried over sodium sulphate. After evaporation the residue was purified by chromatography on silica gel using diethyl ether/hexane (1:9) for the elution to give 1.0 g of 2-(4-fluoro-1(RS)-chlorobutyl)-4,4,5,5-tetramethyl-1,3,2-dioxaborolane as a colourless oil; $^1$H NMR (250 MHz, CDCl$_3$) δ: 0.75–0.85 (m, 2H), 1.3 (s, 12H), 1.9–2.1 (m, 2H), 3.45 (m, 1H) 4.35 (m, 1H), 4.55 (m, 1H).

iii) 4.2 ml (4.2 mmol) of 1M lithium bis(trimethylsilyl) amide in tetrahydrofuran were added dropwise to a solution of 1.0 g (4.2 mmol) of 2-(4-fluoro-1(RS)-chlorobutyl)-4,4,5,5-tetramethyl-1,3,2-dioxaborolane in 7 ml of tetrahydrofuran under nitrogen at −78° C. The solution was then stirred overnight at room temperature. The solvent was removed by evaporation and the residue was taken up in diethyl ether. Insoluble material was removed by filtration and the solvent was removed by evaporation to give 1.53 g of material which was immediately redissolved in 7 ml of diethyl ether and cooled to 0° C. 0.95 ml (12.6 mmol) of trifluoroacetic acid was added and the solution was stirred at 0° C. for 30 minutes. The solution was evaporated and the residue was evaporated with toluene to give 1.36 g of α(RS)-3-fluoropropyl-4,4,5,5-tetramethyl-1,3,2-dioxaborolane-2-methylamine trifluoroacetate (1:1) as a brown oil which was used in the next step without further purification.

iv) 0.20 g (0.22 mmol) N-[N-[N-[N-(tert-butoxycarbonyl)-O-tert-butyl-L-α-aspartyl]-O-tert-butyl-L-α-glutamyl]-2-methyl-L-phenylalanyl]-3-methyl-L-valyl]-L-leucine was dissolved in 2 ml of dimethylformamide and 4 ml of dichloromethane. 0.2 ml (1.52 mmol) of N-methylmorpholine was added and the solution was cooled to −10° C. under a nitrogen atmosphere. 40 mg (0.27 mmol) of isobutyl chloroformate were added and the solution was stirred for 10 minutes at −100° C. 0.2 g (0.44 mmol) of α(RS)-3-fluoropropyl-4,4,5,5-tetramethyl-1,3,2-dioxaborolane-2-methylamine trifluoroacetate (1:1) was added and the mixture was stirred at room temperature for 16 hours. Dichloromethane was added and the solution was washed with 2M hydrochloric acid and water and then dried over anhydrous sodium sulphate. After evaporation there was obtained 0.21 g of N2-[N-[N-[N-[N-(tert-butoxycarbonyl)-O-tert-butyl-L-α-aspartyl]-O-tert-butyl-L-α-glutamyl]-2-methyl-L-phenylalanyl]-3-methyl-L-valyl]-N1-[4-fluoro-1(RS)-(4,4,5,5-tetramethyl-1,3,2-dioxaborolan-2-yl)butyl]-L-leucinamide in the form of a solid; MS: m/e 1017.3 [M+H-100]$^+$.

EXAMPLE 61

In an analogous manner to that described in Example 4, by replacing N-[(9-fluorenyl)methoxycarbonyl]-3-(2-naphthyl)-D-alanine with N-[(9-fluorenyl)methoxycarbonyl]-O-tert-butyl-L-α-glutamic acid and by replacing N-[(9-fluorenyl)methoxycarbonyl]-2-methyl-L-phenylalanine with N-[(9-fluorenyl)methoxycarbonyl]-4-chloro-L-phenylalanine there was obtained 2(RS)-[[N-[N-[N-[N-[N-(3-carboxypropionyl)-L-α-aspartyl-L-α-glutamyl]-4-chloro-L-phenylalanyl]-3-methyl-L-valyl]-L-leucyl]amino]-4,4,4-trifluorobutyraldehyde as a white solid; MS: m/e 893.3 [M+H].

EXAMPLE 62

In an analogous manner to that described in Example 4, by replacing N-[(9-fluorenyl)methoxycarbonyl]-3-(2-naphthyl)-D-alanine with N-[(9-fluorenyl)methoxycarbonyl]-O-tert-butyl-L-α-glutamic acid, by replacing N-[(9-fluorenyl)methoxycarbonyl]-O-tert-butyl-L-α-aspartic acid with N-(benzyloxycarbonyl)-O-tert-butyl-L-α-aspartic acid and by omitting the reaction with tert-butyl succinate there was obtained 2(RS)-[[N-[N-[N-[N-(benzyl-oxycarbonyl)-L-α-aspartyl]-L-α-glutamyl]-2-methyl-L-phenyl-alanyl]-3-methyl-L-valyl]-L-leucyl] amino]-4,4,4-trifluoro-butyraldehyde as a white solid; MS: m/e 907.4 [M+H].

EXAMPLE 63

88 mg (0.09 mmol) of N2-[N-[N-[N-(3-carboxypropionyl)-L-α-aspartyl]-L-α-glutamyl]-4-chloro-2-methyl-L-phenylalanyl]-3-methyl-L-valyl]-N1-[1(RS)-(4,4,5,5-tetramethyl-1,3,2-dioxoborolan-2-y;)-3-butenyl]-L-leucinamide were dissolved in 5 ml of trifluoroacetic acid and 5 ml of dichloromethane. 5 drops of water were added and the solution was stirred at room temperature for 4 hours. The solution was diluted with toluene and evaporated. The residue was triturated with diethyl ether and the resulting solid was filtered off and dried to give 72 mg of 1 (RS)-[[N-[N-[N-[N-[N-(3-carboxypropionyl)-L-α-aspartyl]-L-α-glutamyl]-4-chloro-2-methyl-L-phenylalanyl]-3-methyl-L-valyl]-L-leucyl]amino]-3-butenylboronic acid; MS: m/e 863 [M+H-H$_2$O]$^+$.

The starting material was prepared as follows:

i) In an analogous manner to Example 1 iii)–x), by replacing N-[(9-fluorenyl)methoxycarbonyl]-2-methyl-L-phenylalanine with N-[(9-fluorenyl)methoxycarbonyl]-4-chloro-2-methyl-L-phenylalanine there was obtained N-[N-[N-[N-[3-(tert-butoxy-carbonyl)propionyl]-O-tert-butyl-L-α-aspartyl]-O-tert-butyl-L-α-glutamyl]-4-chloro-2-methyl-L-phenylalanyl]-3-methyl-L-valyl]-L-leucine as a white solid; MS: m/e 952 [M+H]$^+$.

ii) 0.18 g (0.19 mmol) of N-[N-[N-[N-3-(tert-butoxycarbonyl)propionyl]-O-tert-butyl-L-α-aspartyl]-O-tert-butyl-L-α-glutamyl]-4-chloro-2-methyl-L-phenylalanyl]-3-methyl-L-valyl]-L-leucine was dissolved in 2 ml of dimethylformamide and 5 ml of dichloromethane. 0.1 ml (0.94 mmol) of N-methylmorpholine was added and the solution was cooled to −15° C. under a nitrogen atmosphere. 35 mg (0.25 mmol) of isobutylchloroformate were added and the solution was stirred for 10 minutes at −10° C. 0.12g (0.38 mmol) α(RS)-allyl-4,4,5,5-tetramethyl-1,3,2-dioxaborolane-2-methylamine trifluoroacetate (1:1) was added and the mixture was stirred at room temperature for 2 hours. The solution was diluted with dichloromethane, washed with 2M hydrochloric acid and water and dried over anhydrous sodium sulphate. After evaporation there was obtained 0.18 g of N2-[N-[N-[N-[N-[3-(tert-butoxycarbonyl)propionyl]-O-tert-butyl-L-α-aspartyl]-O-tert-butyl-L-α-glutamyl]-4-chloro-2-methyl-L-phenylalanyl]-3-methyl-L-valyl]-N1-[1(RS)-(4,4,5,5-tetramethyl-1,3,2-dioxaborolan-2-yl)-3-butenyl]-L-leucinamide in the form of a white solid; MS: m/e 1131.6 [M+H]$^+$.

iii) 166 mg (0.147 mmol) of N2-[N-[N-[N-[N-(3-(tert-butoxy-carbonyl)propionyl]-O-tert-butyl-L-α-aspartyl]-O-tert-butyl-L-α-glutamyl]-4-chloro-2-methyl-L-phenylalanyl]-3-methyl-L-valyl]-N1-[1 (RS)-(4,4,5,5-tetramethyl-1,3,2-dioxoborolan-2-yl)-3-butenyl]-L-leucinamide were dissolved in 5 ml of trifluoroacetic acid and 5 ml of dichloromethane. The solution was stirred at room temperature for 30 minutes, then diluted with toluene and evaporated. The residue was triturated with ether and the resulting solid was filtered off, dried and then redissolved in 5 ml of trifluoroacetic acid and 5 ml of dichloromethane. The solution was stirred at room temperature for 30 minutes, diluted with toluene and evaporated. The residue was triturated with diethyl ether and the resulting solid was filtered off and dried to give 100 mg of N2-[N-[N-[N-[N-(3-carboxypropionyl)-L-α-aspartyl]-L-α-glutamyl]-4-chloro-2-methyl-L-phenylalanyl]-3-methyl-L-valyl]-N1-[1(RS)-(4,4,5,5-tetramethyl-1,3,2-dioxoborolan-2-yl)-3-butenyl]-L-leucinamide as a white solid; MS: m/e 863 [M+H−100]$^+$.

The following Examples illustrate pharmaceutical preparations containing compounds of formula I:

EXAMPLE A

Tablets containing the following ingredients may be produced in a conventional manner:

| Ingredient | Per tablet |
|---|---|
| Compound of formula I | 10.0 mg |
| Lactose | 125.0 mg |
| Corn starch | 75.0 mg |
| Talc | 4.0 mg |
| Magnesium stearate | 1.0 mg |
| Total weight | 215.0 mg |

EXAMPLE B

Capsules containing the following ingredients may be produced in a conventional manner:

| Ingredient | Per capsule |
|---|---|
| Compound of formula I | 10.0 mg |
| Lactose | 165.0 mg |
| Corn starch | 20.0 mg |
| Talc | 5.0 mg |
| Capsule fill weight | 200.0 mg |

What is claimed is:

1. A compound of the formula

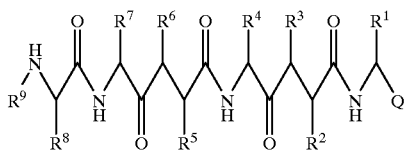

(III)

wherein $R^1$ is lower alkyl, halo-lower alkyl, cyano-lower alkyl, lower alkylthio-lower alkyl, aryl-lower alkylthio-lower alkyl, aryl-lower alkyl, heteroaryl-lower alkyl, lower alkenyl or lower alkynyl;

$R^2$ is lower alkyl, hydroxy-lower alkyl, carboxy-lower alkyl, aryl-lower alkyl, aminocarbonyl-lower alkyl or lower cycloalkyl-lower alkyl; and $R^3$ is hydrogen or lower alkyl; or $R^2$ and $R^3$ together are di- or trimethylene optionally substituted by hydroxy;

$R^4$ is lower alkyl, hydroxy-lower alkyl, lower cycloalkyl-lower alkyl, carboxy-lower alkyl, aryl-lower alkyl, lower alkylthio-lower alkyl, cyano-lower alkylthio-lower alkyl, aryl-lower alkylthio-lower alkyl, lower alkenyl, aryl or lower cycloalkyl;

$R^5$ is lower alkyl, hydroxy-lower alkyl, lower alkylthio-lower alkyl, aryl-lower alkyl, aryl-lower alkylthio-lower alkyl, cyano-lower alkylthio-lower alkyl or lower cycloalkyl;

$R^6$ is hydrogen or lower alkyl;

$R^7$ is lower alkyl, hydroxy-lower alkyl, carboxy-lower alkyl, aryl-lower alkyl, lower cycloalkyl-lower alkyl or lower cycloalkyl;

$R^8$ is lower alkyl, hydroxy-lower alkyl, carboxy-lower alkyl or aryl-lower alkyl; and $R^9$ is lower alkylcarbonyl, carboxy-lower alkylcarbonyl, arylcarbonyl, lower alkylsulphonyl, arylsulphonyl, lower alkoxycarbonyl or aryl-lower alkoxycarbonyl; and Q is
(a) 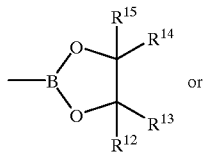
or
(b) 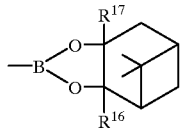
wherein $R^{12}$, $R^{13}$, $R^{14}$ and $R^{15}$ each are hydrogen or lower alkyl and $R^{16}$ and $R^{17}$ each are hydrogen or lower alkyl, and wherein any carboxy, hydroxy or aminocarbonyl group present in the compound is or is not protected.
2. The compound of claim 1 wherein Q is:
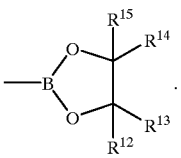
3. The compound of claim 1 wherein Q is:
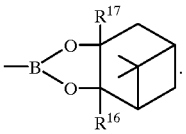
* * * * *